United States Patent
Kolb et al.

(10) Patent No.: US 8,133,472 B2
(45) Date of Patent: *Mar. 13, 2012

(54) CYCLOPEPTIDES CONTAINING RGD MIMETICS AS IMAGING MARKERS FOR INTEGRINS

(75) Inventors: Hartmuth C. Kolb, Playa Del Rey, CA (US); Kai Chen, Rockville, MD (US); Joseph C. Walsh, Pacific Palisades, CA (US); Qianwa Liang, Hacienda Heights, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 412 days.

This patent is subject to a terminal disclaimer.

(21) Appl. No.: 12/433,258

(22) Filed: Apr. 30, 2009

(65) Prior Publication Data

US 2010/0074844 A1 Mar. 25, 2010

Related U.S. Application Data

(60) Provisional application No. 61/049,385, filed on Apr. 30, 2008.

(51) Int. Cl.
*A61K 51/00* (2006.01)
*A61M 36/14* (2006.01)

(52) U.S. Cl. ............... 424/1.69; 424/1.11; 424/1.65; 424/9.1; 424/9.4; 424/9.44

(58) Field of Classification Search ............ 424/1.11, 424/1.45, 1.49, 1.53, 1.57, 1.65, 1.69, 1.73, 424/1.81, 1.85, 1.89, 9.1, 9.2, 9.3, 9.4, 9.5, 424/9.6, 9.7, 9.8, 9.44; 514/1, 1.11, 13.3; 530/300, 316, 317, 331, 333, 334, 338

See application file for complete search history.

(56) References Cited

U.S. PATENT DOCUMENTS

| | | | |
|---|---|---|---|
| 6,534,478 B1 * | 3/2003 | Jonczyk et al. | 514/13.3 |
| 6,537,520 B1 | 3/2003 | Rajopadhye et al. | |
| 7,666,392 B2 * | 2/2010 | Kolb et al. | 424/9.1 |
| 2003/0125243 A1 | 7/2003 | Liu et al. | |
| 2009/0074664 A1 | 3/2009 | Kolb et al. | |

FOREIGN PATENT DOCUMENTS

| | | |
|---|---|---|
| WO | WO9901472 A1 | 1/1999 |
| WO | WO 2006135233 A1 | 12/2006 |
| WO | WO 2007018431 A2 | 2/2007 |
| WO | WO 2008/033561 | 3/2008 |
| WO | WO 2008033557 A2 | 3/2008 |
| WO | WO2008033557 A2 | 3/2008 |
| WO | WO 2008033561 A2 | 3/2008 |

OTHER PUBLICATIONS

Cai, et al., "A thiol-reactive F-labeling agent N[2-(4-18F-Flurobenzamido) Ethyl] Maleimide, and synthesis of RGD peptide-based tracer for PET imaging of alpha v beta 3 integrin expression", Journal of Nuclear Medicine, Society of Nuclear Medicine, Reston, VA, US, vol. 47, No. 7, Jul. 1, 2006; pp. 1172-1180.
Wu, et al., "MicroPET Imaging of Glioma Integrin (alpha)v(beta)3 Expression Using 64Cu-Labeled Tetrameric RGD Peptide", Published in Journal of Nuclear Medicine: Official Publication, Society of Nuclear Medicine Oct. 2005, vol. 46, No. 10 (pp. 1707-1718).
Goodman, et al., "Nanomolar Small Molecule Inhibitors for Alphavbeta6, Alphavbeta5, Integrins ", Journal of Medicinal Chemistry, American Chemical Society, Washington, US, vol. 45, Jan. 31, 2002 (pp. 1045-1051).
Schmidt, et al.: "Synthesis of Entrantriomerically Pure and Compatibly Protected (2S, 3R)- and (2S, 3S)- Diaminobutyric Acids" Published in Synthesis, No. 12, 1992 (pp. 1201-1202); Magazine.
Kuijpers, et al.: "Expedient synthesis of triazole-linked glycosyl amino acids and peptides" Published by Organic Letters, American Chemical Society, vol. 6, No. 18, Sep. 2, 2004 (pp. 3123-3126); Magazine.
Oppolzer, et al.: "Non-destructive Cleavage of N-Acylsultams Under Neutral Conditions" Preparation of Enantiomerically Pure Fmoc-Protected alpha-Amino Acids Published by Helvetica Chimica Acta, vol. 75, 1992 (pp. 2572-2582; Magazine.
Franke, et al.: "Peptide ligation through click chemistry for the generation of assembled and scaffolded peptides" Published in Tetrahedron Letters, Elsevier, Science Direct, vol. 46, No. 26, Jun. 27, 2005 (pp. 4479-4482); Magazine.
International Search Report in Application No. PCT/US2009/003309 dated Nov. 12, 2009.
Haubner, et al.: "(18F) Galacto-RGD: Synthesis, Radiolabeling, Metabolic Stability, and Radiation Dose Estimates" Bioconjugate Chemistry, ACS, Washington, DC, US, vol. 15, No. 1, Jan. 1, 2004, pp. 61-69.
Chen, et al., "MicroPET Imaging of brain tumor angiogenesis with 18 F labeled PEGylated RGD peptide" European Journal of Nuclear Medicine and Molecular Imaging, Springer Verlag, Heidelberg, DE, vol. 31, No. 8, Aug. 1, 2004.
Belvisi et al.: "Potent Integrin Antagonists From a Small Library of RGD-including Cyclic Pseudopeptides", Organic Letters, vol. 3, No. 7, 2001, pp. 1001-1004.
Preliminary Report on Examination for Application No. PCT/US2008/071266 dated Nov. 25, 2009.
International Search Report for Application No. PCT/US2008/059599 dated Dec. 3, 2008.
Ryppa Claudia et al; "In vitro and in vivo evaluation of doxorubicin conjugates with the divalent peptide E-[c(RGDfK)(2)] that targets integrin alpha(v)beta(3)" Bioconjugate Chemistry, vol. 19, No. 7, Jul. 2008, pp. 1414-1422; XP002538414; ISSN: 1043-1802; Magazine; 2008; US.
Dijkgraaf Ingrid et al: "Synthesis of DOTA-conjugated multivalent cyclic-RGD peptide dendrimers via 1,3-dipolar cycloaddition and their biological evaluation: implications for tumor targeting and tumor imaging purposes" Organic and Biomolecular Chemistry, Royal Society of Chemistry, Cambridge, GB, vol. 5, No. 6, Mar. 21, 2007; pp. 953-944, XP002470091; ISSN: 1477-0520; Magazine; 2007; GB.

(Continued)

Primary Examiner — D L Jones
(74) Attorney, Agent, or Firm — Joshua B. Ryan

(57) ABSTRACT

Radiolabeled cyclic polypeptides, pharmaceutical compositions comprising radiolabeled cyclic polypeptides, and methods of using the radiolabeled cyclic polypeptides. Such polypeptides can be used in imaging studies, such as Positron Emitting Tomography (PET) or Single Photon Emission Computed Tomography (SPECT).

29 Claims, 7 Drawing Sheets

OTHER PUBLICATIONS

Li Zi-Bo et al; "Click chemistry for (18)F-labeling of RGD peptides and microPET imaging of tumor integrin alphavbeta3 expressin" Bioconjugate Chemistry, ACS, Washington, DC, US; vol. 18, No. 6; Nov. 1, 2007, pp. 1987-1994, XP002470093 ; ISSN: 1043-1802; Magazine; 2007; US.

Chen Xiaoyuan et al; "Pegylated Arg-Gly-Asp peptide: 64 Cu labeling and PET imaging of brain tumor alphavbeta3-integrin expression" Journal of Nuclear Medicine, vol. 45, No. 10, Oct. 2004; pp. 1776-1783, XP002538420; Magazine; 2004; US.

Jeong Jae Min et al; "Preparation of a promising angiogenesis PET imaging agent: Ga-68-labeled c(RGDyK)-isothiocyanatobenzyl-1, 4,7-triaza cyclononane-1,4, 7-triacetic acid and feasibility studies in mice" Journal of Nuclear Medicine, vol. 49, No. 5, May 2008; pp. 830-836, XP002538417; ISSN: 0161-5505; Magazine; 2008; US.

Hamidpour Mohsen et al.; "The isolation and characterization of antiplatelet antibodies" European Journal of Haematology, vol. 76, No. 4, Apr. 2006; pp. 331-338; XP002538413; Magazine; 2006; GB.

International Search Report for Application No. PCT/US2009/002627 dated Nov. 17, 2009.

Ingrid Dijkgraaf, et al.; "Synthesis of DOTA-conjugated multivalent cyclic-RGD peptide dendrimers via 1, 3-dipolar cycloaddition and their biological evaluation: implications for tumor targeting and tumor imaging purposes;" Org. Biomol, Chem., vol. 5, No. 6, Mar. 21, 2007, pp. 935-944.

Xiaoyuan Chen, PhD; et al.; "Pegylated Arg-Gly-Asp Peptide: $^{64}$Cu Labeling and PET imaging of Brain Tumor $\alpha\beta_3$-Integrin Expression;" The Journal of Nuclear Medicine; vol. 45, No. 10, Oct. 2004, pp. 1776-1783.

Jae Min Jeong, et al.; "Preparation of a Promising Angiogenesis PET Imaging Agent: $^{68}$GA-Labeled c(RGDyK)-Isothiocyanatobenzyl-1, 4, 7-Triazacyclononane-1, 4, 7-Triacetic Acid and Feasibility Studies in Mice;" The Journal of Nuclear Medicine, vol. 49, No. 5, May 2008, pp. 830-836.

Zi-Bo Li, et al.; "Click Chemistry for $^{18}$F-Labeling of RGD Peptides and MicroPET Imaging of Tumor Integrin $\alpha_v\beta_3$ Expression;" 2007 American Chemical Society, Bioconjugate Chem. vol. 18, No. 6, Nov. 1, 2007, pp. 1987-1994.

Hamidpour M. Behrendt. et al. "The Isolation and Characterisation of Antiplatelet Antibodies;" Eur. J. Haematol 2006: vol. 76, No. 4, Apr. 4, 2006, pp. 331-338.

Claudia Ryppa, et al.; "In vitro and in vivo evaluation of doxorubicin conjugates with the divalent peptide E-[c(RGDfK)(2)] that targets integrin alpha(v)beta(3)" Bioconjugate Chemistry, vol. 19, No, 7, Jul. 2008, pp. 1414-1422.

* cited by examiner

| TUMOR | %ID/g | TUMOR/MUSCLE RATIO | TUMOR SIZE (cm$^3$) |
|---|---|---|---|
| RS | 0.042 | 1.64 | 0.01 |
| LS | 0.034 | 1.33 | 0.01 |
| MUSCLE | 0.025 | – | – |

CYCLOPEPTIDES CONTAINING RGD MIMETICS AS IMAGING MARKERS FOR INTEGRINS

INCORPORATION BY REFERENCE

This application claims benefit of U.S. provisional application Ser. No. 61/049,385 filed Apr. 30, 2008.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference in their entirety, and may be employed in the practice of the invention.

FIELD OF THE INVENTION

Embodiments of the present invention is directed to radiolabeled cyclic polypeptides (cyclopeptides), pharmaceutical compositions comprising radiolabeled cyclic polypeptides, and methods of using the radiolabeled cyclopeptides. Embodiments of the invention are further directed to methods of preparing the radiolabeled cyclopeptides. Such cyclopeptides can be used in imaging studies, such as Positron Emitting Tomography (PET) or Single Photon Emission Computed Tomography (SPECT).

BACKGROUND OF THE INVENTION

A number of medical diagnostic procedures, including PET and SPECT utilize radiolabeled compounds. PET and SPECT are very sensitive techniques and require small quantities of radiolabeled compounds, called tracers. The labeled compounds are transported, accumulated and converted in vivo in exactly the same way as the corresponding non-radioactively labeled compound. Tracers or probes can be radiolabeled with a radionuclide useful for PET imaging, such as $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$ and $^{131}I$, or with a radionuclide useful for SPECT imaging, such as $^{99}Tc$, $^{75}Br$, $^{61}Cu$, $^{153}Gd$, $^{125}I$, $^{131}I$ and $^{32}P$.

PET creates images based on the distribution of molecular imaging tracers carrying positron-emitting isotopes in the tissue of the patient. The PET method has the potential to detect malfunction on a cellular level in the investigated tissues or organs. PET has been used in clinical oncology, such as for the imaging of tumors and metastases, and has been used for diagnosis of certain brain diseases, as well as mapping brain and heart function. Similarly, SPECT can be used to complement any gamma imaging study, where a true 3D representation can be helpful, for example, imaging tumor, infection (leukocyte), thyroid or bones.

Angiogenesis plays a vital role in tumor growth and metastatic spread. Tumor angiogenesis is a multi-step process characterized by chemotactic and mitogenic response of endothelial cells to angiogenic growth factors, proteolytic degradation of extracellular matrix, and modulation of endothelial cell interaction with extracellular matrix mediated by integrin receptors. Each of these steps may represent a potential target for the development of tumor angiogenic and metastatic diagnostics.

Integrins are a family of membrane-spanning adhesion receptors composed of noncovalently linked α and β subunits, which combine to form a variety of heterodimers with different ligand recognition properties. Several integrins have been shown to interact with polypeptide domains containing the Arg-Gly-Asp ("RGD") amino acid sequence present in various extracellular matrix-associated adhesive glycoproteins. Besides cell adhesion to extracellular matrix, integrins also mediate intracellular events that control cell migration, proliferation and survival.

One member of the integrin family, $\alpha_v\beta_3$ integrin, plays a key role in angiogenesis. It interacts with several extracellular matrix proteins, such as vitronectin, fibrinogen, fibronectin, thrombin and thrombospondin, and cooperates with molecules such as metalloproteases, growth factors, and their receptors. Due to its numerous functions and relatively limited cellular distribution, $\alpha_v\beta_3$ integrin represents an attractive target for diagnostic and therapeutic intervention. In addition, findings that several extracellular matrix proteins, such as vitronectin, fibrinogen, and thrombospondin interact with integrins via the RGD sequence have lead to the development of synthetic linear and cyclic peptides containing RGD sequence for integrin targeting. See for example, DE 197 25 368, U.S. Pat. No. 5,849,692, U.S. Pat. No. 6,169,072, U.S. Pat. No. 6,566,491, U.S. Pat. No. 6,610,826 and WO 2005/111064.

Researchers have demonstrated in a number of human xenograft tumor models in mice that radiolabeled peptides containing the RGD motif can be used for non-invasive investigation of $\alpha_v\beta_3$ integrin expression. The development of non-invasive methods to visualize and quantify integrin $\alpha_v\beta_3$ expression in vivo complements the use of antiangiogenic therapy based on integrin antagonism. For example, non-invasive integrin imaging is first used to evaluate the efficacy of anti-integrin based therapeutics and, secondly, may be used as a tool for optimizing both favorable tumor targeting and in vivo kinetic properties of new drug candidates. Imaging can also be used to provide an optimal dosage regimen and time course for patient treatment based on receptor occupancy studies. Precise documentation of integrin receptor levels may allow for a more accurate selection of patients who will most likely benefit from anti-integrin based treatments.

Kessler and co-workers [1] developed the pentapeptide cyclo(-Arg-Gly-Asp-D-Phe-Val-) ("c(RGDfV)") which showed both high affinity and selectivity for integrin $\alpha_v\beta_3$. To date, most integrin $\alpha_v\beta_3$ targeted PET studies have utilized the radiolabeling of c(RGDfV)-based antagonists due to their high binding affinities which range from nanomolar to sub-nanomolar range for monomeric and multimeric c(RGDfV) respectively. In the late 1990's, Haubner et al. [2] prepared a monomeric peptide c(RGDyV) labeled with $^{125}I$. This tracer possessed receptor-specific tumor uptake in vivo, however, the labeled peptide had rapid tumor washout and unfavorable hepatobiliary excretion, due to its high lipophilicity, thus limiting its imaging applications. In an effort to develop an imaging agent with more favorable properties, glycosylation of the lysine side chain of an RGD peptide analog, c(RGDyK), decreased both the tracer's lipophilicity and hepatic uptake [3]. The resultant F-18 labeled glycopeptide was then synthesized and imaged:

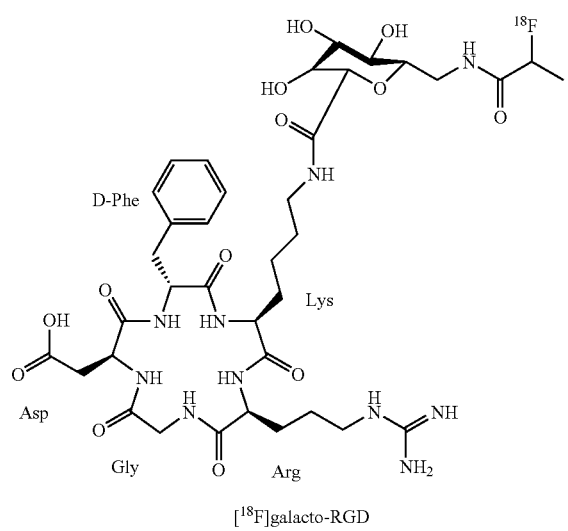

[$^{18}$F]galacto-RGD

[$^{18}$F]Galacto-RGD exhibits integrin $\alpha_v\beta_3$-specific tumor uptake in integrin-positive M21 melanoma xenograft mouse models (4-6, see also 19). When [$^{18}$F]galacto-RGD was imaged in mice with an integrin negative cell line, the A431 human squamous cell carcinoma model, the tracer did not localize on tumor cells, but rather localized at tumor vasculaturization sites having integrin $\alpha_v\beta_3$ expression. Initial clinical trials results from both healthy volunteers and cancer patients showed that the tracer was both safe and effective in detecting certain lesions that were integrin-positive with reasonable contrast.

[$^{18}$F]Galacto-RGD currently represents one promising integrin marker for PET imaging of angiogenesis. As a monomeric RGD peptide tracer, it has a relatively low tumor targeting efficacy. In addition, its clinical utility is severely limited because of its relatively low integrin binding affinity, modest tumor standard uptake values, and unfavorable pharmacokinetic behavior. Therefore, tumors with low integrin expression levels may not be detectable. In addition, prominent tracer accumulation in the liver, kidneys, spleen, and intestines was observed in both preclinical models and human studies resulting in difficult visualization of abdomen lesions. To add to its imaging drawbacks, the synthetic preparation of the tracer is labor intensive, time consuming and inefficient, thereby limiting its widespread availability to clinicians.

Conjugation of PEG (poly(ethyleneglycol)) ("PEGylation") has been shown to improve many properties of peptides and proteins, including plasma stability, immunogenicity, and pharmacokinetics. Chen et al. [7-9] conjugated RGD-containing peptides with PEG moieties of different sizes and en route to preparing radioiodinated, $^{18}$F- and $^{64}$Cu-labeled derivatives. Attachment of the PEG group favorably affected the pharmacokinetics, tumor uptake and retention of the tracer in human xenograft mouse models. The biological uptake and distribution appears to depend strongly on the nature and quantity of the cyclic peptide as well as the size of the PEG moiety. In an effort to further improve the imaging of cyclic peptides by improving PK, tumor uptake and retention, two strategies focused on the incorporation of hydrophilic amino acids and multimerisation of RGD.

Citation or identification of any document in this application is not an admission that such document is available as prior art to the present invention.

REFERENCES

1. Aumailley, M.; Gurrath, M.; Muller, G.; Calvete, J.; Timpl, R.; Kessler, H., *FEBS Lett.* 1991, 291, 50-54. 2. Haubner, R.; Wester, H. J.; Reuning, U.; Senekowisch-Schmidtke, R.; Diefenbach, B.; Kesser, B.; Stocklin, G.; Schwaiger, M., *J. Nucl. Med.*, 1999, 40, 1061-1071. 3. Haubner, R.; Wester, H. J.; Burkhart, F.; Senekowisch-Schmidtke, R.; Weber, W.; Goodman, S. L.; Kessler, H.; Schwaiger, M., *J. Nucl. Med.*, 2001, 42, 326-336. 4. Haubner, R.; Weber, W. A.; Beer, A. J.; Vabuliene, E.; Reim, D.; Sarbia, M.; Becker, K. F.; Goebel, M., et al. *PLoS Med.*, 2005, 2, e70. 5. Haubner, R.; Wester, H. J.; Weber, W. A.; Mang, C.; Ziegler, S. I.; Goodman, S. L.; Senekowisch-Schmidtke, R.; Kessler, H.; Schwaiger, M., *Cancer Res.*, 2001, 61, 1781-1785. 6. Haubner, R.; Kuhnast B; Mang, C.; Weber W. A.; Kessler, H.; Wester, H. J.; Schwaiger, M., *Bioconjug. Chem.*, 2004, 15, 61-69. 7. Chen, X.; Park, R.; Shahinian, A. H.; Bading, J. R.; Conti, P. S., *Nucl. Med. Biol.*, 2004, 31, 11-19. 8. Chen, X.; Park, R.; Hou, Y.; Khankaldyyan, V.; Gonzales-Gomez, I.; Tohme, M.; et al., *Eur. J. Nul. Med. Mol. Imaging*, 2004, 31, 1081-1089. 9. Chen, X.; Hou, Y.; Tohme, M.; Park, R.; Khankaldyyan, V.; Gonzales-Gomez, I.; et al., *J. Nul. Med.*, 2004, 45, 1776-1783. 10. Kolb, H. C.; Finn, M. G.; Sharpless, K. B. *Angewandte Chemie, International Edition* 2001, 40, 2004-2021. 11. Kolb, H. C.; Sharpless, K. B., *Drug Discovery Today* 2003, 8, 1128-1137. 12. Rostovtsev, V. V.; Green, L. G.; Fokin, V. V.; Sharpless, K. B. *Angewandte Chemie, International Edition* 2002, 41, 2596-2599. 13. Tornøe, C. W.; Christensen, C.; Meldal, M., *Journal of Organic Chemistry* 2002, 67, 3057-3064. 14. Wang, Q.; Chan, T. R.; Hilgraf, R.; Fokin, V. V.; Sharpless, K. B.; Finn, M. G., *Journal of the American Chemical Society* 2003, 125, 3192-3193. 15. Lee, L. V.; Mitchell, M. L.; Huang, S.-J.; Fokin, V. V.; Sharpless, K. B.; Wong, C.-H., *Journal of the American Chemical Society* 2003, 125, 9588-9589. 16. Lewis, W. G.; Green, L. G.; Grynszpan, F.; Radic, Z.; Carlier, P. R.; Taylor, P.; Finn, M. G.; Barry, K., *Angew. Chem., Int. Ed.* 2002, 41, 1053-1057. 17. Manetsch, R.; Krasinski, A.; Radic, Z.; Raushel, J.; Taylor, P.; Sharpless, K. B.; Kolb, H. C., *Journal of the American Chemical Society* 2004, 126, 12809-12818. 18. Mocharla, V. P.; Colasson, B.; Lee, L. V.; Roeper, S.; Sharpless, K. B.; Wong, C.-H.; Kolb, H. C., *Angew. Chem. Int. Ed.* 2005, 44, 116-120. 19. Beer, A. J., et al., *J. Nucl. Med.* 2006 47:763-769.

SUMMARY OF THE INVENTION

For successful imaging of RGD tracer, several key challenges still need resolving. First, the pharmacokinetic behavior of the tracer is suboptimal due to multi-organ accumulation of the tracer. Although glycosylation of RGD improved the pharmacokinetic behavior to a certain degree, prominent tracer accumulation in the liver, kidneys, spleen, and intestines is still observed in both preclinical models and human studies, making lesion visualization in the abdominal region difficult. Second, a major drawback of the strategies examined by others is the employment of difficult, time consuming and inefficient radiolabeling protocols which severely limits the exploration of improved derivatives and the use of these imaging agents as standard clinical biomarkers. Third, most integrin $\alpha_v\beta_3$ targeted radiolabeling cyclopeptides are limited to the RGD binding motif.

It would be an advancement in the art to reduce low signal to noise ratios, and unfavorable pharmacokinetic properties. Indeed, a library of RGD mimetic sequences as binding motif has been built as potential integrin imaging agents. The library of markers was screened for binding to integrins. The cyclopeptides that displayed high binding affinities were selected for radiolabeling with positron-emitting isotopes or conjugation with appropriate linker moieties and radioactive isotopes such as [18F]-fluorine for in vivo PET imaging. The applicants' approach to using click chemistry enabled rapid synthesis and testing of many different potential integrin ligands as candidate PET tracers.

In one embodiment, the present invention is directed to cyclopeptides containing RGD mimetics presenting unexpected high binding affinity to integrin $\alpha_v\beta_3$ (FIG. 1-4). Cyclopeptides containing RGD mimetics, as disclosed in the present invention, would lead to a class of compound, exemplified by RAD fragment-containing compounds, such as compounds 4 and 18, which display high binding affinity to $\alpha_v\beta_3$.

In another embodiment, the present invention is directed to imaging agents effective for detecting angiogenic tumors in vivo. The labeled cyclopeptidic RGD mimetics of the present application, contain polar residues on a pendant amino acid side chain and those polar residues are coupled with a moiety comprising a radionuclide via a 'click chemistry' linkage (i.e. a 1,4- or 1,5-disubstituted 1,2,3-triazole). These click chemistry-derived compounds are easy to both synthesize and radiolabel. The compounds demonstrate surprisingly high binding affinity to integrin $\alpha_v\beta_3$ (FIG. 1), and improved pharmacokinetic properties compared to cyclic polypeptides belonging to the same class. The imaging agents disclosed in the present application are useful markers for imaging integrins in vivo. For PET imaging, it is beneficial for a compound to be cleared quickly and via the renal route (kidneys), as opposed to liver-GI clearance. The "click" compounds, as disclosed in the present invention, exemplified by compound 19, display the preferred renal clearance, relative to liver-GI clearance.

In another embodiment, this invention is directed to a means for detecting blood vessel growth in certain cancers in vivo, as well as a means for monitoring the efficacy of cancer therapy. Since the imaging agent allows in vivo imaging of blood vessel growth in solid tumors, it enables personalized anti-angiogenesis cancer therapies.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which.

DETAILED DESCRIPTION

Figure 1A:
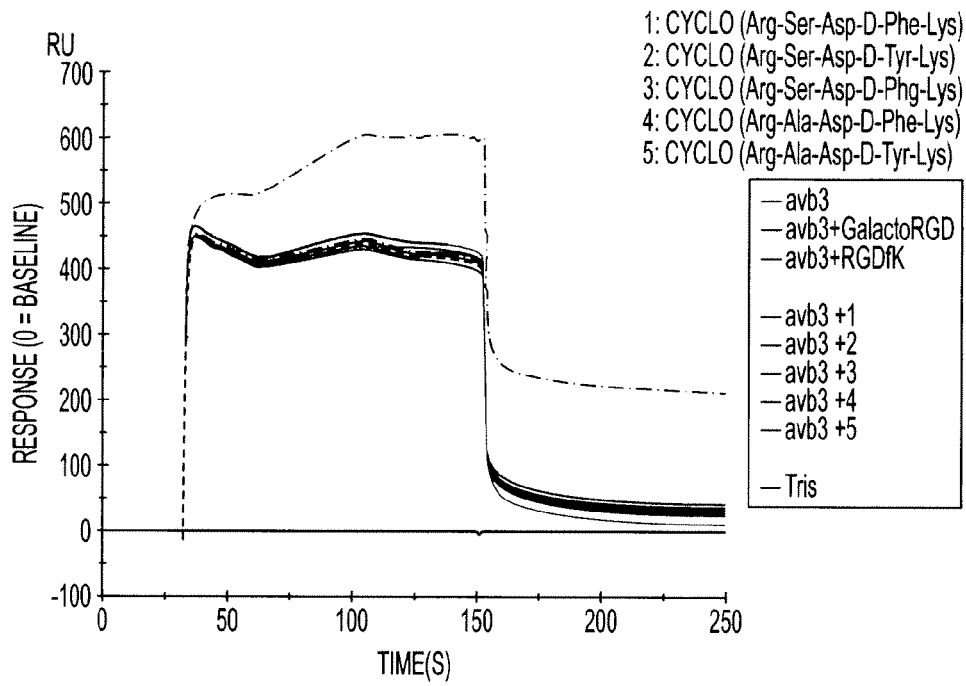
FIG. 1 is a graph of binding affinity determination of cyclopeptides containing RGD mimetics using surface plasmon resonance assay.
Figure 1B:
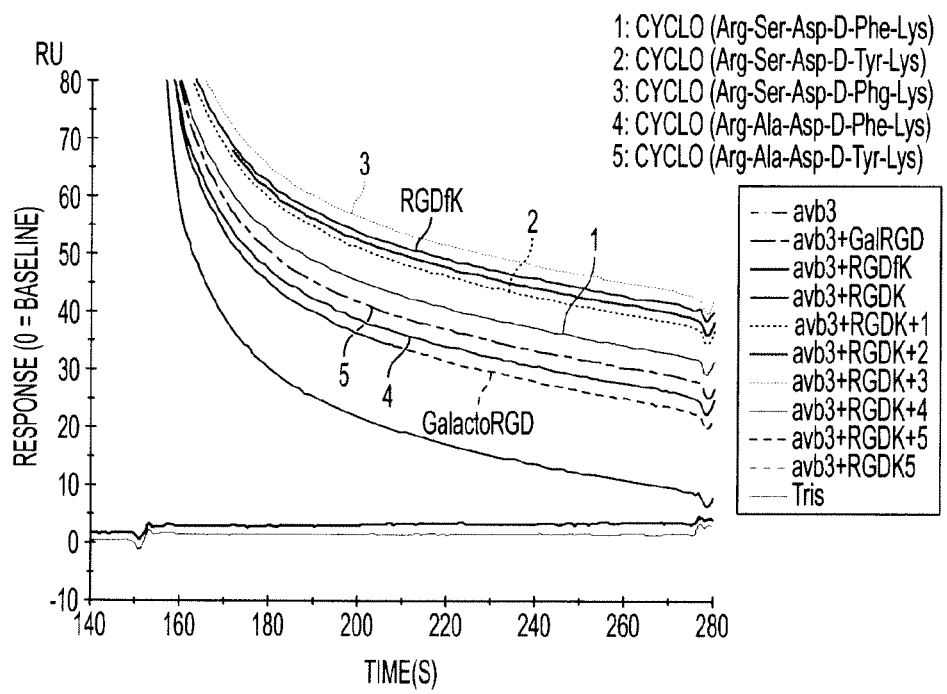
Figure 1C:
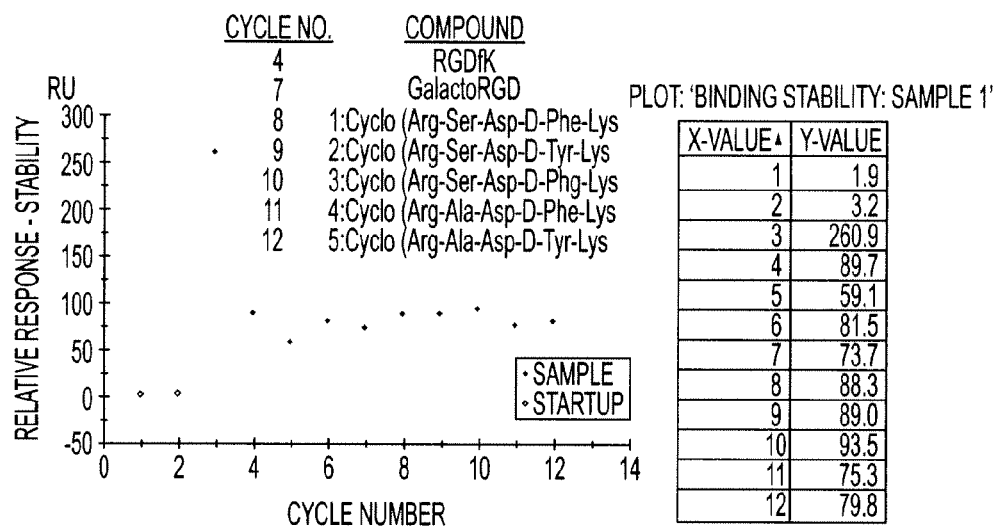
Figure 1D:
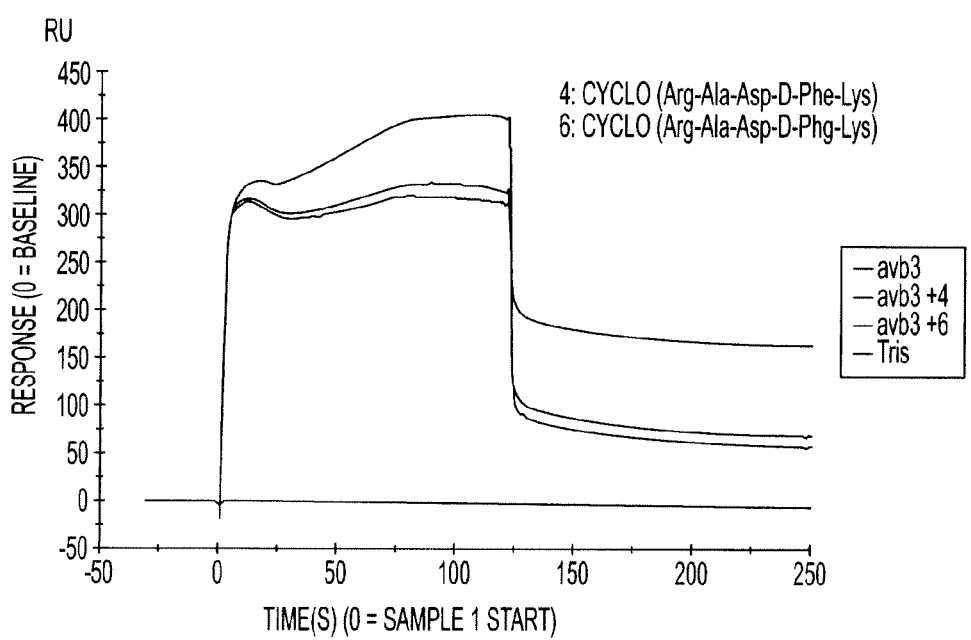

The embodiments of the invention and the various features and advantageous details thereof are explained more fully with reference to the non-limiting embodiments, aspects and examples that are described and/or illustrated in the accompanying figures and detailed in the following description. It should be noted that the features of one embodiment or aspect may be employed with other embodiments as the skilled artisan would recognize, even if not explicitly stated herein. The examples used herein are intended merely to facilitate an understanding of ways in which the invention may be practiced and to further enable those of skill in the art to practice the embodiments of the present invention. Accordingly, the examples and embodiments herein should not be construed as limiting the scope of the invention, which is defined solely by the appended claims. Unless specifically noted otherwise herein, the definitions of the terms used are standard definitions used in the art of organic and peptide synthesis and pharmaceutical sciences.

An "alkyl" group is a straight, branched, saturated or unsaturated, aliphatic group having a chain of carbon atoms, optionally with oxygen, nitrogen or sulfur atoms inserted between the carbon atoms in the chain or as indicated. Alkyl groups may be optionally substituted. A $(C_1-C_6)$alkyl, for example, includes each of the alkyl groups that have a chain of between 1 and 6 carbon atoms, and include, for example, the groups methyl (i.e., $C_1$ alkyl), ethyl ($C_2$ alkyl), propyl ($C_3$ alkyl), isopropyl ($C_3$ alkyl), vinyl, allyl, 1-propenyl, isopropenyl, ethynyl, 1-propynyl, 2-propynyl, 1,3-butadienyl ($C_4$ alkyl), penta-1,3-dienyl ($C_5$ alkyl), and the like. An alkyl group, such as "$C_1$-$C_6$ alkyl," that forms a part of a group or linker is a divalent alkyl group, and also may be referred to as an "alkylene" or "alkylenyl" group. Similarly, an alkenyl group, alkynyl group, aryl group, etc in a structure that is shown as a divalent group may be referred to as an alkenylenyl, alkynylenyl, arylenyl group, respectively. The representation of "$(C_{1-3})$alkyl", for example, is used interchangeably with "$C_1$-$C_3$alkyl" to mean the same.

An alkyl as noted with another group such as an aryl group, represented as "arylalkyl" for example, is intended to be a straight, branched, saturated or unsaturated aliphatic divalent group with the number of atoms indicated in the alkyl group (as in $(C_1-C_6)$alkyl, for example) and/or aryl group or when no atoms are indicated means a bond between the aryl and the alkyl group. Nonexclusive examples of such group include benzyl, phenylethyl and the like.

An "alkylene" group or "alkylenyl" group is a straight, branched, saturated or unsaturated aliphatic divalent group with the number of atoms indicated in the alkyl group; for example, a —$(C_1-C_3)$alkylene- or —$(C_1-C_3)$alkylenyl-.

The term "alkenyl" refers to unsaturated groups which contain at least one carbon-carbon double bond and includes straight-chain, branched-chain and cyclic groups. Alkene groups may be optionally substituted. Exemplary groups include 1-butenyl, 2-butenyl, 3-butenyl, isobutenyl, 1-propenyl, 2-propenyl and ethenyl.

The term "alkoxy" or "alkyloxy" includes linear or branched alkyl groups that are attached to divalent oxygen. The alkyl group is as defined above. Examples of such substituents include methoxy, ethoxy, t-butoxy, and the like. The term "alkoxyalkyl" refers to an alkyl group that is substituted with one or more alkoxy groups. Alkoxy groups may be optionally substituted. The term "aryloxy" refers to an aryl group that is attached to an oxygen, such as phenyl-O—, etc.

The term "alkynyl" refers to unsaturated groups which contain at least one carbon-carbon triple bond and includes straight-chain, branched-chain and cyclic groups. Alkyne groups may be optionally substituted. Exemplary groups include 1-butynyl, 2-butynyl, 3-butynyl, 1-propynyl, 2-propynyl and ethynyl.

"Aryl" means one or more aromatic rings, each of which may comprise 5 or 6 core carbon atoms. Aryl includes multiple aryl rings that may be fused, as in naphthyl or non-fused, as in biphenyl. Aryl rings may also be fused or non-fused with one or more cyclic hydrocarbon, heteroaryl or heterocyclic rings. As used herein, "aryl" includes heteroaryl.

The term "carbocycle" (or carbocyclyl) as used herein refers to a $C_3$ to $C_{14}$ monocyclic or bicyclic, saturated, partially saturated or aromatic ring. Bonds in a carbocycle depicted as "---"indicate bonds that can be either single or double bonds. Carbocycles may be optionally substituted. Non-exclusive examples of carbocycle include cyclopropane, cyclobutane, cyclopentane, cyclohexane, cycloheptane, cyclopentene, cyclohexene, cycloheptene, cyclooctene, benzyl, naphthene, anthracene, phenanthracene, biphenyl and pyrene.

The term "halo" or "halogen" means fluoro, chloro, bromo and iodo.

A "heterocycle" is a carbocycle group wherein one or more of the atoms forming the ring is a heteroatom that is a N, O or S. The heterocycle may be saturated, partially saturated or aromatic. Bonds in a heterocycle depicted as "---"indicate bonds that can be either single or double bonds. Heterocycles may be optionally substituted. Non-exclusive examples of heterocyclyl (or heterocycle) include triazoles (e.g., 1,2,3-triazoles), piperidyl, 4-morpholyl, 4-piperazinyl, pyrrolidinyl, 1,4-diazaperhydroepinyl, acetonidyl-4-one, 1,3-dioxanyl, thiophenyl, furanyl, pyrrolyl, pyrazolyl, pyridinyl, pyrimidinyl, pyridazinyl, pyranyl and the like.

The term "optionally substituted" or "substituted" refers to the specific group wherein one to four hydrogen atoms in the group may be replaced by one to four substituents, independently selected from alkyl, aryl, alkylaryl, hydroxy, alkoxy, aryloxy, perhaloalkoxy, heterocycle, azido, amino (such as —$NH_2$, —$NH(C_1-C_{10})$alkyl, —$N[(C1-C10)alkyl]_2$, —NHaryl, —N(aryl)(C1-C10)alkyl, etc. . . . ), guanidino, amidino, halo, alkylthio, oxo (—C(O)—), acylalkyl, carboxy esters, carboxyl, carboxamido, nitro, acyloxy, aminoalkyl, alkylaminoaryl, alkylaminoalkyl, alkoxyaryl, arylamino, phosphono, sulfonyl, carboxamidoaryl, hydroxyalkyl, haloalkyl, cyano, alkoxyalkyl and perhaloalkyl. In addition, the term "optionally substituted" or "substituted" in reference to R2, R3 or R7 for example, includes groups substituted by one to four substituents, as identified above, that further comprises a positron or gamma emitter. Such positron emitters include, but are not limited to, $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$, and $^{32}P$.

As used herein, the term "side chain" of a natural or unnatural amino acid refers to "Q" group in the amino acid formula, as exemplify with $NH_2CH(Q)CO_2H$.

As used herein, the term "polar amino acid moiety" refers to the side chain, Q, of a polar natural or unnatural amino acid. Polar natural amino acids include but are not limited to arginine, asparagine, aspartic acid, cysteine, glutamic acid, glutamine, histidine and lysine.

As used herein, "natural amino acid" refers to the naturally occurring amino acids: glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine and lysine. Accordingly, a derivative of an amino acid may be an ester, such as a $(C_1-C_6)$alkyl ester, a protected amino acid such as an N-acetyl amino acid, and combinations thereof.

The term "unnatural amino acid" refers to any derivative of a natural amino acid including for example D and L forms, and α- and β-amino acid derivatives. It is noted that certain amino acids, e.g., hydroxyproline, that are classified as a non-natural amino acid herein, may be found in nature within a certain organism or a particular protein. The following non-exclusive examples of non-natural amino acids and amino acid derivatives may be used according to the application (common abbreviations in parentheses): β-alanine (β-ALA), γ-aminobutyric acid (GABA), ornithine, 2-aminobutyric acid (2-Abu), α,β-dehydro-2-aminobutyric acid (8-AU), 1-aminocyclopropane-1-carboxylic acid (ACPC), aminoisobutyric acid (Aib), γ-carboxyglutamic acid, 2-amino-thiazoline-4-carboxylic acid, 5-aminovaleric acid (5-Ava), 6-aminohexanoic acid (6-Ahx), 8-aminooctanoic acid (8-Aoc), 11-aminoundecanoic acid (11-Aun), 12-aminododecanoic acid (12-Ado), 2-aminobenzoic acid (2-Abz), 3-aminobenzoic acid (3-Abz), 4-aminobenzoic acid (4-Abz), 4-amino-3-hydroxy-6-methylheptanoic acid (Statine, Sta), aminooxyacetic acid (Aoa), 2-aminotetraline-2-carboxylic acid (ATC), 4-amino-5-cyclohexyl-3-hydroxypentanoic acid (ACHPA), para-aminophenylalanine (4-$NH_2$-Phe), biphenylalanine (Bip), para-bromophenylalanine (4-Br-Phe), ortho-chlorophenylalanine] (2-Cl-Phe), meta-chlorophenylalanine (3-Cl-Phe), para-chlorophenylalanine (4-Cl-Phe), meta-chlorotyrosine (3-Cl-Tyr), para-benzoylphenylalanine (Bpa), tert-butylglycine (TLG), cyclohexylalanine (Cha), cyclohexylglycine (Chg), 2,3-diaminopropionic acid (Dpr), 2,4-diaminobutyric acid (Dbu), 3,4-dichlorophenylalanine (3,4-$C_{12}$-Phe), 3,4-difluorophenylalanine (3,4-$F_2$-Phe), 3,5-diiodotyrosine (3,5-$I_2$-Tyr), ortho-fluorophenylalanine (2-F-Phe), meta-fluorophenylalanine (3-F-Phe), para-fluorophenylalanine (4-F-Phe), meta-fluorotyrosine (3-F-Tyr), homoserine (Hse), homophenylalanine (Hfe), homotyrosine (Htyr), 5-hydroxytryptophan (5-OH-Trp), hydroxyproline (Hyp), para-iodophenylalanine (4-1-Phe), 3-iodotyrosine (3-1-Tyr), indoline-2-carboxylic acid (Idc), isonipecotic acid (Inp), meta-methyltyrosine (3-Me-Tyr), 1-naphthylalanine (1-Nal), 2-naphthylalanine (2-Nal), para-nitrophenylalanine (4-$NO_2$-Phe), 3-nitrotyrosine (3-$NO_2$-Tyr), norleucine (Nle), norvaline (Nva), ornithine (Orn), ortho-phosphotyrosine ($H_2PO_3$-Tyr), octahydroindole-2-carboxylic acid (Oic), penicillamine (Pen), pentafluorophenylalanine ($F_5$-Phe), phenylglycine (Phg), pipecolic acid (Pip), propargylglycine (Pra), pyroglutamic acid (PGLU), sarcosine (Sar), tetrahydroisoquinoline-3-carboxylic acid (Tic), thienylalanine, and thiazolidine-4-carboxylic acid (thioproline, Th). Additionally, N-alkylated amino acids may be used, as well as amino acids having amine-containing side chains (such as Lys and Orn) in which the amine has been acylated or alkylated.

As used herein, "sugar moiety" refers to an oxidized, reduced or substituted saccharide monoradical or diradical covalently attached via any atom(s) of the sugar moiety. Representative sugars include, by way of illustration, hexoses such as D-glucose, D-mannose, D-xylose, D-galactose, vancosamine, 3-desmethyl-vancosamine, 3-epi-vancosamine, 4-epi-vancosamine, acosamine, actinosamine, daunosamine, 3-epi-daunosamine, ristosamine, D-glucamine, N-methyl-D-glucamine, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; disaccharides such as 2-O-(α-L-vancosaminyl)-D-glucopyranose, 2-O-(3-desmethyl-α-L-vancosaminyl)-β-D-glucopyranose, sucrose, lactose, or maltose; derivatives such as acetals, amines, acylated, sulfated and phosphorylated sugars; and oligosaccharides having from 2 to 10 sugar units.

As used herein, a hexose structure that is represented below, for example:

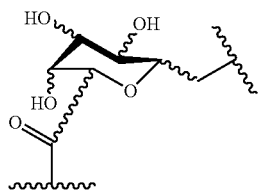

showing the curved lines (∼) is intended to represent a structure having the stereochemistry of any one of the natural sugars, including allose, altrose, galactose, glucose, gulose, idose, mannose, talose, etc. . . . , as well as their unnatural and synthetic hexose analogs and derivatives, and also includes certain sugar moieties.

As used herein, "sugar mimetic" refers to carbocycles or heterocycles substituted with at least one hydroxyl group. Such carbocycle groups include, but are not limited to cyclohexane, cyclohexene, cyclopentane and cyclobutane; such heterocycles include, but are not limited to, pyrrolidine and piperidine.

As used herein, "PEG moiety" refers to a fragment of poly(ethylene glycol), a polymer of ethylene oxide. PEG has the formula:

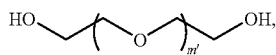

where m' is an integer between 1 and 200, alternatively between 1 and 110 or between 10 and 90; m' can also be an integer between 50 and 75. Alternately m' can be an integer between 1 and 50 or between 1 and 15 or between 1 and 10. As used herein, the clauses defining a variable as between two numbers, such as "an integer between 1 and 10" for example, also include 1 and 10.

"Linker" as used herein refers to a chain comprising 1 to 200 atoms and may comprise atoms or groups, such as C, —NR—, O, S, —S(O)—, —S(O)$_2$—, CO, —C(NR)—, a PEG moiety, and the like, and combinations thereof as defined herein, and wherein R is H or is selected from the group consisting of (C$_{1-10}$)alkyl, (C$_{3-8}$)cycloalkyl, aryl(C$_{1-5}$)alkyl, heteroaryl(C$_{1-5}$)alkyl, amino, aryl, heteroaryl, hydroxy, (C$_{1-10}$)alkoxy, aryloxy, heteroaryloxy, each substituted or unsubstituted. In one aspect, the linker may be a chain comprising 1 to 100 atoms and may comprise of 1, 2 or 3 adjacent or non-adjacent atoms or groups, such as C, —NR—, O, S, —S(O)—, —S(O)$_2$—, CO, —C(NR)— and the like, and wherein R is H or is selected from the group consisting of (C$_{1-10}$)alkyl, (C$_{3-8}$)cycloalkyl, aryl(C$_{1-5}$)alkyl, heteroaryl(C$_{1-5}$)alkyl, amino, aryl, heteroaryl, hydroxy, (C$_{1-10}$)alkoxy, aryloxy, heteroaryloxy, each substituted or unsubstituted. That is, for example, the linker may comprise of the groups: —CH$_2$—, —CH$_2$—CH$_2$—, —CH$_2$—CH$_2$—O—CH$_2$—CH$_2$—, —CH$_2$—NH—CH$_2$—, —CH$_2$—CH$_2$—NH—CH$_2$—CH$_2$—, —CH$_2$—NHC(O)—CH$_2$—, —CH$_2$—C(O)NH—CH$_2$—, —CH$_2$—C(O)—CH$_2$— etc. . . . The linker chain may also comprise part of a saturated, unsaturated or aromatic ring, including monocyclic (e.g. a 1,5-cyclohexylenyl group, sugar mimetic, and sugar moiety), polycyclic and heteroaromatic rings (e.g. a 2,4-pyridinyl group etc. . . . ). As used herein, the term "linker" is a group that may be used to link interconnecting moieties such as —X—YR$_2$R$_3$, including linking a cyclic polypeptide moiety and a triazole moiety.

As used herein, where a divalent group, such as a linker, is represented by a structure -A-B—, as shown below, it is intended to also represent a group that may be attached in both possible permutations, as noted in the two structures below.

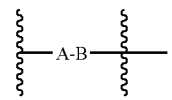

may also be

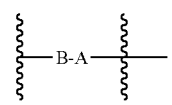

As used herein, the phrase "pharmaceutically acceptable carrier" refers to an excipient that may optionally be included in the compositions of the present application and that causes no significant adverse toxicological effects when administered in vivo.

As used herein, the term "patient" refers to any warm-blooded animal, such as a mouse, dog or human.

The compounds of the present application may be in the form of free bases or pharmaceutically acceptable acid addition salts thereof. The term "pharmaceutically-acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds for use in the present methods may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically-acceptable base addition salts of compounds of use in the present methods include metallic salts made from aluminum, calcium, lithium, magnesium, potassium, sodium and zinc or organic salts made from N, NT-dibenzylethylenediamine, chloroprocaine, choline, diethanolamine, ethylenediamine, meglumine-(N-methylglucamine) and procaine. Suitable formulations for each of these methods of administration may be found in, for example, Remington: The Science and Practice of Pharmacy, A. Gennaro, ed., 20th edition, Lippincott, Williams & Wilkins, Philadelphia, Pa.

The present invention describes, by way of non-limiting examples, the following embodiments.

One embodiment, is directed to the preparation and use of radiolabeled cyclopeptide analogs for imaging integrins (e.g., integrin $\alpha_v\beta_3$) in vivo. A series of potential integrin cyclopeptides is built using mimetics of Arg-Gly-Asp (RGD) sequence as a binding motif. Click chemistry is utilized to attach a radiolabel to cyclopeptides that contain RGD mimetic fragment and that further carry hydrophilic linkages, such as oligo- or poly-ethyleneglycol ("PEG") moieties, polar amino acid moieties, sugars or sugar mimetics, such as cyclohexane diols or polyols. One advantage is a click chemistry labeling step that is easy to perform, that is fast and provides high yields of radiolabeled products that are easy to purify. The binding affinities of the radiolabeled cyclopeptide analogs for different integrins have been determined using biochemical in vitro assays, such as cell-binding assays or surface plasmon resonance assays. The click chemistry-derived integrin ligands of the present application display surprisingly high binding affinities to the biological target, and demonstrate very favorable pharmacokinetic behavior in mice (e.g. high tumor uptake and fast clearance through predominantly renal routes).

In one embodiment of the present invention, there is provided a cyclopeptide of formula I:

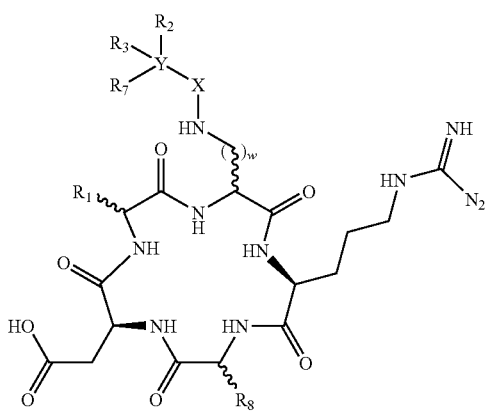

I wherein:

$R_1$ is selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted;

R7 is absent or is selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted; wherein $R_2$, $R_3$ and $R_7$ are not all H;

$R_8$ is selected from the group consisting of a side chain of a natural amino acid and a side chain of an unnatural amino acid, wherein the natural amino acid and the unnatural amino acid is either in the D or L form;

X is a 5 or 6-membered heterocycle or a linker comprising a hydrophilic moiety selected from the group consisting of hydroxyl, carbonyl, amide (—C(O)NH—), sulfonamide, sulfonate, phosphate, polar amino acid moiety, PEG moiety, sugar mimetic, and sugar moiety, or a combination thereof;

Y is a 5 or 6-membered heterocycle, or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

where at least one of X and Y, but not both X and Y is a 5 or 6-membered heterocycle; and w is 1, 2, 3, 4, or 5;

wherein any one of X, Y, $R_2$, $R_3$, and $R_7$ comprises a radionuclide selected from the group consisting of positron or gamma emitters.

As provided herein, the clause "X is a 5 or 6-membered heterocycle or a linker comprising a hydrophilic moiety selected from the group consisting of hydroxyl, carbonyl, sulfonamide, sulfonate, phosphate, polar amino acid moiety, PEG moiety, sugar mimetic, and sugar moiety, or a combination thereof" means that, for example, where X is a linker such as a $C_1$-$C_{10}$ alkylenyl group, the $C_1$-$C_{10}$ alkylenyl group may be substituted with a hydroxyl group; or X may be a linker that comprises a sugar mimetic as part of the linker; or X may be a $C_1$-$C_{10}$ alkylenyl group that comprises a carbonyl group in the linker, the $C_1$-$C_{10}$ alkylenyl group may be substituted with a hydroxyl group and comprises an adjacent or non-adjacent sugar mimetic as part of the $C_1$-$C_{10}$ alkylenyl group or the $C_1$-$C_{10}$ alkylenyl group may be substituted with a sugar mimetic (as a substituent), and the various combinations and permutations thereof.

In certain variations of each of the embodiments of the present invention, the 5-membered heterocycle is a substituted 1,2,3-triazolyl group as disclosed herein. In another variation of each of the embodiment of the compounds of the present invention, R8 is $C_1$-$C_5$ alkyl or hydroxyl-$C_1$-$C_5$ alkyl, or specifically, $R_8$ is methyl or hydroxymethyl.

In one embodiment of any of the aspects disclosed herein, Y is a 5 or 6-membered heterocycle; and X is a linker either comprising a sugar mimetic selected from the group consisting of a 4 to 6-membered carbocycle substituted with at least one hydroxyl group and a 5- to 6-membered heterocycle substituted with at least one hydroxyl group or comprising a sugar moiety selected from the group consisting of glucose and galactose. In another embodiment, X is a linker comprising a sugar mimetic selected from the group consisting of a hydroxylated cyclohexanyl group, a hydroxylated cyclopentanyl group, a hydroxylated pyrrolidinyl group, and a hydroxylated piperidinyl group. In yet another embodiment, Y is a 5 or 6-membered heterocycle; X is selected from the group consisting of:

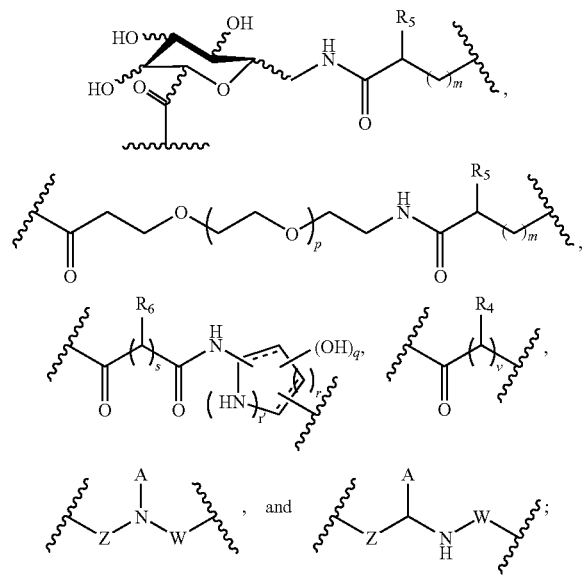

where Z is selected from the group consisting of:

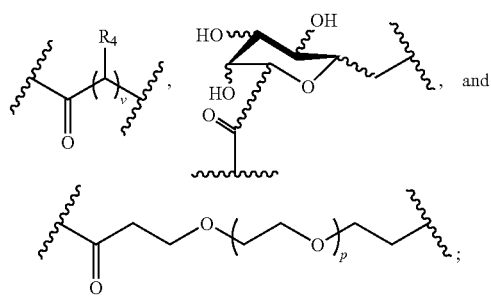

W is selected from the group consisting of:

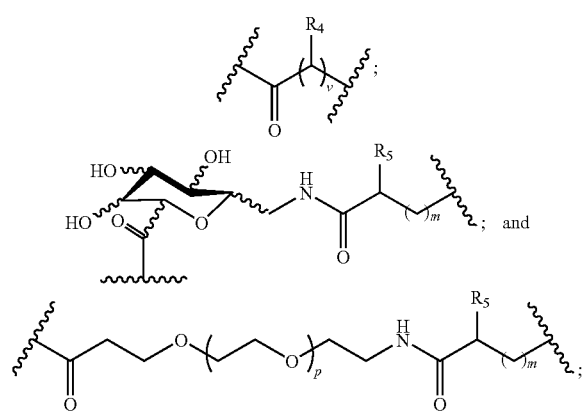

A is selected from the group consisting of:

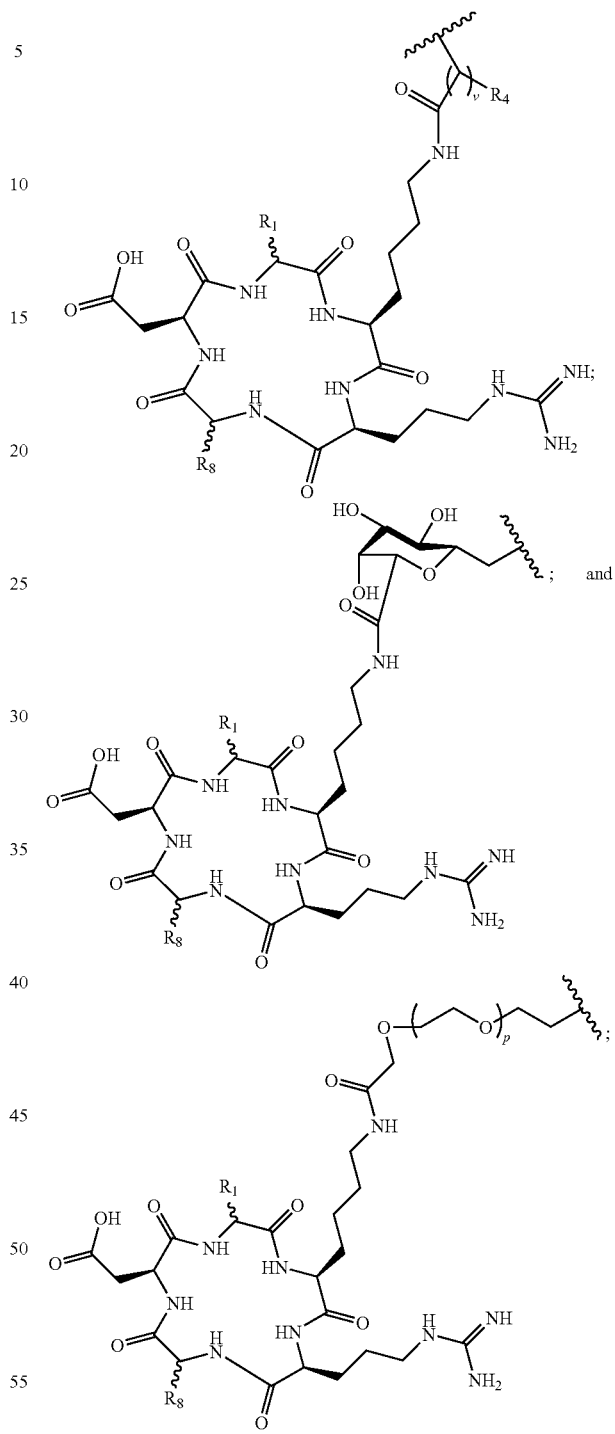

each R1 is independently selected from the group consisting of a side chain of a natural amino acid and a side chain of an unnatural amino acid, wherein the natural amino acid and the unnatural amino acid is either in the D or L form;

each R4 is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

R5 is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted;

each R6 is independently selected from the group consisting of —OH, $C_1$-$C_6$ alkyl, $C_2$-$C_6$ alkenyl, $C_2$-$C_6$ alkynyl, $C_1$-$C_6$ alkyloxy, aryl-($C_1$-$C_6$ alkylene)-, hydroxy-$C_1$-$C_6$-alkyl, and $C_1$-$C_6$-alkoxy-$C_1$-$C_6$-alkyl, wherein the alkyl, alkenyl, alkynyl, alkyloxy, and aryl-alkylene groups are each optionally substituted;

each $R_8$ is independently selected from the group consisting of a side chain of a natural amino acid and a side chain of an unnatural amino acid, wherein the natural amino acid and the unnatural amino acid is either in the D or L form;

each v is 0, 1, 2, 3, or 4; m is 0, 1, 2, 3 or 4; p is an integer between 1 and 110; q is 1, 2, 3 or 4; r is 1, 2 or 3; r' is 0 or 1; s is 1, 2, 3 or 4; and the radionuclide is selected from the group consisting of $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I, $^{131}$I, $^{99}$Tc, $^{75}$Br, $^{153}$Gd and $^{32}$P; wherein the configuration of the chiral centers may be R or S or mixtures thereof.

In yet another embodiment, $R_1$ is a side chain of a natural amino acid; $R_8$ is a side chain of a natural amino acid; $R_7$ is absent;

X is

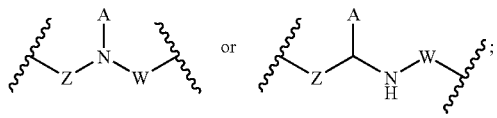

Y is 1,2,3-triazolyl; and R2 and R3 are each independently selected from the group consisting of $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein R2 and R3 are not both H; and either $R_2$ or $R_3$, or both $R_2$ and $R_3$ comprise a radionuclide selected from the group consisting of $^{11}$C, $^{13}$N, $^{15}$O, $^{18}$F, $^{75}$Br, $^{124}$I, $^{125}$I and $^{131}$I. In one variation, Z is

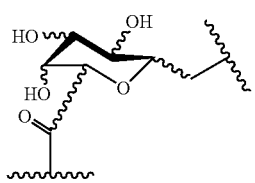

and A is

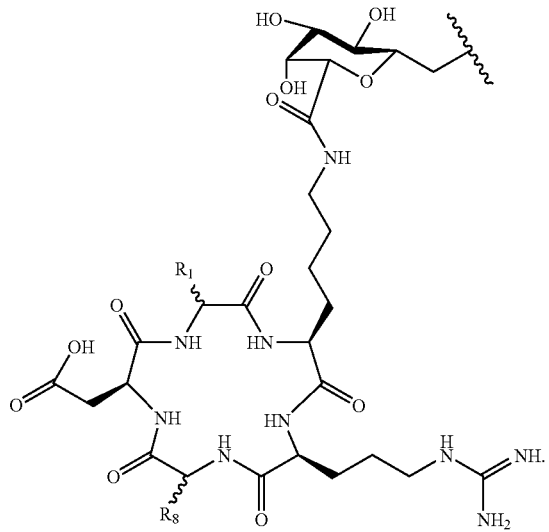

In another variation, Z is

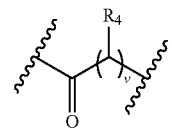

and A is

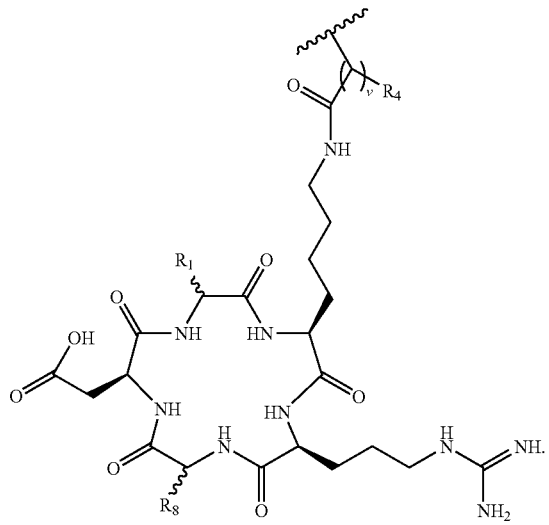

In yet another variation, Z is

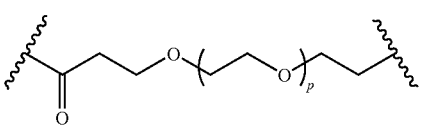

and A is

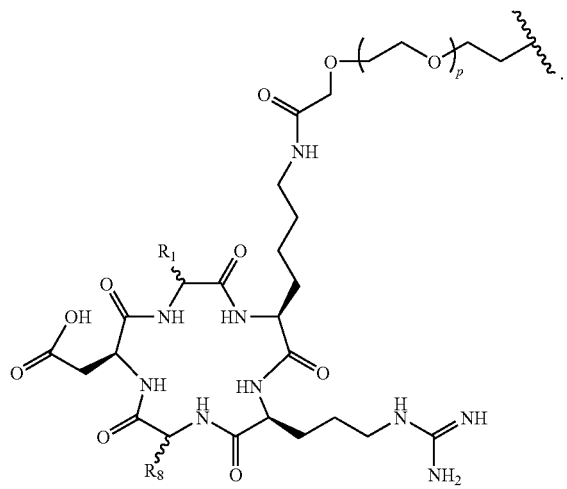

One aspect of the present application is a cyclopeptide of formula II:

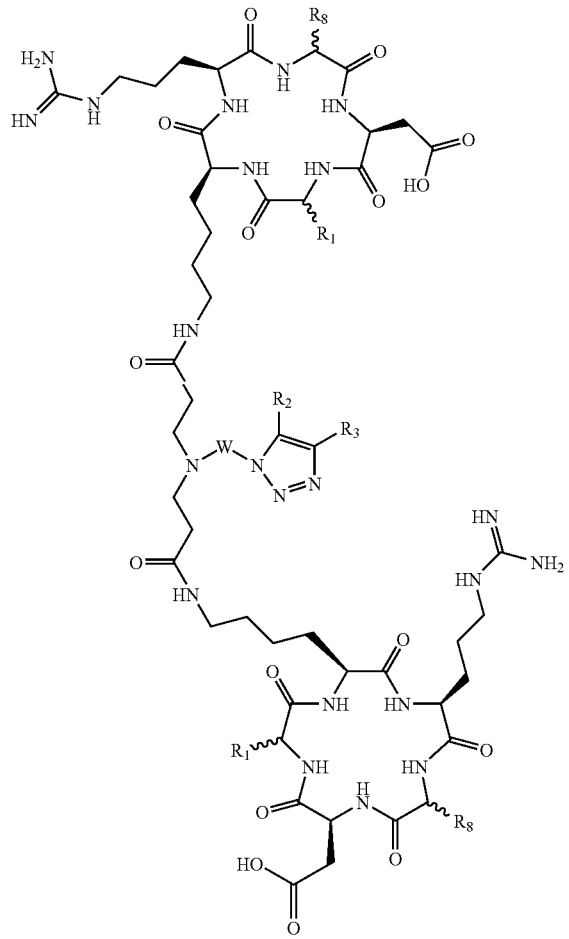

II wherein each R1 is independently selected from the group consisting of a side chain of a natural amino acid and a side chain of an unnatural amino acid, wherein the natural amino acid and the unnatural amino acid is either in the D or L form; $R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-(C1-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}$C, $^{13}$N, $^{15}$O, $^{18}$F, $^{75}$Br, $^{124}$I, $^{125}$I and $^{131}$I;

W is

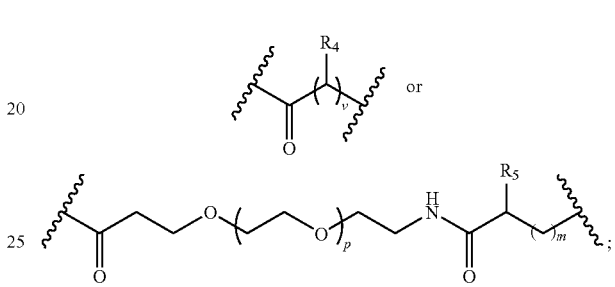

where p is an integer between 0 and 15; v is 0, 1, 2, or 3; m is 0, 1 or 2; each R4 is independently selected from the group consisting of —H, $C_1$-$C_6$ alkyl, $C_2$-$C_6$ alkenyl, and $C_2$-$C_6$ alkynyl, wherein the alkyl, alkenyl and alkynyl groups are each optionally substituted; $R_5$ is selected from the group consisting of —H, $C_1$-$C_6$ alkyl, $C_2$-$C_6$ alkenyl, and C2-C6 alkynyl, wherein the alkyl, alkenyl and alkynyl groups are each optionally substituted, each R8 is independently selected from the group consisting of a side chain of a natural amino acid and a side chain of an unnatural amino acid, wherein the natural amino acid and the unnatural amino acid is either in the D or L form; and wherein the configuration of the chiral center that is substituted with the $R_5$ substituent may be R or S or mixtures thereof.

In yet another embodiment, W is

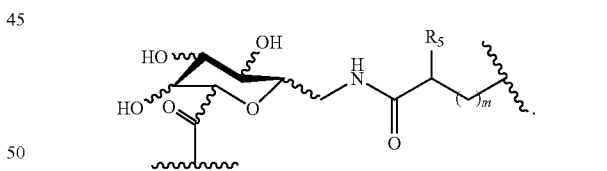

In one embodiment of the any of the disclosed aspects, each $R_1$ is benzyl; $R_2$ is H; $R^3$ is an optionally substituted $C^1$-$C^6$ alkyl comprising a radionuclide selected from the group consisting of $^{11}$C, $^{13}$N, $^{15}$O, $^{18}$F, $^{75}$Br, $^{124}$I, $^{125}$I and $^{131}$I; and W is

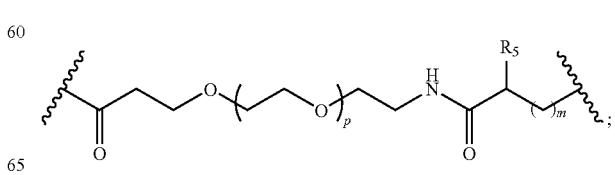

where p is 0, 1, 2, 3, 4 or 5.

Another aspect of the present application is a cyclopeptide of formula III:

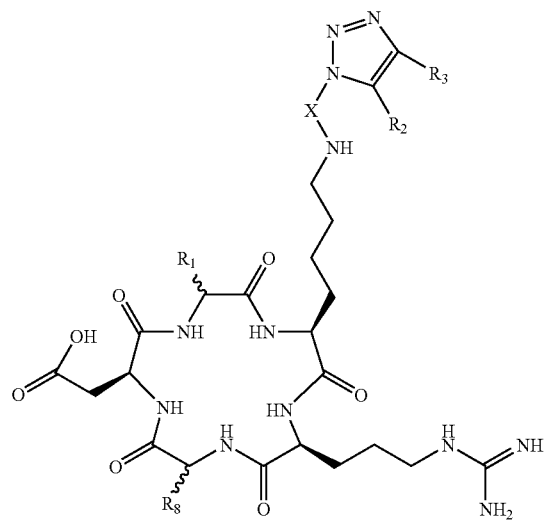

III wherein R1 is selected from the group consisting of a side chain of a natural amino acid and a side chain of an unnatural amino acid, wherein the natural amino acid and the unnatural amino acid is either in the D or L form; $R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted; wherein $R_2$ and $R_3$ are not both H; and either $R_2$ or $R_3$, or both $R_2$ and $R_3$ comprise a radionuclide selected from the group consisting of positron or gamma emitters; $R_8$ is selected from the group consisting of a side chain of a natural amino acid and a side chain of an unnatural amino acid, wherein the natural amino acid and the unnatural amino acid is either in the D or L form; and X is a linker comprising a hydrophilic moiety selected from the group consisting of hydroxyl, carbonyl, amide (—C(O)NH—), sulfonamide, sulfonate, phosphate, polar amino acid moiety, PEG moiety, sugar mimetic and sugar moiety, or a combination thereof.

In one variation any of the embodiments and aspects disclosed herein, $R_1$ is a side chain of a natural amino acid; $R_8$ is a side chain of a natural amino acid; $R_2$ is hydrogen; and $R_3$ comprises a radionuclide selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$. In another variation, $R_1$ is benzyl; $R_8$ is a side chain of a natural amino acid; and $R_3$ comprises a radionuclide selected from the group consisting of $^{11}C$, $^{13}N$, $^{15}O$, $^{18}F$, $^{124}I$, $^{125}I$, $^{131}I$ and a $^{75}Br$. In yet another embodiment, $R_1$ is a side chain of a natural amino acid; X is selected from the group consisting of:

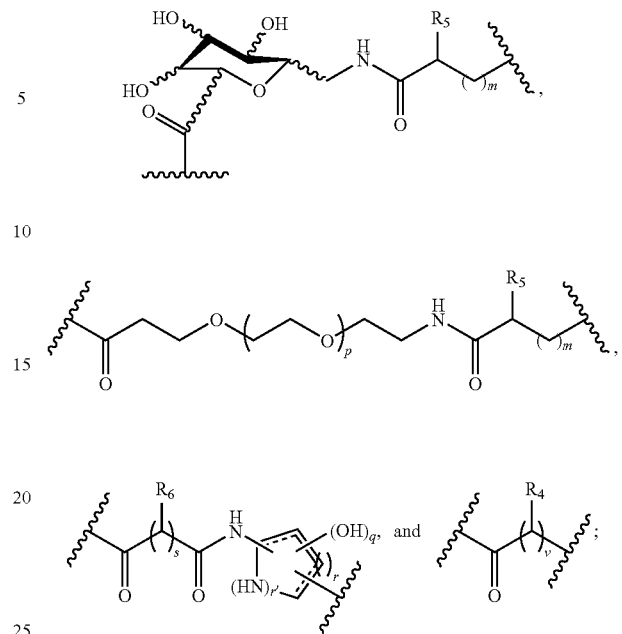

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle and heterocycle groups are each optionally substituted;

each R6 is independently selected from the group consisting of —OH, $C_1$-$C_6$ alkyl, $C_2$-$C_6$ alkenyl, $C_2$-$C_6$ alkynyl, $C_1$-$C_6$ alkyloxy, aryl-($C_1$-$C_6$ alkylene)-, hydroxy-$C_1$-$C_6$-alkyl, and $C_1$-$C_6$-alkoxy-$C_1$-$C_6$-alkyl, wherein the alkyl, alkenyl, alkynyl, alkyloxy, and aryl-alkylene groups are each optionally substituted;

R8 is a side chain of a natural amino acid;

v is 0, 1, 2, 3, or 4; m is 0, 1, 2, 3 or 4; p is an integer between 1 and 110; q is 1, 2, 3 or 4; r is 1, 2 or 3; r' is 0 or 1; s is 1, 2, 3 or 4; and the radionuclide is selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$; where the configuration of the chiral centers may be R or S or mixtures thereof.

In another embodiment, $R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{75}Br$, $^{124}I$, $^{125}I$ and $^{131}I$; X is

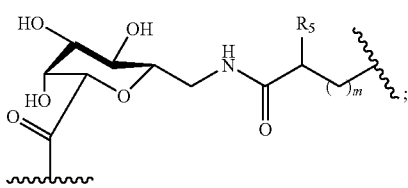

where $R_5$ is selected from the group consisting of —H, $C_1$-$C_6$ alkyl, $C_2$-$C_6$ alkenyl, and $C_2$-$C_6$ alkynyl, wherein the alkyl, alkenyl and alkynyl groups are each optionally substituted and wherein the configuration of the chiral center that is substituted with the $R_5$ substituent may be R or S or mixtures thereof; and m is 0, 1 or 2.

In yet another embodiment, $R_2$ is hydrogen; $R_3$ is selected from the group consisting of $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted; wherein $R_3$ comprises a radionuclide selected from the group consisting of $^{11}$C, $^{13}$N, $^{15}$O and $^{18}$F; $R_5$ is hydrogen; and m is 0.

In a further embodiment, $R_2$ and $R_3$ are each independently selected from the group consisting of $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted; wherein $R_2$ and $R_3$ are not both H; and either $R_2$ or $R_3$, or both $R_2$ and $R_3$ comprise a radionuclide selected from the group consisting of $^{11}$C, $^{13}$N, $^{15}$O, $^{18}$F, $^{75}$Br, $^{124}$I, $^{125}$I, and $^{131}$I;

X is 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted, and $R_3$ comprises a radionuclide selected from the group consisting of $^{11}$C, $^{13}$N, $^{15}$O, and $^{18}$F; $R_5$ is hydrogen; m is 0; and p is an integer between 1 and 15.

In another embodiment of any of the aspects disclosed herein, X is

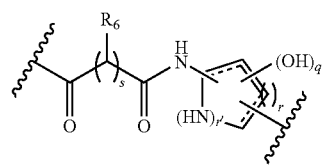

where each $R_6$ is independently selected from the group consisting of —H, —OH, $C_1$-$C_6$ alkyl, $C_2$-$C_6$ alkenyl, $C_1$-$C_6$ alkyloxy, hydroxy-$C_1$-$C_6$-alkyl, and $C_1$-$C_6$-alkoxy-$C_1$-$C_6$-alkyl, wherein the alkyl, alkenyl, and alkyloxy groups are each optionally substituted; q is 2, 3 or 4; r is 2 or 3; r' is 0; and s is 1 or 2.

In yet another embodiment of the present application, X is

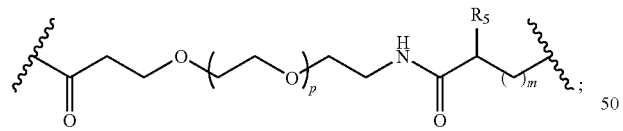

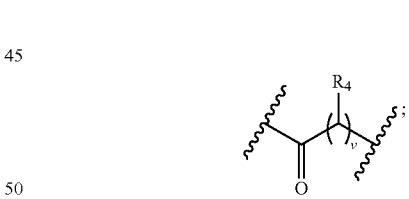

where $R_5$ is selected from the group consisting of —H, $C_1$-$C_6$ alkyl, $C_2$-$C_6$ alkenyl, and $C_2$-$C_6$ alkynyl, wherein the alkyl, alkenyl and alkynyl groups are each optionally substituted and wherein the configuration of the chiral center that is substituted with the $R_5$ substituent may be R or S or mixtures thereof; m is 0, 1, or 2; and p is an integer between 1 and 90.

In still another embodiment, $R_2$ is hydrogen; $R_3$ is selected from the group consisting of $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted; and v is 1, 2, 3, or 4. In one variation, each $R_4$ is independently selected from the group consisting of —H, $C_1$-$C_6$ alkyl, $C_2$-$C_6$ alkenyl, $C_2$-$C_6$ alkynyl, and a PEG moiety, wherein the alkyl, alkenyl, and alkynyl groups are each optionally substituted.

One aspect of the present application is a radiolabeled cyclopeptide of formula IV:

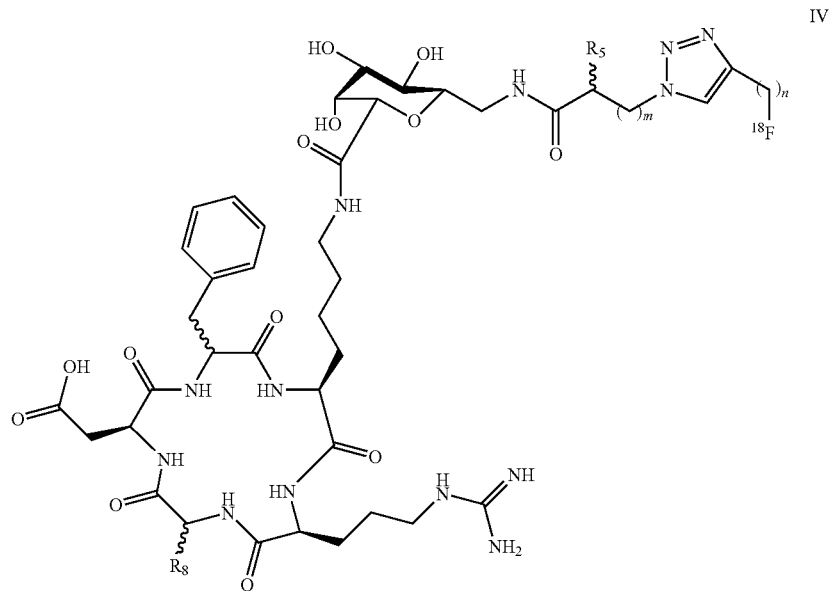

wherein: $R_8$ is selected from the group consisting of a side chain of a natural amino acid and a side chain of an unnatural amino acid, wherein the natural amino acid and the unnatural amino acid is either in the D or L form; $R_5$ is selected from the group consisting of H, $C_1$-$C_6$ alkyl, $C_2$-$C_6$ alkenyl, $C_2$-$C_6$ alkynyl, $C_1$-$C_6$ alkyloxy, aryl, —($C_1$-$C_6$ alkylene)-aryl, 3- to 7-membered carbocycle, 3- to 7-membered heterocycle, hydroxy-$C_1$-$C_6$-alkyl, and $C_1$-$C_6$-alkoxy-$C_1$-$C_6$-alkyl; wherein the alkyl, alkenyl, alkynyl, alkyloxy, aryl, carbocycle and heterocycle groups are each optionally substituted; wherein the chiral centers attached to ⁓ bonds are R or S or mixtures thereof; m is 0, 1, 2, 3 or 4; and n is 1, 2, 3, 4 or 5.

In one embodiment, $R_5$ is selected from the group consisting of H, $C_1$-$C_4$ alkyl, $C_2$-$C_4$ alkenyl, and $C_2$-$C_4$ alkynyl, wherein the alkyl, alkenyl and alkynyl groups are each optionally substituted; wherein the chiral center in the cyclic peptide is R configured and the chiral center bearing the $R_5$ residue is R or S or mixtures thereof; m is 0, 1 or 2; and n is 1, 2, 3 or 4. In another embodiment, $R_5$ is selected from the group consisting of —H, and an optionally substituted $C_1$-$C_4$ alkyl; m is 0 or 1; and n is 2, 3 or 4.

Another aspect of the present application is a radiolabeled cyclopeptide selected from the group consisting of:

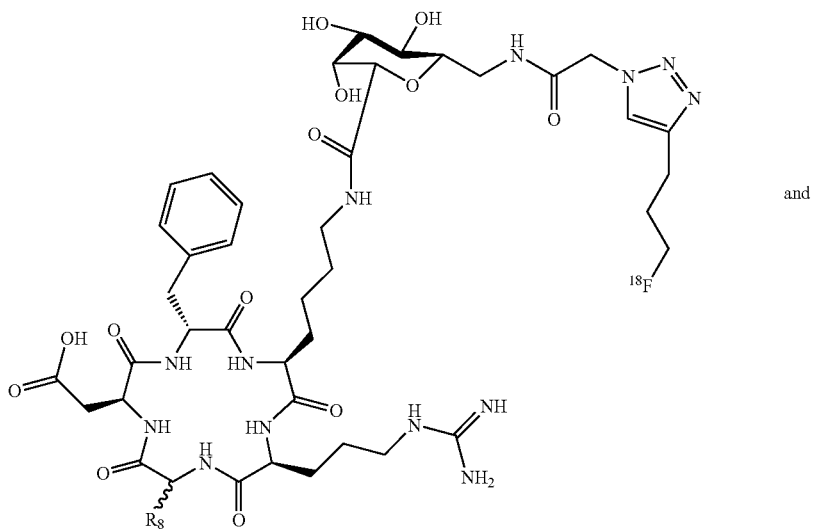

and

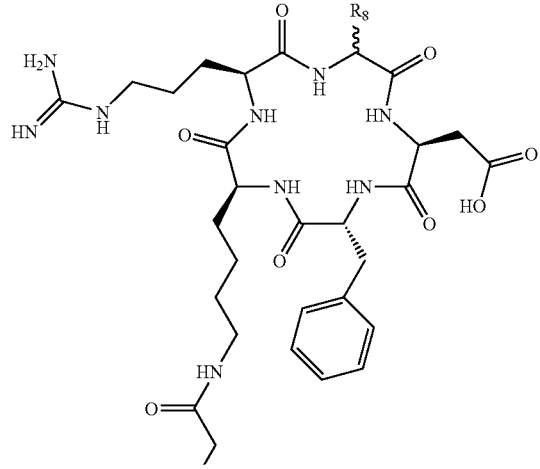
-continued
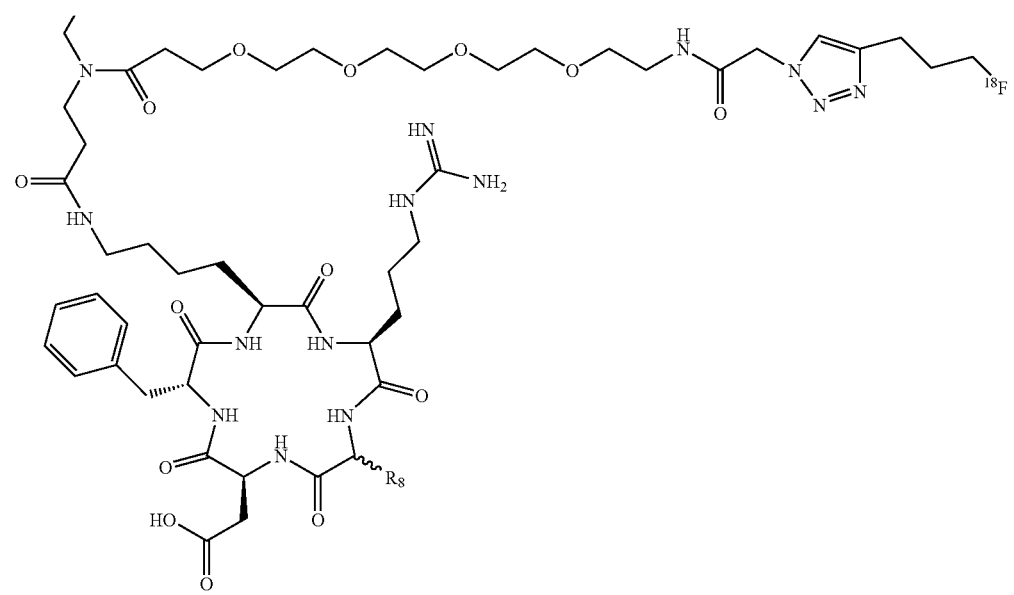
Yet another aspect of the present application is a pharmaceutical composition comprising a radiolabeled cyclopeptide of the formula I, formula II and formula II as defined herein.

Still another aspect of the present application is a pharmaceutical composition comprising a radiolabeled cyclopeptide selected from the group consisting of:
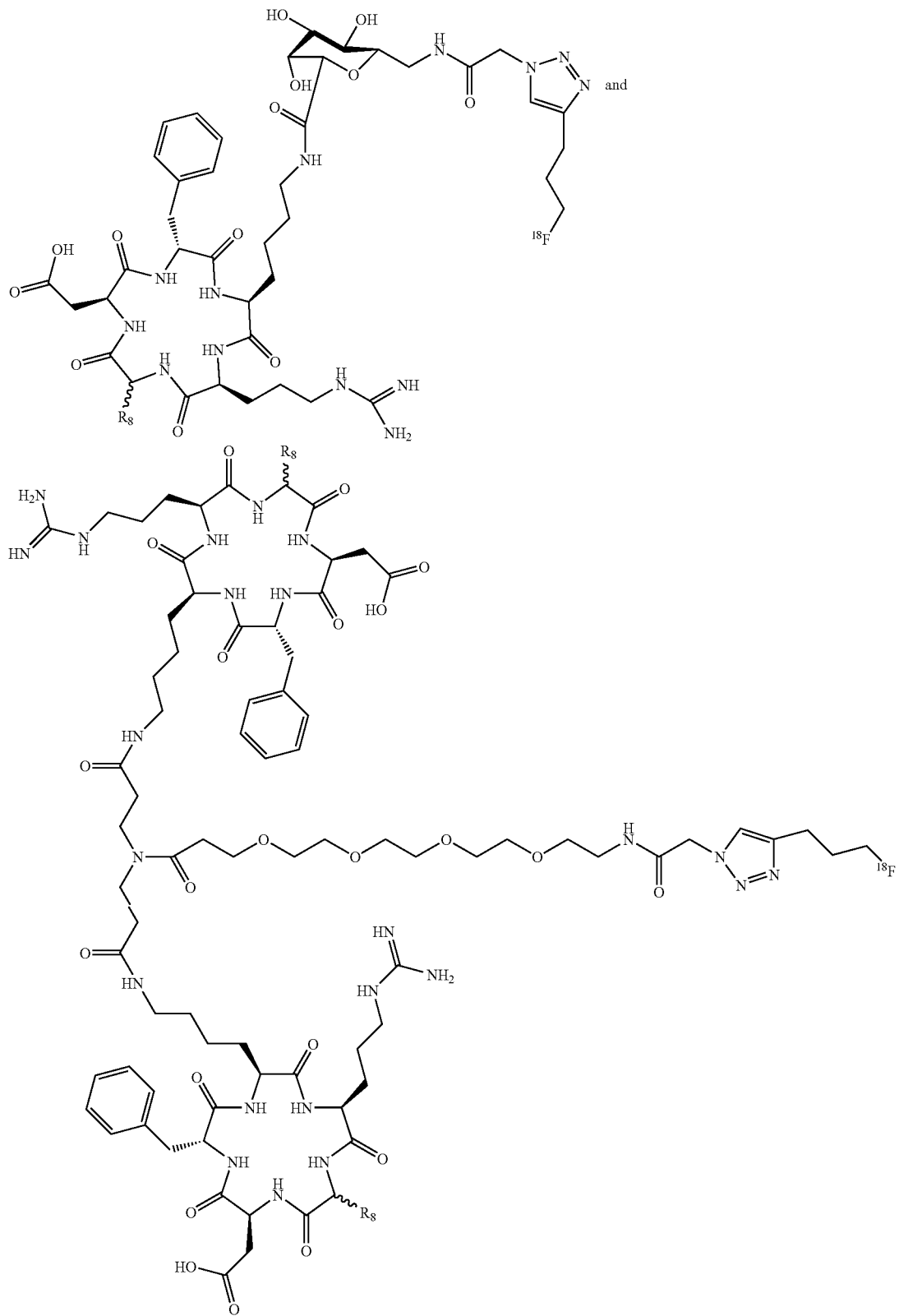
and a pharmaceutically acceptable carrier.

One aspect of the present invention is a method of monitoring the level of integrin $\alpha_v\beta_3$ or visualizing integrin $\alpha_v\beta_3$ expression within a body of a patient, the method comprising: (a) administering to the patient a radiolabeled cyclopeptide; and (b) employing a nuclear imaging technique selected from the group consisting of positron emission tomography (PET) and single photon emission computed tomography (SPECT) for monitoring or visualizing a distribution of the radiolabeled cyclopeptide within the body or within a portion thereof; wherein the radiolabeled cyclopeptide is of formula I, as defined herein.

Another aspect of the present invention is a method of monitoring the level of integrin $\alpha_v\beta_3$ or visualizing integrin $\alpha_v\beta_3$ expression within a body of a patient, the method comprising: (a) administering to the patient a radiolabeled cyclopeptide; and (b) employing a nuclear imaging technique selected from the group consisting of positron emission tomography (PET) and single photon emission computed tomography (SPECT) for monitoring or visualizing a distribution of the radiolabeled cyclopeptide within the body or within a portion thereof; wherein the radiolabeled cyclopeptide is of formula II or formula III:

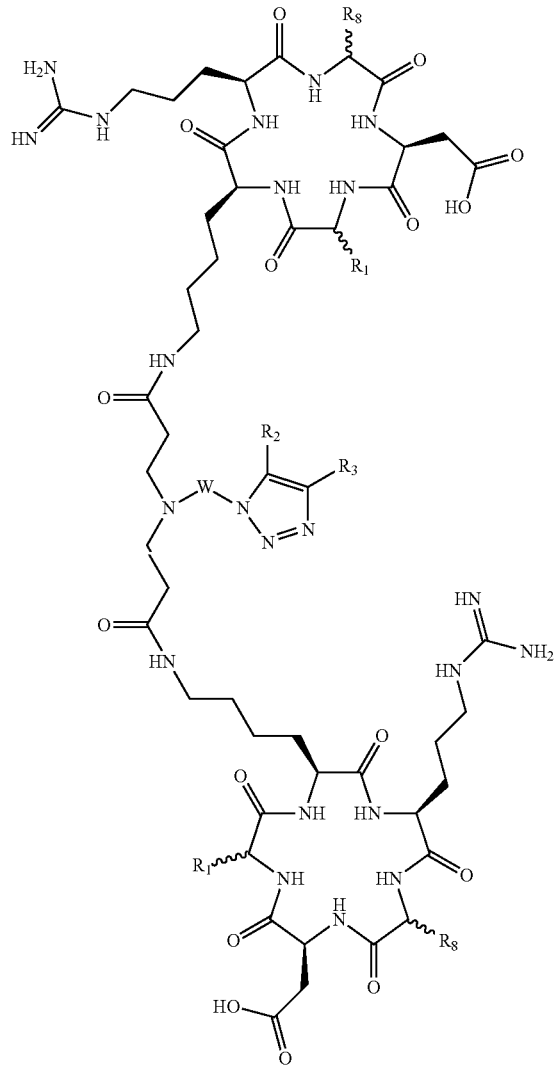

II

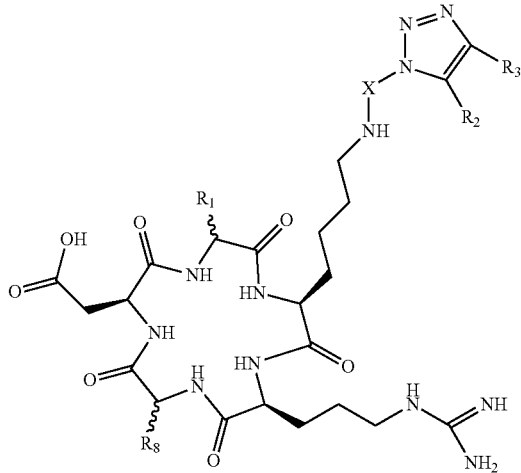

III wherein each $R_1$ is independently selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$;

each of X and W is selected from the group consisting of:

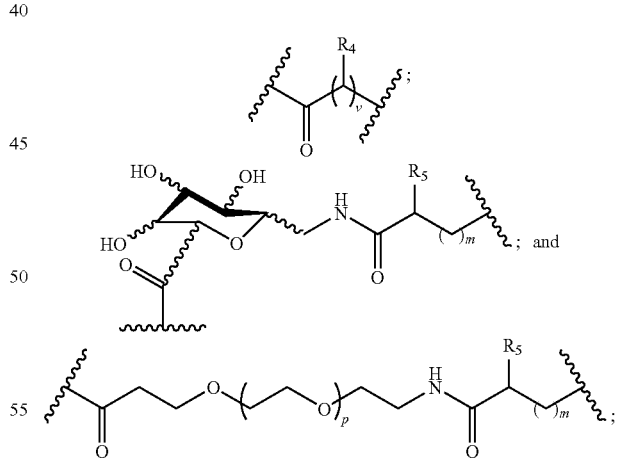

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted;

each $R_8$ is independently selected from the group consisting of a side chain of a natural amino acid and a side chain of an unnatural amino acid, wherein the natural amino acid and the unnatural amino acid is either in the D or L form;

wherein the configuration of the chiral centers may be R or S or mixtures thereof; v is 0, 1, 2, 3, or 4; m is 0, 1, 2, 3 or 4; and p is an integer between 1 and 25.

Yet another aspect of the present invention is a method of monitoring the level of integrin $\alpha_v\beta_3$ or visualizing integrin $\alpha_v\beta_3$ expression within a body of a patient, the method comprising: (a) administering to the patient a radiolabeled cyclopeptide; and (b) employing a nuclear imaging technique selected from the group consisting of positron emission tomography (PET) and single photon emission computed tomography (SPECT) for monitoring or visualizing a distribution of the radiolabeled cyclopeptide within the body or within a portion thereof; wherein the radiolabeled cyclopeptide is selected from the group consisting of:

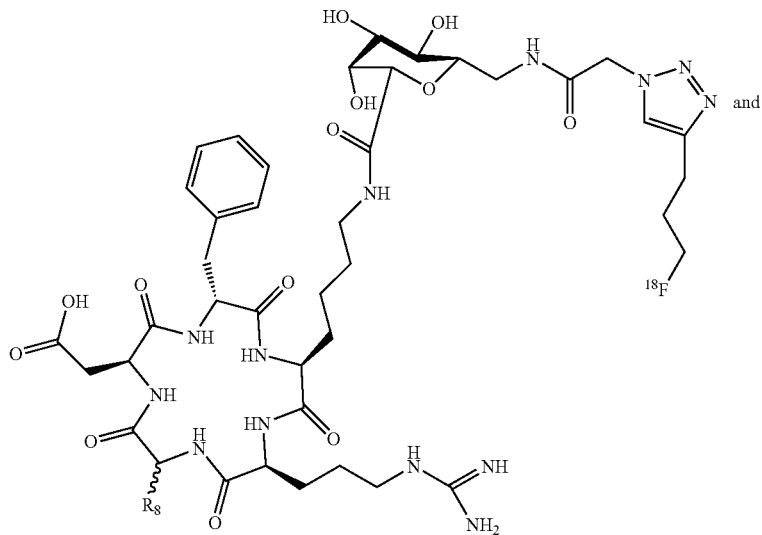

and

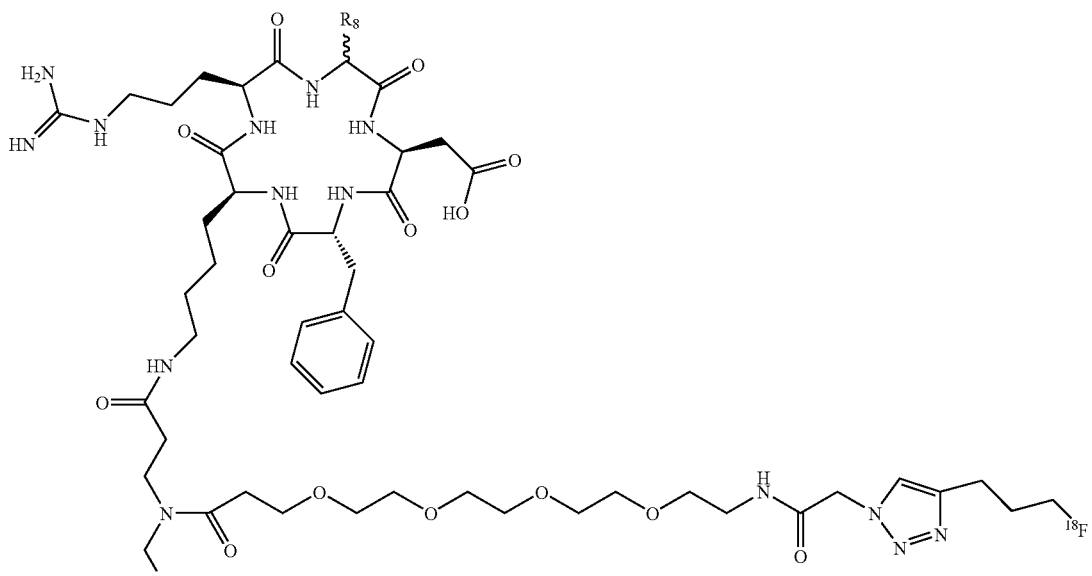

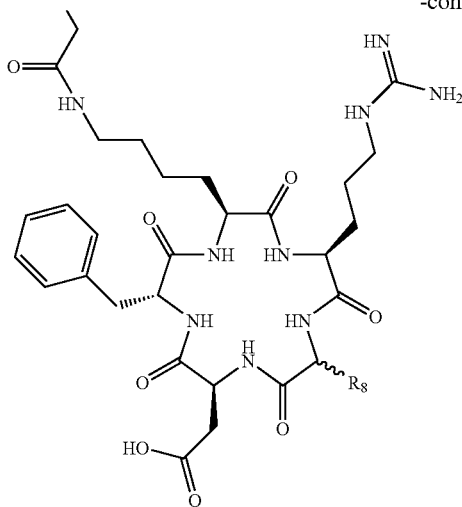

wherein each $R_8$ is selected from the group consisting of a side chain of a natural amino acid and a side chain of an unnatural amino acid, wherein the natural amino acid and the unnatural amino acid is either in the D or L form.

Yet another aspect of the present invention is a cyclic peptide selected from the group consisting of:

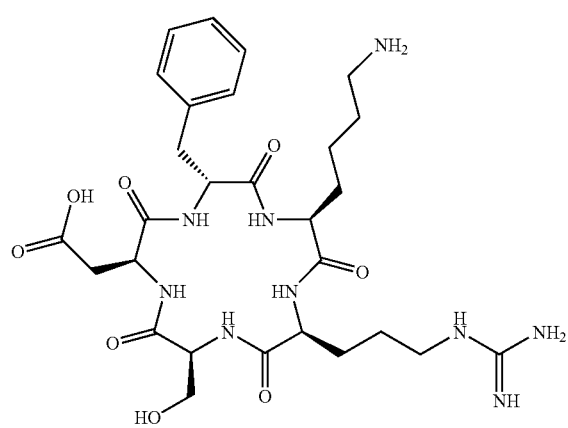
Cyclo (Arg-Ser-Asp-D-Phe-Lys)

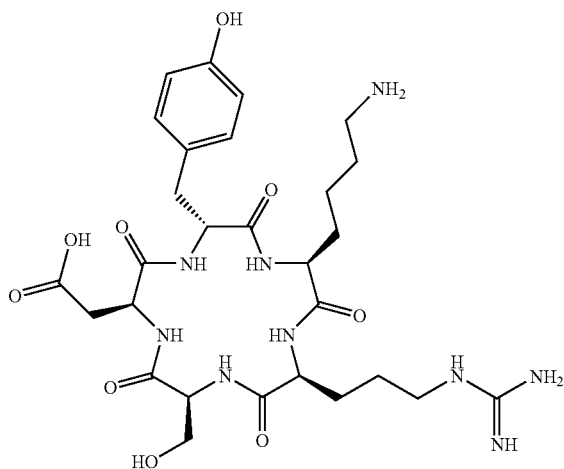
Cyclo (Arg-Ser-Asp-D-Tyr-Lys)

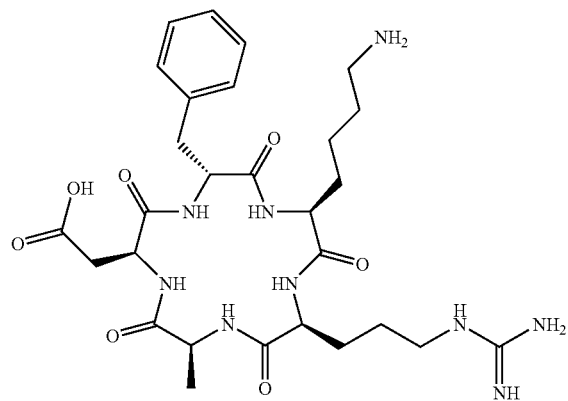
Cyclo (Arg-Ala-Asp-D-Phe-Lys)

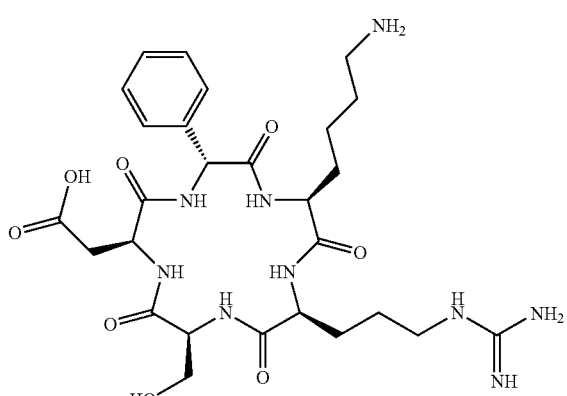
Cyclo (Arg-Ser-Asp-D-Phg-Lys)

-continued
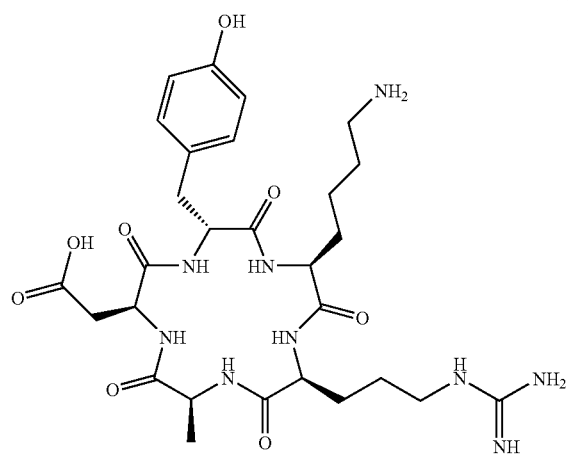
Cyclo (Arg-Ala-Asp-D-Tyr-Lys)
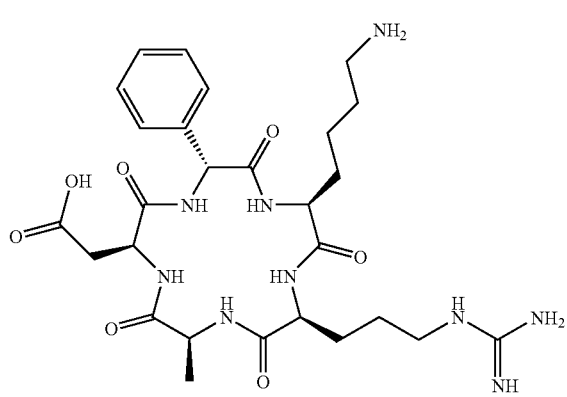
Cyclo (Arg-Ala-Asp-D-Phg-Lys)
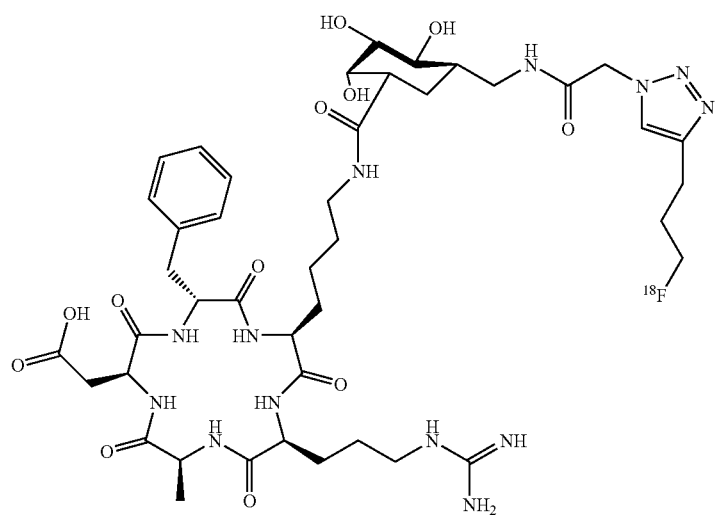
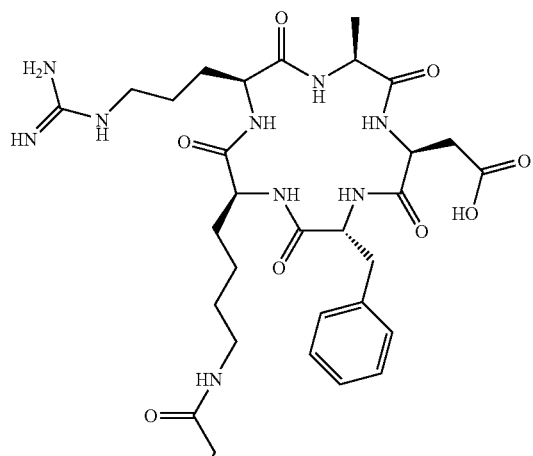

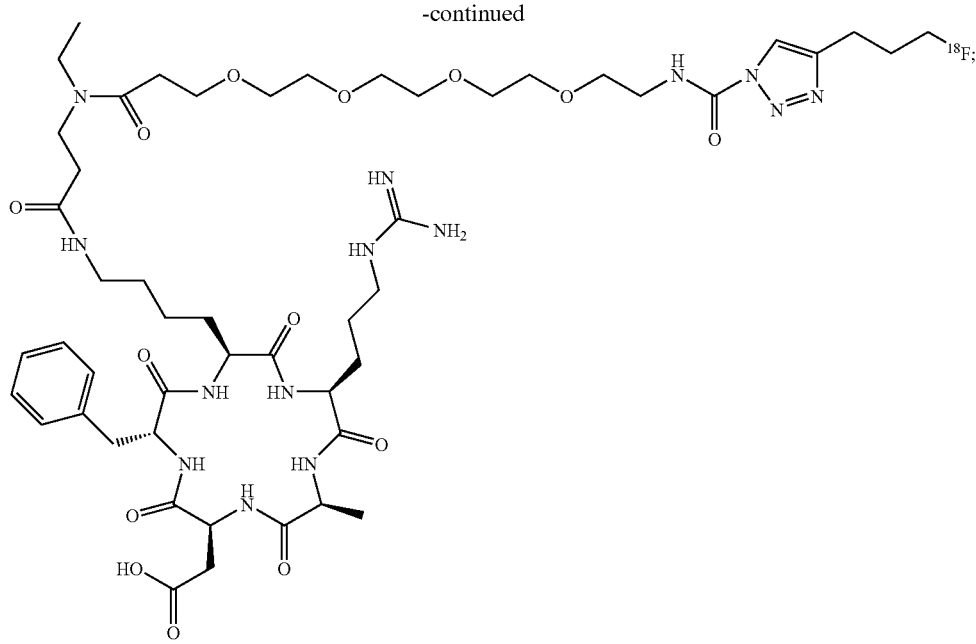

and a pharmaceutically acceptable carrier.

A still further aspect of the present invention is a method for imaging of blood vessel growth in solid tumors based on expression of integrin $\alpha_v\beta_3$ within the body of a patient, the method comprising: (a) administering to the patient a radiolabeled cyclopeptide; (b) employing a nuclear imaging technique selected from the group consisting of positron emission tomography (PET) and single photon emission computed tomography (SPECT) for imaging a distribution of the radiolabeled cyclopeptide within the body or within a portion thereof; and c) correlating the distribution of the radiolabeled cyclopeptide to the growth of blood vessels in solid tumors, wherein the radiolabeled cyclopeptide is of formula I as defined herein.

Yet another aspect of the present invention is a method for imaging of blood vessel growth in solid tumors based on expression of integrin $\alpha_v\beta_3$ within the body of a patient, the method comprising: (a) administering to the patient a radiolabeled cyclopeptide; (b) employing a nuclear imaging technique selected from the group consisting of positron emission tomography (PET) and single photon emission computed tomography (SPECT) for imaging a distribution of the radiolabeled cyclopeptide within the body or within a portion thereof; and c) correlating the distribution of the radiolabeled cyclopeptide to the growth of blood vessels in solid tumors, wherein the radiolabeled cyclopeptide is of formula II or formula III as defined herein.

Yet another aspect of the present invention is a method for imaging of blood vessel growth in solid tumors based on expression of integrin $\alpha_v\beta_3$ within the body of a patient, the method comprising: (a) administering to the patient a radiolabeled cyclopeptide; (b) employing a nuclear imaging technique selected from the group consisting of positron emission tomography (PET) and single photon emission computed tomography (SPECT) for imaging a distribution of the radiolabeled cyclopeptide within the body or within a portion thereof; and c) correlating the distribution of the radiolabeled cyclopeptide to the growth of blood vessels in solid tumors, wherein the radiolabeled cyclopeptide is selected from the group consisting of:

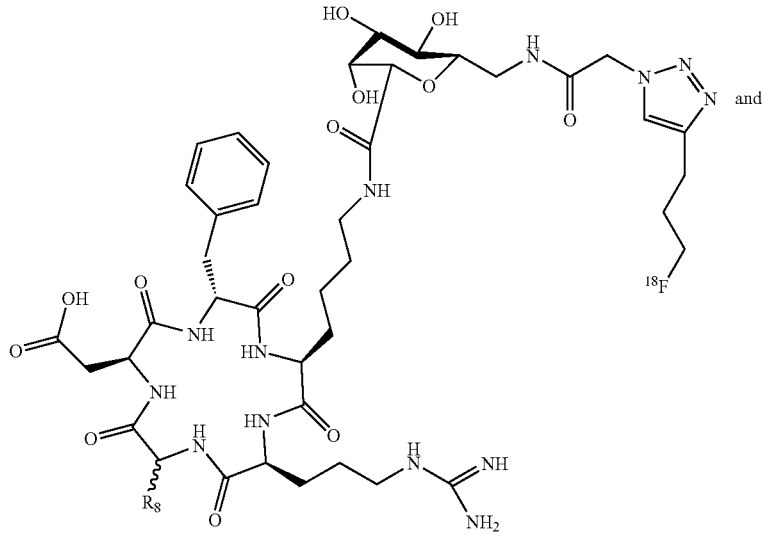

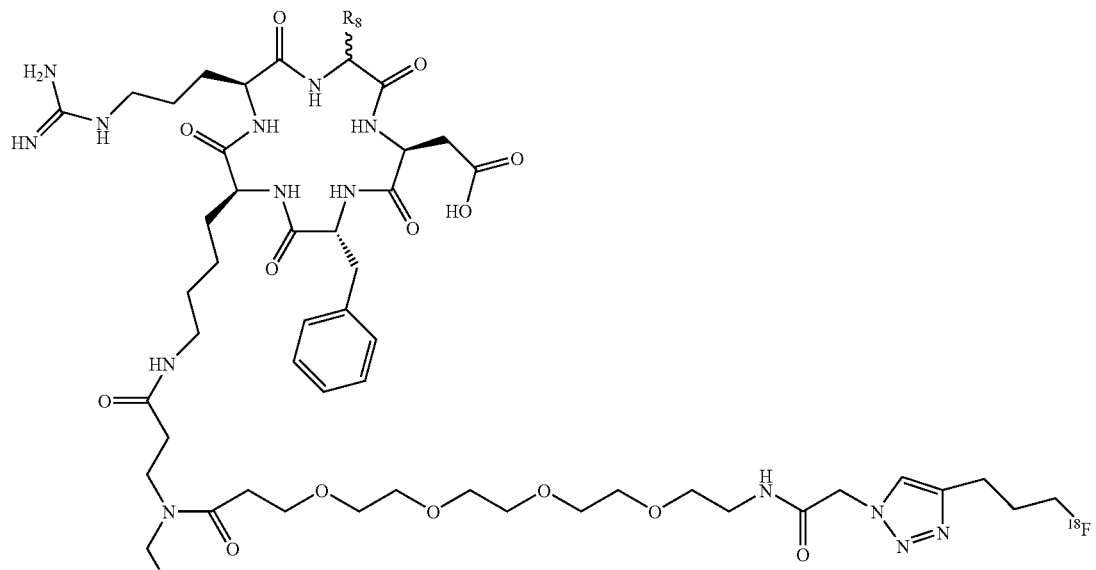
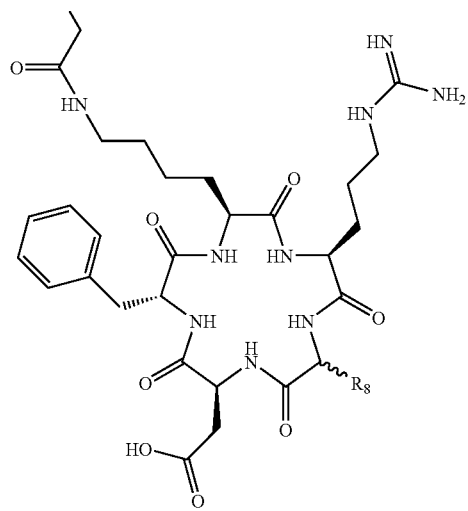

One aspect of the present invention is a compound of formula V:

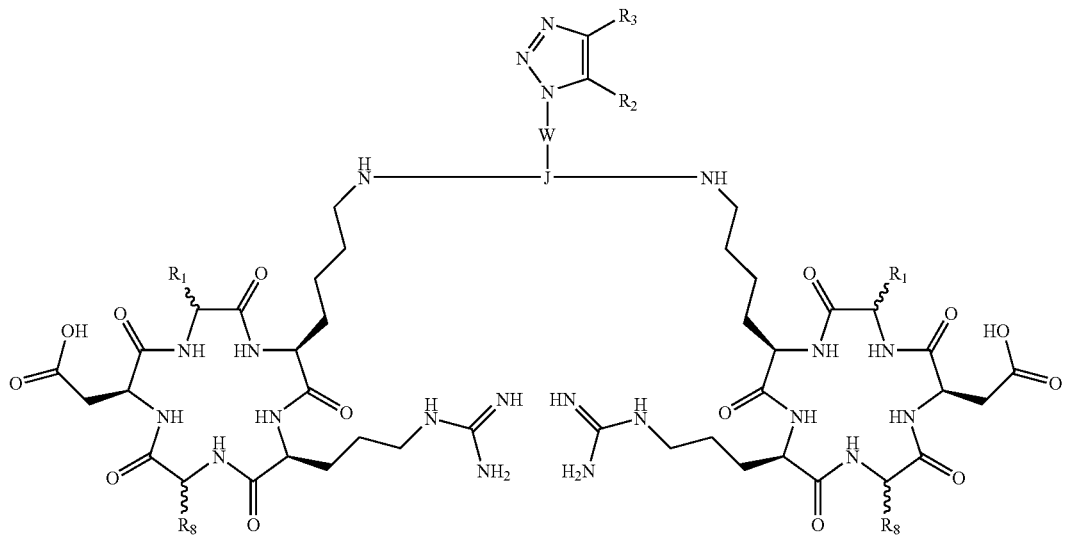

wherein each $R_1$ is independently selected from the group consisting of a side chain of a natural amino acid and a side chain of an unnatural amino acid, wherein the natural amino acid and the unnatural amino acid is either in the D or L form; each $R_8$ is independently selected from the group consisting of a side chain of a natural amino acid and a side chain of an unnatural amino acid, wherein the natural amino acid and the unnatural amino acid is either in the D or L form; $R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted; wherein $R_2$ and $R_3$ are not both H; and either $R_2$ or $R_3$, or both $R_2$ and $R_3$ comprise a radionuclide selected from the group consisting of positron or gamma emitters; W is a linker comprising zero, one or more moieties selected from the group consisting of hydroxyl, carbonyl, sulfonamide, sulfonate, phosphate, polar amino acid moiety, PEG moiety, sugar mimetic, and a sugar moiety; J is a linker comprising a moiety selected from the group consisting of $C_1$-$C_6$ alkyl, —$C_1$-$C_6$ alkenyl, —$C_1$-$C_6$ alkynyl, aryl, aryl-($C_1$-$C_6$ alkylene)-, 3- to 7-membered carbocycle, 3- to 7-membered heterocycle, and natural amino acids wherein the alkyl, alkenyl, alkynyl, aryl, carbocycle, heterocycle groups are each optionally substituted. In one aspect, the radionuclide is selected from the group consisting of $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I, $^{131}$I, $^{99}$Tc, $^{75}$Br, $^{153}$Gd, and $^{32}$P; W is selected from the group consisting of

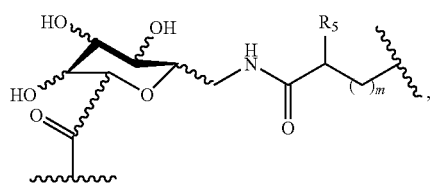

-continued

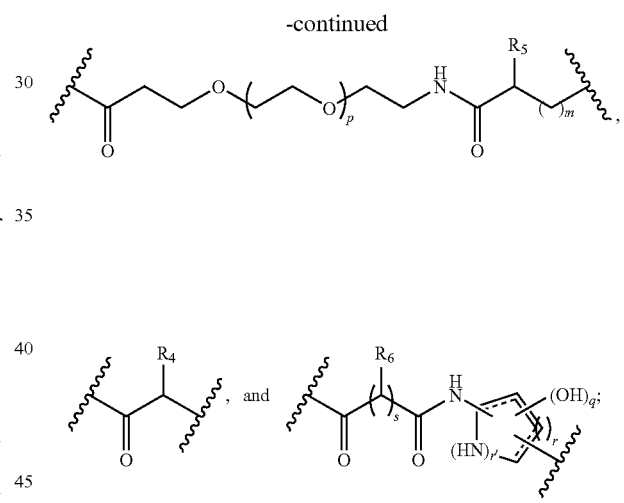

where $R_4$ is independently —H, —$C_1$-$C_6$ alkyl, $C_1$-$C_6$ alkenyl, $C_1$-$C_6$ alkynyl, $C_1$-$C_6$ alkyloxy, aryl, aryl-($C_1$-$C_6$ alkylene)-, $C_3$-$C_7$ carbocycle, 3- to 7-membered heterocycle, hydroxy-$C_1$-$C_6$-alkyl, $C_1$-$C_6$-alkoxy-$C_1$-$C_6$-alkyl, and a PEG moiety, $R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle and heterocycle groups are each optionally substituted; each $R_6$ is independently selected from the group consisting of —H, —OH, $C_1$-$C_6$ alkyl, $C_2$-$C_6$ alkenyl, $C_2$-$C_6$ alkynyl, $C_1$-$C_6$ alkyloxy, aryl-($C_1$-$C_6$ alkylene)-, hydroxy-$C_1$-$C_6$-alkyl, and $C_1$-$C_6$-alkoxy-$C_1$-$C_6$-alkyl, wherein the alkyl, alkenyl, alkynyl, alkyloxy, and aryl-alkylene groups are each optionally substituted; p is an integer between 0 and 15; q is 1, 2, 3 or 4; r is 1, 2 or 3; r' is 0 or 1; s is 1, 2, 3 or 4; and m is 0, 1, 2, 3, 4 or 5; wherein the configuration of any of the chiral centers may optionally be R or S.

In another embodiment, J is
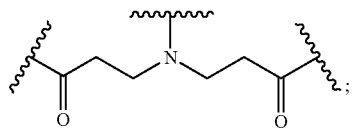
and the radionuclide is selected from the group consisting of $^{11}C$, $^{13}N$, $^{15}O$, $^{18}F$, $^{124}I$, $^{125}I$, $^{131}I$, and $^{75}Br$. In yet another embodiment, J is
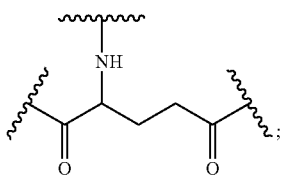
and the radionuclide is selected from the group consisting of $^{11}C$, $^{13}N$, $^{15}O$ $^{18}F$, $^{124}I$, $^{125}I$, $^{131}I$ and $^{75}Br$.
One aspect of the present invention is a compound of formula VI:
VI
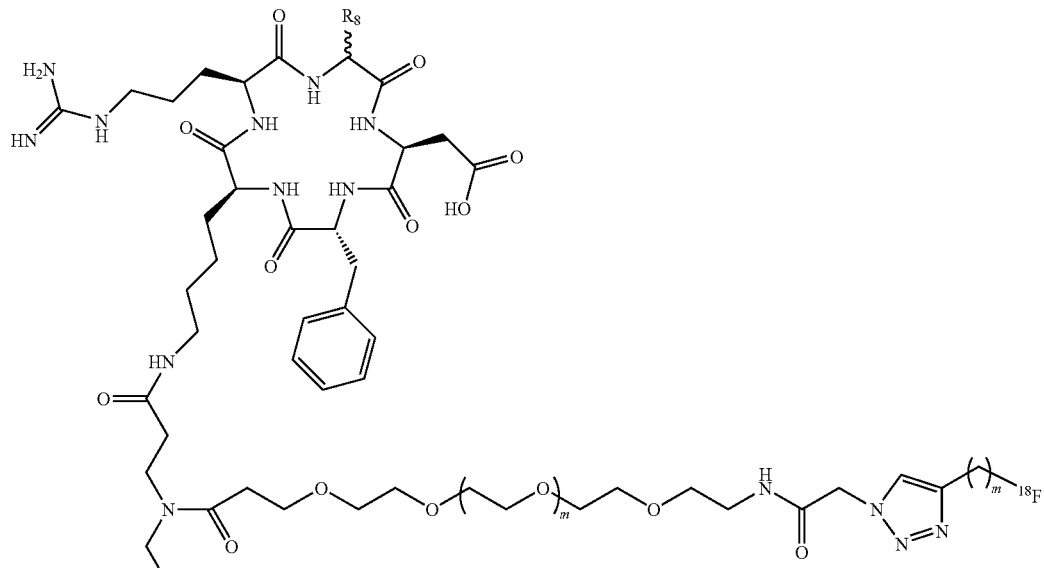
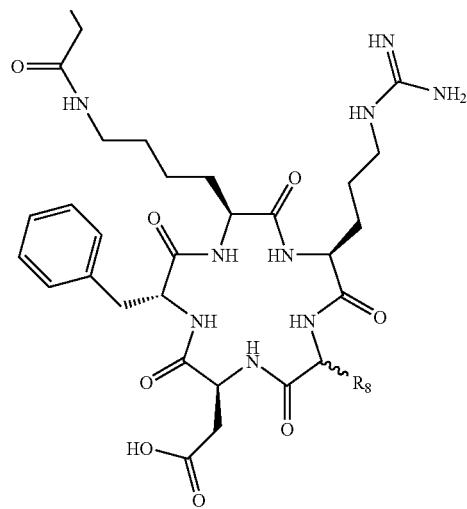

wherein each $R_8$ is independently selected from the group consisting of a side chain of a natural amino acid and a side chain of an unnatural amino acid, wherein the natural amino acid and the unnatural amino acid is either in the D or L form; m is 0 to 4, and n is 1-5. In one variation, m is 0 and n is 3.

In one embodiment, there is provided a pharmaceutical composition comprising any of the above disclosed compounds and a pharmaceutically acceptable carrier. In one aspect, the compounds disclosed herein can be used as tracers in Positron Emission Tomography (PET) or Single Photon Emission Computed Tomography (SPECT).

In another embodiment, there is provided a method of monitoring the level of integrin receptor within a body of a patient, the method comprising: (a) administering to the patient any of the above cited radiolabeled cyclopeptides, and (b) employing a nuclear imaging technique selected from the group consisting of positron emission tomography (PET) and single photon emission computed tomography (SPECT) for monitoring a distribution of the cyclic polypeptide within the body or within a portion thereof. In one embodiment, the integrin receptor is $\alpha_v\beta_3$.

In another embodiment, there is provided a method of visualizing integrin expression within a body of a patient, the method comprising: (a) administering to the patient any of the above cited radiolabeled cyclopeptides; and (b) employing a nuclear imaging technique selected from the group consisting of positron emission tomography (PET) and single photon emission computed tomography (SPECT) for visualizing a distribution of the radiolabeled cyclopeptide within the body or within a portion thereof. In one embodiment, the integrin receptor is $\alpha_v\beta_3$.

In another embodiment, there is provided a method for imaging of blood vessel growth in solid tumors based on expression of integrin $\alpha_v\beta_3$ within the body of a patient, the method comprising: (a) administering to the patient any of the above cited the radiolabeled cyclopeptides; (b) employing a nuclear imaging technique selected from the group consisting of positron emission tomography (PET) and single photon emission computed tomography (SPECT) for imaging a distribution of the radiolabeled cyclopeptide within the body or within a portion thereof and c) correlating the distribution of the radiolabeled cyclopeptide to the growth of blood vessels in solid tumors. In one embodiment, the integrin receptor is $\alpha_v\beta_3$.

The integrin $\alpha_v\beta_3$ plays an important role in regulating tumor growth and angiogenesis. The non-invasive visualization and quantification of $\alpha_v\beta_3$ integrin levels in patients enables a variety of applications. One such application is determination of $\alpha_v\beta_3$ levels before therapy with $\alpha_v\beta_3$ antagonists. Patients with low or no $\alpha_v\beta_3$ expression might not benefit from $\alpha_v\beta_3$ antagonist therapy and could then receive alternate treatment. Patients with $\alpha_v\beta_3$ positive lesions could have their treatment optimized, based on the use of the compounds of the present application to evaluate inhibition of the $\alpha_v\beta_3$ integrin.

Pharmaceutical compositions of the compounds of this application, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, 5% dextrose in water or buffered sodium or ammonium acetate solution. Such formulations are especially suitable for parenteral administration but may also be used for oral administration. Excipients, such as polyvinylpyrrolidinone, gelatin, hydroxycellulose, acacia, polyethylene glycol, mannitol, sodium chloride, or sodium citrate, may also be added. Alternatively, these compounds may be encapsulated, tableted, or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols, or water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax. The pharmaceutical preparations are made following the conventional techniques of pharmacy involving milling, mixing, granulation, and compressing, when necessary, for tablet forms; or milling, mixing, and filling for hard gelatin capsule forms. When a liquid carrier is used, the preparation may be in the form of a syrup, elixir, emulsion, or an aqueous or non-aqueous suspension. Such a liquid formulation may be administered directly p.o. or filled into a soft gelatin capsule. Suitable formulations for each of these methods of administration may be found in, for example, REMINGTON: THE SCIENCE AND PRACTICE OF PHARMACY, A. Gennaro, ed., 20th edition, Lippincott, Williams & Wilkins, Philadelphia, Pa.

The pharmaceutical compositions of the present invention may be in the form of a sterile injectable preparation. Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents.

The following procedures may be employed for the preparation of the compounds of the present invention. The starting materials and reagents used in preparing these compounds are either available from commercial suppliers such as the Aldrich Chemical Company (Milwaukee, Wis.), Bachem (Torrance, Calif.), Sigma (St. Louis, Mo.), or are prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In some cases, protective groups may be introduced and finally removed. Certain "protective groups" such as an N-acetyl group, may be incorporated and remain as part of the desired compound. Suitable protective groups for amino, hydroxy, and carboxy groups are described in Greene et al., *Protective Groups in Organic Synthesis*, Second Edition, John Wiley and Sons, New York, 1991. Standard organic chemical reactions can be achieved by using a number of different reagents, for examples, as described in Larock: *Comprehensive Organic Transformations*, VCH Publishers, New York, 1989 The novel cyclopeptide analogs presented herein are prepared using click chemistry [10-18]. Click chemistry, as used in this application, describes the rapid, selective and specific formation of 1,4- or 1,5-disubstituted 1,2,3-triazoles starting from alkyl azides and terminal alkynes. One or more triazole moieties are attached to the cyclic peptide, the hydrophilic linker, or the radiolabel tag.

Click chemistry is a high-yielding and modular approach and as such, the pharmacokinetic properties of these cyclopeptide analogs are easily modified.

The invention is further described by the following non-limiting examples.

Scheme I provides exemplary cyclopeptides containing RGD mimetic fragments.

Scheme I

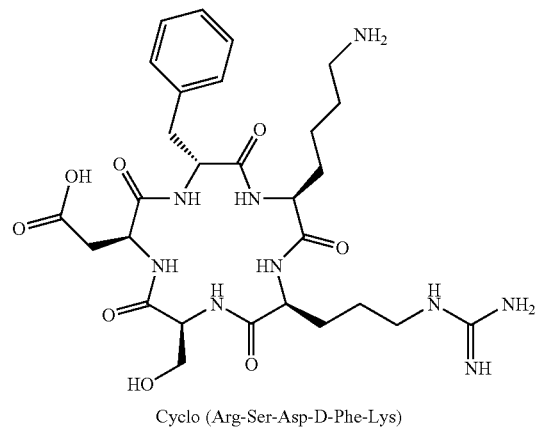

Cyclo (Arg-Ser-Asp-D-Phe-Lys)

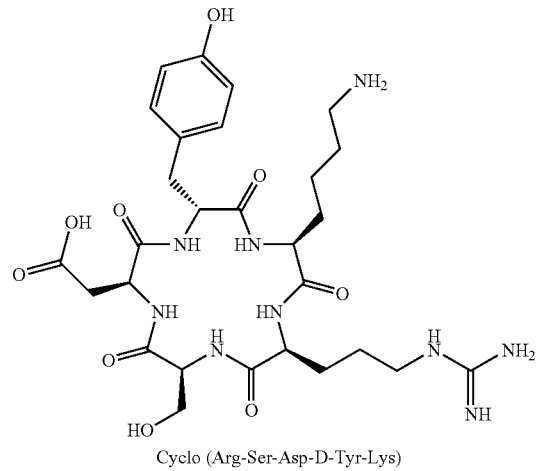

Cyclo (Arg-Ser-Asp-D-Tyr-Lys)

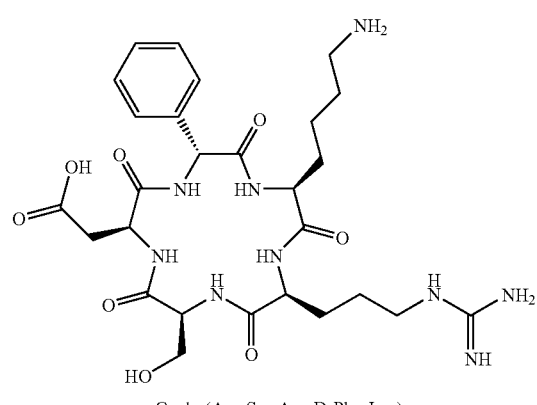

Cyclo (Arg-Ser-Asp-D-Phg-Lys)

-continued

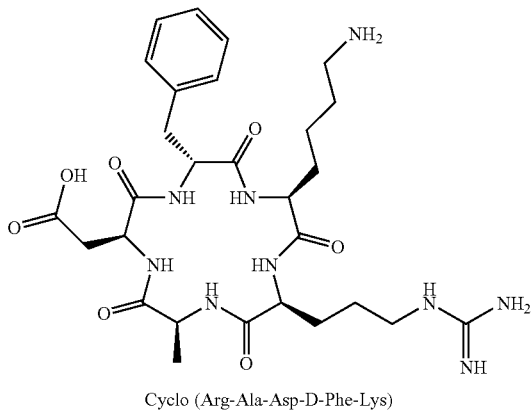

Cyclo (Arg-Ala-Asp-D-Phe-Lys)

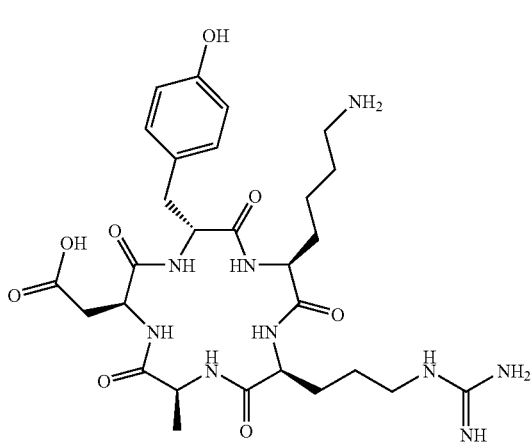

Cyclo (Arg-Ala-Asp-D-Tyr-Lys)

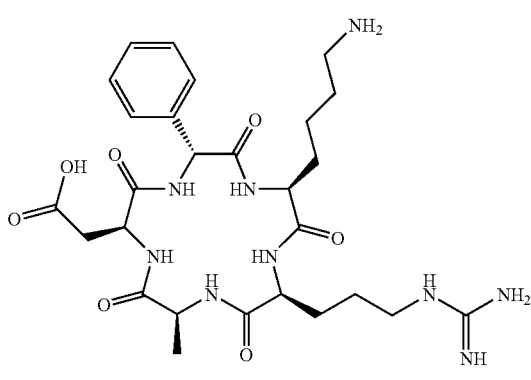

Cyclo (Arg-Ala-Asp-D-Phg-Lys)

Scheme II provides an exemplary reaction scheme for the synthesis of a cyclopeptide containing Arg-Ala-Asp (RAD) fragment.

Scheme II
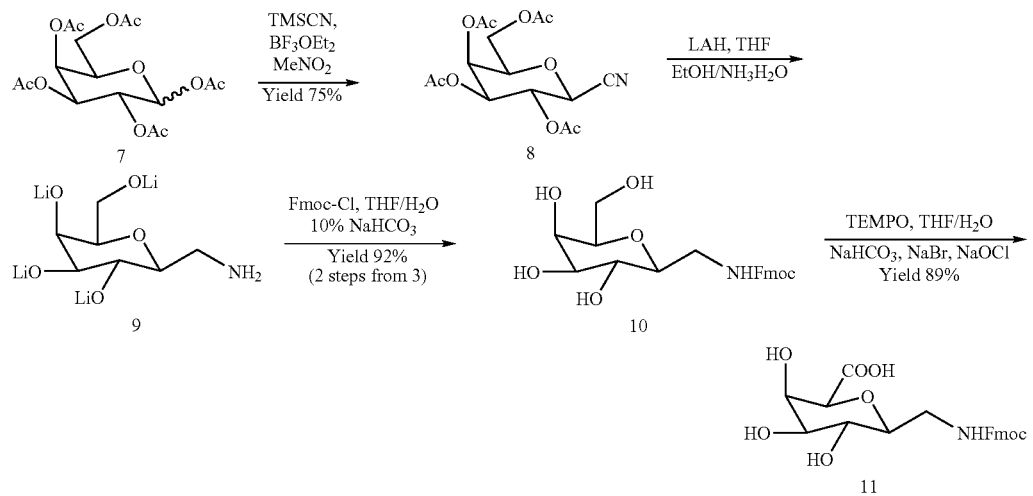
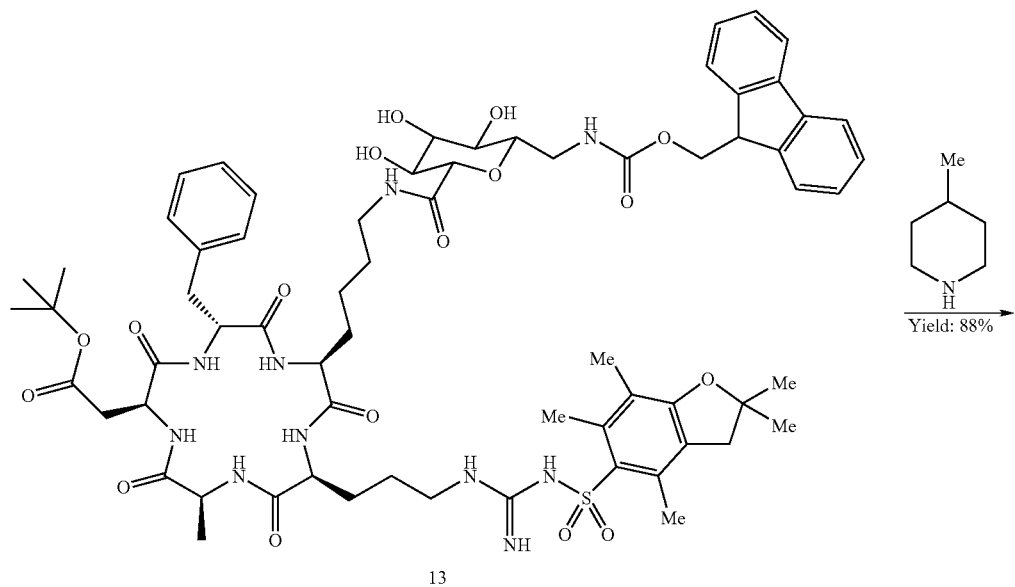

-continued
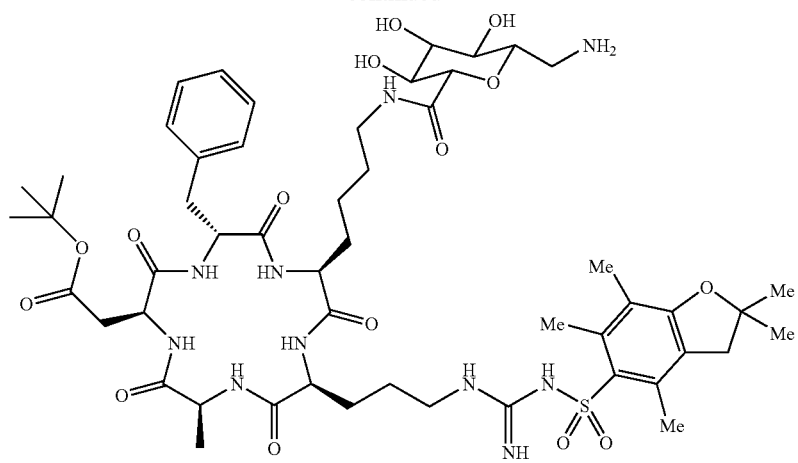
14
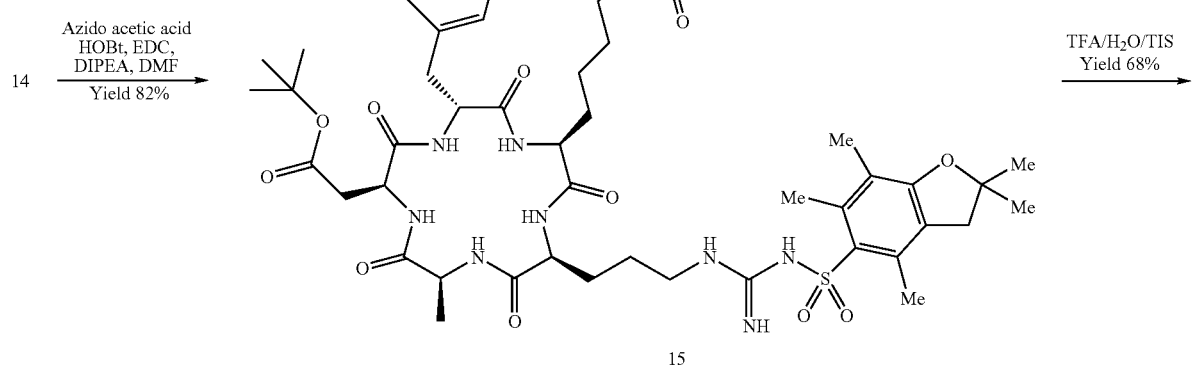
14 →(Azido acetic acid, HOBt, EDC, DIPEA, DMF, Yield 82%)→ 15 →(TFA/H₂O/TIS, Yield 68%)→
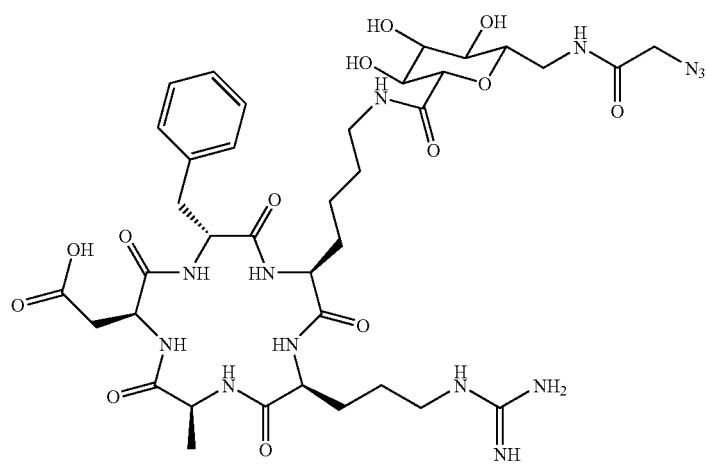
16

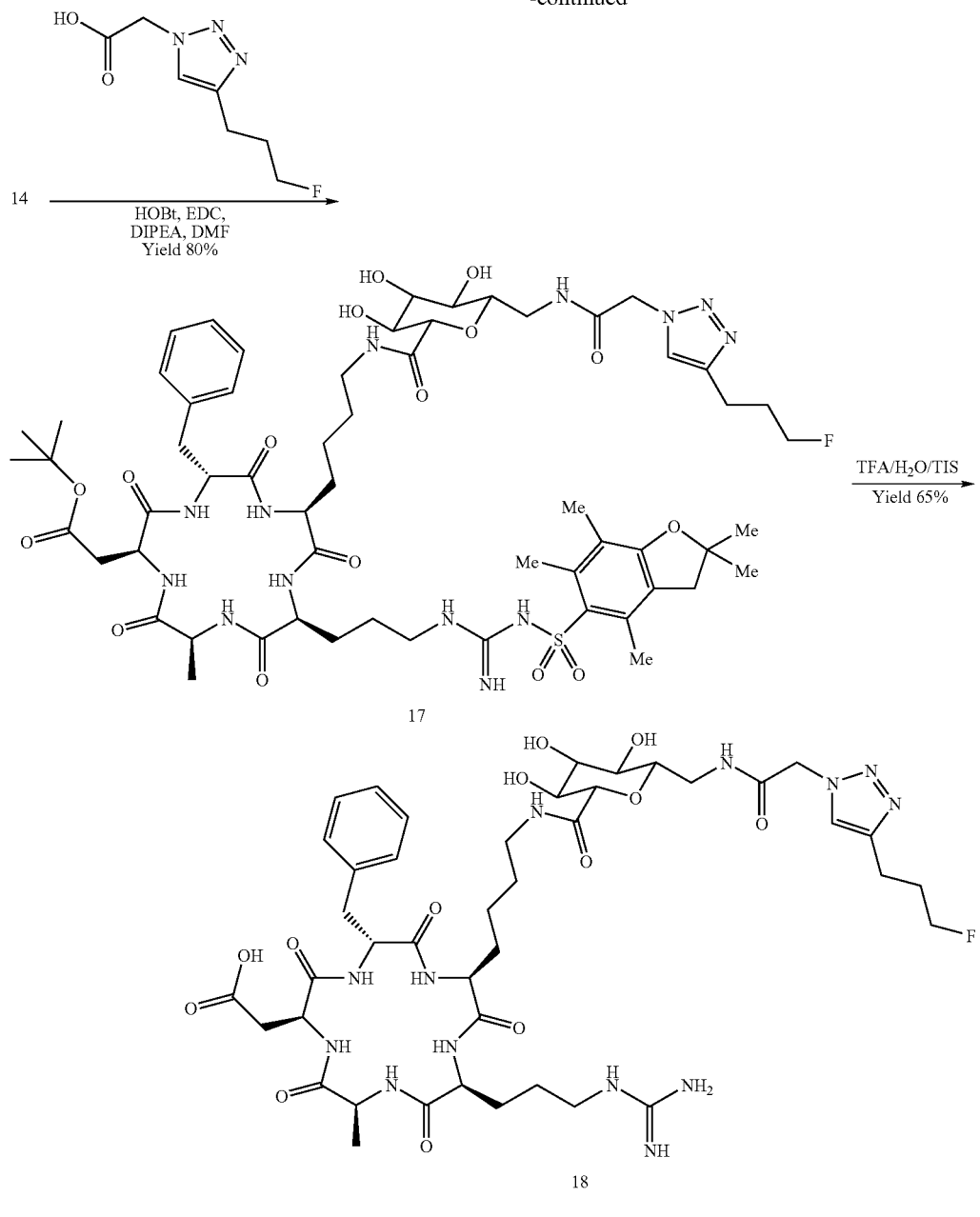

Synthesis of 8 Compound 7 (50 g, 0.12 mol, 1 equiv) in nitromethane (200 mL) was treated with trimethylsilyl cyanide (15 mL, 0.21 mol, 1.7 equiv) and BF$_3$.OEt$_2$ (3 mL, 0.05 mol, 0.36 equiv) at room temperature. The reaction mixture was stirred at room temperature for 1 h. Additional amount of TMSCN (15 mL, 0.21 mol, 1.7 equiv) and BF$_3$.OEt$_2$ (3 mL, 0.05 mol, 0.36 equiv) were added and stirred at room temperature for 1 h. Volatiles were removed under vacuo and the crude reaction mixture was redissolved in ethyl acetate (1 L), washed with NaHCO$_3$ solution (2×250 mL), water (1×500 mL), brine (1×250 mL) and dried over Na$_2$SO$_4$. The Organic layer was concentrated under vacuo to reduce half of its volume and recrystallized by cooling to 0° C. Pale yellow solid was filtered and washed with EtOAc, dried under vacuo to afford 32 g of 8 (75% yield). $^1$H NMR (CDCl$_3$, 400 MHz), δ: 5.54 (t, 1H), 5.43 (dd, 1H, J=3.2 Hz, 1.2 Hz), 5.01 (dd, 1H, J=10 Hz, 3.2 Hz), 4.30 (d, 1H, J=10 Hz), 4.12 (d, 2H, J=6.4 Hz), 3.95 (td, 1H, J=1.2 Hz, 6.4 Hz), 2.19-2.00 (4s, 12H, acetyl-CH$_3$). Mass Spec (lo-res): Calc'd for C$_{15}$H$_{19}$NO$_9$: 357.11; found: 380.1 (M+Na)$^+$.

Synthesis of 9. Lithium aluminum hydride (17.7 g, 444 mmol, 4 eq) was added to THF (anhydrous, 75 ml) to form a suspension. Compound 8 (39.7 g, 111 mmol, 1 eq) in anhydrous THF (420 ml) was added to the suspension through an addition funnel at 0° C. to in 2 hrs to form a light yellow suspension. The mixture was allowed to room temperature and stirred over night. To the mixture stirred in an ice bath, was added EtOH (80 mL) dropwise and ammonium hydroxide solution (aq, 28-30%) 86 mL. The mixture was stirred at room temperature for 2 hrs. The result mixture was filtered and washed with water (25 mL×3) and diethyl ether (30 mL×3). The cake was dried over P$_2$O$_5$ under vacuo for two days to afford a white solid 9 with inorganic salt and small amount of water (128 g, ca. purity 16%, 95% yield) to be carried out to next step without purification. The product can be characterized by NMR after filtration of its $D_2O$ suspension. $^1$H NMR ($D_2O$, 400 MHz), δ: 3.74 (d, 1H, J=3.6 Hz), 3.56-3.51 (m, 2H), 3.44-3.29 (m, 2H), 3.29 (t, 1H, J=9.6 Hz), 3.05 (m, 1H), 2.83 (m, 1H), 2.51 (dd, 1H, J=13.6 Hz, J=8.0 Hz). Mass Spec (lo-res): Calc'd for $C_7H_{15}NO_5$: 193.10; found: 194.1 $(M+H)^+$.

Synthesis of 10. Compound 9 (132 g, 109 mmol, 16% purity, 1.1 eq) was dissolved in an aqueous solution of $NaHCO_3$ (10% wt, 300 mL). To the mixture at the ice bath temperature, was added Fmoc-Cl (26.5 g, 99 mmol, 1 eq in THF (150 mL) dropwise. Addition time was 1.5 h. After addition, LCMS indicates completion of the reaction. HCl (conc. 37%, 90 mL) was added dropwise to quench the reaction until pH reached 3-4. The suspension was concentrated under vacuum to remove THF. The resulting sticky suspension was washed with hot THF (250 mL×5) with ultrasound. The combined liquid phases were concentrated in vacuo to afford a white solid crude product (90 g). The crude product was triturated with hot EtOAc (400 mL) and washed with water (50 mL) and diethyl ether (50 mL×2) to afford the desired product 10 as a white solid (40 g, 97% yield) after overnight drying under vacuo with $P_2O_5$. $^1$H NMR ($d_6$-DMSO, 400 MHz), δ: 7.89 (d, 2H, J=7.2 Hz), 7.70 (d, 2H, J=7.2 Hz), 7.42 (t, 2H, J=7.2 Hz), 7.33 (t, 2H, J=7.2 Hz), 7.24 (t, 1H, J=4.4 Hz), 4.85 (b, 1H), 4.69 (b, 1H), 4.49 (b, 1H), 4.25-3.72 (m, 3H), 3.64 (b, 1H), 3.60-3.41 (m, 3H), 3.31-3.26 (m, 4H), 3.02 (t, 1H, J=7.6 Hz), 2.91 (m, 1H). Mass Spec (lo-res): Calc'd for $C_{22}H_{25}NO_7$: 415.16; found: 416.0 $(M+H)^+$.

Synthesis of 11. To Compound 10 (10 g, 24 mmol, 1 eq) in THF (115 ml) and water (115 ml), was added the sodium bicarbonate (12 g, 143 mmol, 6 eq). To the mixture was added TEMPO (2,2,6,6-Tetramethyl Piperidinyloxy, Free Radical) (0.752 g, 4.81 mmol, 0.2 eq) and sodium bromide (0.743 g, 7.22 mmol, 0.3 eq). The mixture was cooled to 0° C. with ice bath, sodium hypochlorite solution (aq, 10%-13% chorine) (39.4 g, 53.0 mmol, 2.2 eq) dropwise in 45 mins. After addition, the reaction mixture was concentrated under vacuum without heating to remove organic volatiles. The aqueous layer was extracted with $Et_2O$ (50 mL×2), then acidified with HCl (aq, conc. 37%, 15 mL) until pH reached 2. The aqueous layer was extracted with ethyl acetate (100 mL×4). The combined organic layers were concentrated to afford crude product as a white solid. The crude product was triturated with hot diethyl ether (75 mL×3) under ultrasound to give a while solid 11 (9.2 g, 89% yield). $^1$H NMR ($d_6$-DMSO, 400 MHz), δ: 12.10 (b, 1H), 7.89 (d, 2H, J=7.2 Hz), 7.70 (d, 2H, J=7.2 Hz), 7.42 (t, 2H, J=7.2 Hz), 7.34 (t, 2H, J=7.2 Hz), 7.26 (t, 1H, J=4.4 Hz), 4.93 (b, 1H), 4.89 (b, 1H), 4.76 (b, 1H), 4.31 (d, 2H, J=6.8 Hz), 4.24 (d, 1H, J=6.8 Hz), 4.04 (s, 1H), 3.94 (s, 1H), 3.58-3.51 (m, 1H), 3.30-3.25 (m, 1H), 3.17-2.97 (m, 3H). Mass Spec (lo-res): Calc'd for $C_{22}H_{23}NO_8$: 429.14; found: 430.1 $(M+H)^+$.

Synthesis of 13. To a solution of Compound 11 (153 mg, 0.355 mmol, 1.2 eq) in DMF (5 ml), was added HOBt (48 mg, 0.355 mmol, 1.2 eq) and EDC (68 mg, 0.355 mmol, 1.2 eq). The mixture was stirred at room temperature for 2 hrs. RADfK-(protected) HCl salt, 12 [285 mg, 0.296 mmol, 1.0 eq] and DIPEA (0.103 mL, 0.592 mmol, 2 eq) in DMF (5 mL) was added to the reaction dropwise. LCMS indicated the completion of reaction after overnight stirring. To the mixture was added EtOAc (60 mL), ultrasounicated for 30 minutes, then cooled to 0° C. White precipitates formed from the solution. The mixture was filtrated. Cake was washed with water (10 mL) and Ether (10 mL×2) and dried to afford Compound 13 as a white solid (352 mg, 89% yield). Mass Spec (lo-res): Calc'd for $C_{67}H_{88}N_{10}O_{17}S$: 1336.6; found: 1337.5 $(M+H)^+$.

Synthesis of 14. To a round bottle flask containing Compound 13 (352 mg, 0.263 mmol, 1 eq) in DMF (5 mL), was added 4-methylpiperidine (1.5 mL, 13.2 mmol, excess). LCMS indicates completion of the reaction after overnight stirring. The reaction was concentrated to remove 4-methylpiperidine. Acetonitrile (10 mL×3) was added to facilitate co-evaporation. The residue was dried under vacuo for 2 hrs. The white solid residue was then washed with ether (10 mL×3) by ultrasound. The residue solid was filtered and dried under vacuo overnight to afford Compound 14 (258 mg, 88% yield). Mass Spec (lo-res): Calc'd for $C_{52}H_{78}N_{10}O_{15}S$: 1114.54; found: 1115.5 $(M+H)^+$.

Synthesis of 17. To a solution of 2-(4-(3-fluoropropyl)-1H-1,2,3-triazol-1-yl)acetic acid (10 mg, 0.053 mmol, 2.5 equiv) in DMF (5 ml) was added HOBt (7.2 mg, 0.053 mmol, 2.5 equiv) and EDC (10 mg, 0.053 mmol, 1.5 equiv). The mixture was stirred at room temperature for 30 min. To the mixture was then added Compound 14 (23.6 mg, 0.021 mmol, 1.0 eq) in DMF (2 mL) and DIPEA (10 uL, 0.053 mmol, 2.5 equiv). The reaction was stirred overnight. LCMS indicated that no starting material remained. The mixture was diluted with water (10 mL) to precipitate out solid crude product. After an ether wash and drying a yellow solid 17 was recovered (22 mg, 80% yield). Mass Spec (lo-res): Calc'd for $C_{59}H_{86}FN_{13}O_{16}S$: 1283.6; found: 1284.5 $(M+H)^+$.

Synthesis of 18. To the cocktail solvents (TFA:TIS: $H_2O$=95:2.5:2.5, 2 mL, excess) at ice bath temperature, was added Compound 17 (22 mg, 0.017 mmol, 1 eq). The reaction was allowed to room temperature and stirred for 2 hrs until LCMS indicated completion of the reaction. The reaction was concentrated to remove all volatiles and redissolved in water (5 mL) filtered through filter (0.45 μm). The filtrates were purified by semi-prep HPLC [column: Phenomenex, Luna C18(2) column, 250×21.20 mm, 5 micron; flow rate: 12 mL/min; gradient: 10% to 40% MeCN in water in 30 min]. The fractions were collected and combined. The solvents were removed by lyophilization overnight to afford compound 18 (10 mg, 65% yield). $^1$H NMR ($D_2O$, 400 MHz), δ: 7.64 (s, 1H, triazole CH—), 7.25-7.07 (m, 5H, Phe-Phenyl-), 5.06 (s, 2H, —NHCO—$CH_2$-triazole), 4.53 (dd, 1H, Asp-CH—), 4.51-4.39 (m, 3H, Phe-CH— and —$CH_2CH_2F$), 4.37 (t, 2H, —$CH_2CH_2F$), 4.22 (dd, 1H, Arg-CH—), 4.08 (dd, 1H, Gly-CH—), 4.00 (d, 1H, sugar —H1), 3.74 (dd, 1H, Lys-CH—), 3.55-3.53 (m, 2H, sugar —H3 and —$CH_2$—NH—), 3.43-3.27 (m, 4H, sugar —H2, —H4, —H5 and —$CH_2$—NH—), 3.07-2.61 (m, 9H, Arg-$CH_2$—NH—CNH—$NH_2$Lys-$CH_2$—NH-Phe-$CH_2$-Ph Asp-$CH_2$COOH and —$CH_2CH_2CH_2F$), 2.57-2.51 (dd, 1H, —$CH_2$COOH), 1.92-1.82 (m, 2H, —$CH_2CH_2F$), 1.76-1.73 (m, 3H, Gly-$CH_2$—$CH_3$), 1.63-1.61 (m, 1H, Arg-CH—$CH_2$—), 1.49-1.23 (m, 6H, Arg-CH—$CH_2$— Lys-CH—$CH_2$— and Arg-CH—$CH_2$—$CH_2$—), 1.11-1.06 (m, 2H, Lys-CH—$CH_2$—$CH_2$—$CH_2NH$), 0.78-0.72 (m, 2H, Lys-CH—$CH_2$—$CH_2$—$CH_2NH$). $^{19}$F NMR ($D_2O$, 376 MHz), δ: −75.7 (TFA, —$CF_3$), −218.96 (tt, J=49.6 Hz, 29.2 Hz). Mass Spec (lo-res): Calc'd for $C_{42}H_{62}FN_{13}O_{13}$: 975.46; found: 976.3 $(M+H)^+$.

Synthesis of 15. To azido acetic acid (5.65% solution in DCM/THF, 283 mg, 0.16 mmol, 2.5 eq) in DMF (2 mL), was added HOBt (21.5 mg, 0.16 mmol, 2.5 eq) and EDC (30.5 mg, 0.16 mmol). The mixture was stirred at room temperature for 30 min. Compound 14 (71 mg, 0.064 mmol) in DMF (3 mL) was added with DIPEA (28 μL, 0.16 mmol, 2.5 eq) to the above mixture. The reaction was stirred at room temperature for overnight. LCMS indicated completion of the reaction. The reaction was quenched by addition of water (few drops). DMF was removed under vacuo. Acetonitrile (5 mL×3) was added to facilitate co-evaporation of DMF. To the residue was added water (8 mL), treated with ultrasound for 30 min. The white solid precipitate was collected by filtration. The cake was washed with mother liquid (10 mL×1), ether (8 mL×2) and dried under vacuo with $P_2O_5$ overnight to afford Compound 15 (63 mg, 82% yield). Mass Spec (lo-res): Calc'd for $C_{54}H_{79}N_{13}O_{16}S$: 1197.55; found: 1198.4 $(M+H)^+$.

Synthesis of 16. To Compound 15 (63 mg, 0.053 mmol, 1 eq), was added cocktail solvents (TFA:TIS:$H_2O$=95:2.5:2.5, 2 mL, excess). The reaction was stirred at room temperature for 30 min until LCMS indicated completion of the reaction. The reaction was concentrated to remove all volatiles and redissolved in water (10 mL) filtered through filter (0.45 μm). The filtrates was purified by semi-prep HPLC to afford 13 (32 mg, 68% yield). $^1H$ NMR ($D_2O$, 400 MHz), δ: 7.23-7.08 (m, 5H, Phe-Phenyl-), 4.60 (dd, 1H, Asp-CH—), 4.36 (dd, 1H, Phe-CH—), 4.22 (dd, 1H, Arg-CH—), 4.09 (dd, 1H, Gly-CH₂—), 4.00 (d, 1H, sugar H1), 3.97 (s, 1H, Gly-CH—), 3.87 (s, 2H, —CH₂—N₃), 3.75 (dd, 1H, Lys, —CH—), 3.58-3.53 (m, 3H, sugar —H3 and —CH₂—NH—), 3.41-3.27 (m, 5H, sugar H2, —H4, —H5 and —CH₂—NH—), 3.08-2.98 (m, 4H, Arg-CH₂—NH—CNH—NH₂ and Lys-CH₂—NH—), 2.94-2.72 (m, 4H, Phe-CH₂-Ph and Asp-CH₂COOH), 2.58-2.52 (dd, 1H, —CH₂COOH), 1.76-1.73 (m, 1H, Arg-CH—CH₂—), 1.64-1.60 (m, 3H, Gly-CH₂—CH₃), 1.54-1.51 (m, 2H, Arg-CH—CH₂— and Lys-CH—CH₂—), 1.43-1.35 (m, 3H, Lys-CH—CH₂— and Arg-CH—CH₂—CH₂—), 1.25-1.23 (m, 2H, Lys-CH—CH₂—CH₂—CH₂—CH₂NH), 0.81-0.76 (m, 2H, Lys-CH—CH₂—CH₂—CH₂—CH₂NH). Mass Spec (lo-res): Calc'd for $C_{37}H_{55}N_{13}O_{13}$: 889.40; found: 890.3 $(M+H)^+$.

Conjugation of [$^{18}F$]fluoroalkyne, prepared using the corresponding tosylated alkyne as a precursor, to cyclopeptides derivatized with azido group via Cu(I) mediated 1,3-dipolar cycloaddition yields the desired $^{18}F$-labeled products with good yields and excellent radiochemical purity. See Scheme III.

Scheme III

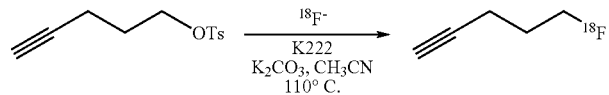

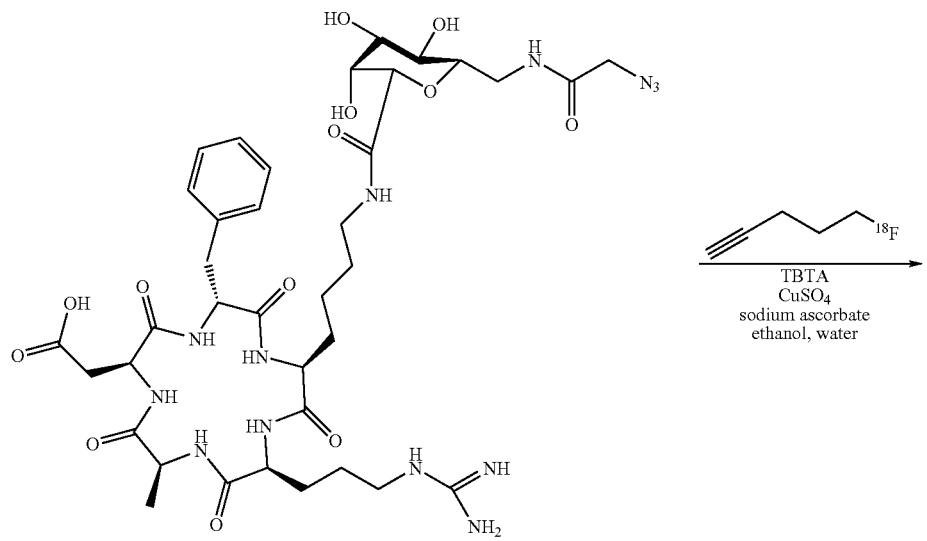

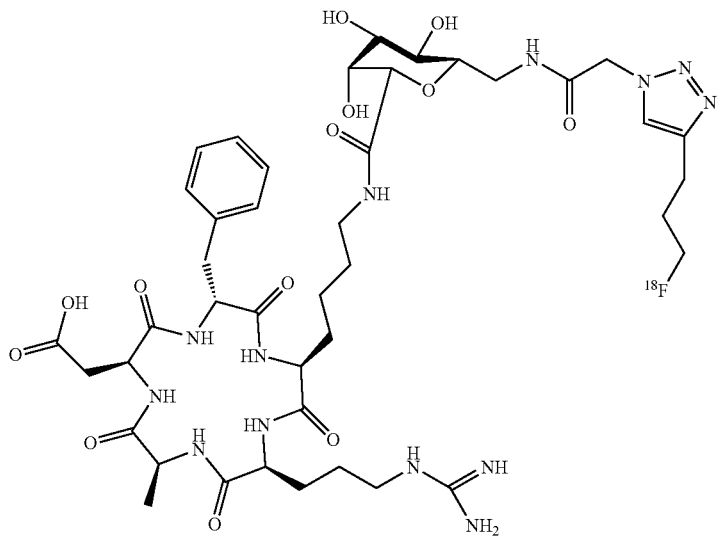

19

Exemplary procedure for the synthesis of 19 is as follows: 1-pentynyl tosylate (20 mg) is $^{18}$F-labeled in CH$_3$CN at 110° C. in the presence of K222 and K$_2$CO$_3$ for 5 min while simultaneously distilling the material into a cooled solution containing 1~2 mg of azido cyclopeptide 16 is dissolved in 0.25 mL of acetonitrile, 0.25 ml of ethanol:water 2:1, tris-(benzyltriazolylmethyl)amine (TBTA) (10-20 mg), sodium ascorbate (30-50 mg), and 250 μL of 0.1 M CuSO$_4$. The distillation may proceed for 20-60 minutes, and the reaction is allowed to react at room temperature for 0-40 minutes after the distillation is complete. Prior to purification of 19 by HPLC, the reaction is diluted with water (up to 2 mL). The reaction mixture is then loaded onto an HPLC C18 column for purification. After collecting the product 19, the material is reconstituted via C18 loading and unloading with EtOH and diluting with water to make a 10% EtOH:Water solution. Related radiolabled RDG mimetic analogs can be prepared in a similar fashion.

Another exemplary preparation of one of the cyclic RGD peptide derivatives of the present application is shown in Scheme IV.

Scheme IV:

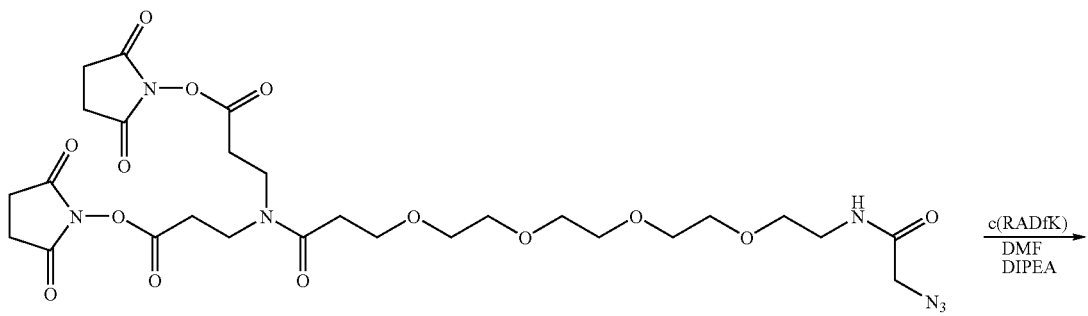

-continued
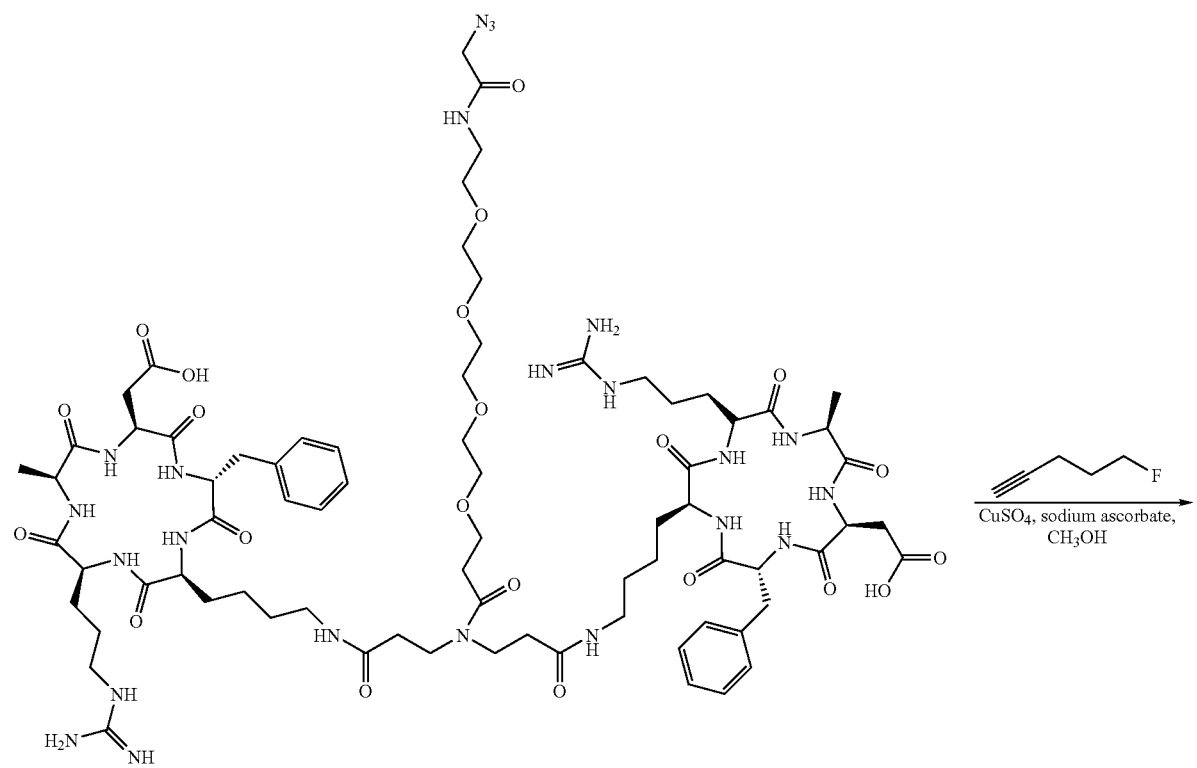
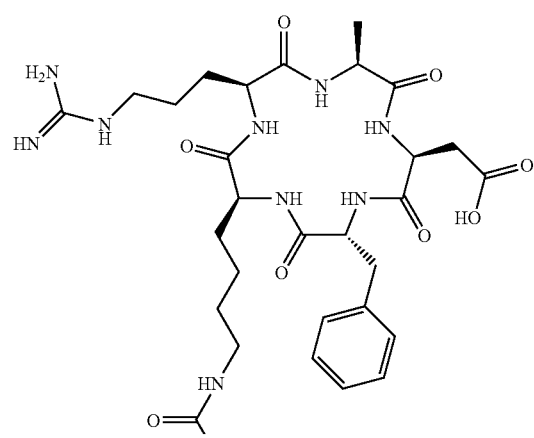

-continued
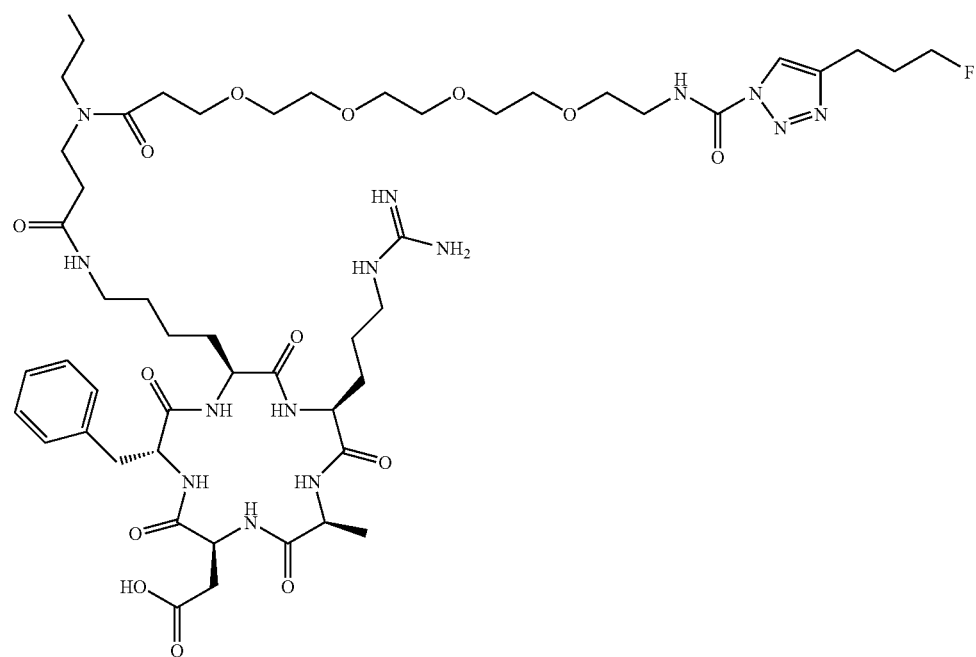
In Vitro Binding Assay:
TABLE 1
RGDfK derivatives employed in in vitro assay
| Compound | Chemical Structure | MW |
|---|---|---|
| 20 | 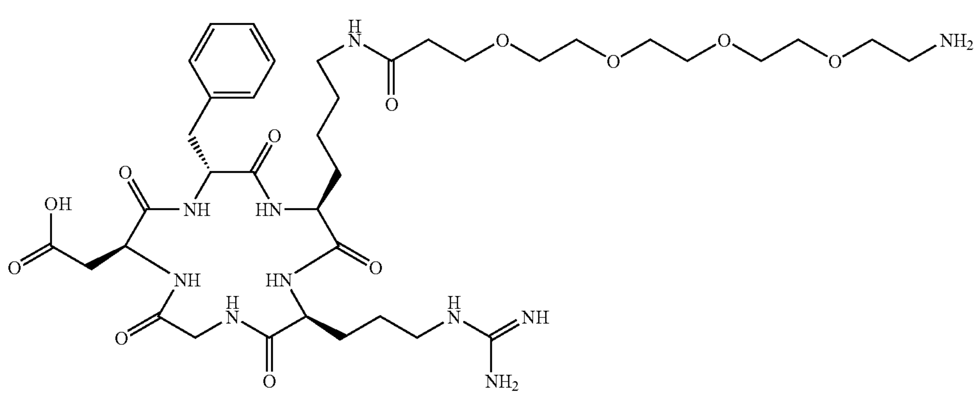 | 850.45 |

TABLE 1-continued

RGDfK derivatives employed in in vitro assay

| Compound | Chemical Structure | MW |
|---|---|---|
| 21 | 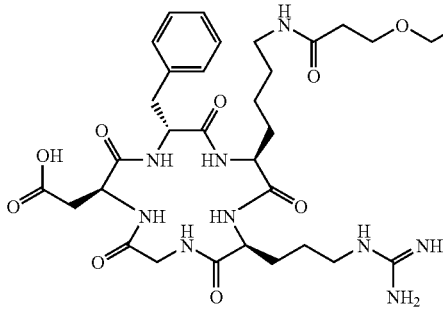 | 1208.50 |

Surface Plasmon Resonance (SPR) Assay:

Compound 20 was immobilized onto a CM5 chip (Supplier: Biacore. CM5 is a SPR chip with a carboxymethylated dextran covalently attached to a gold surface) via amine coupling. Intergrin $\alpha_v\beta_3$ samples at 50 nM concentration, premixed with a wide range of concentrations of RGD test compound (0~2000 nM), were flowed through the CM5 chip at 14° C.

The interactions between the flowing integrin $\alpha_v\beta_3$ sample and the surface of the chip were recorded by Biacore sensorgram signals. Flow cell #1 served as blank control and the flow cell #2 were coated with compound 20. After subtraction the blank signal of flow cell #1 from the signal of flow cell #2, the resulting sensorgram signals from each cycle were converted into percentage values and the $K_d$ and $IC_{50}$ values for each cyclopeptides were calculated.

Figure 2:
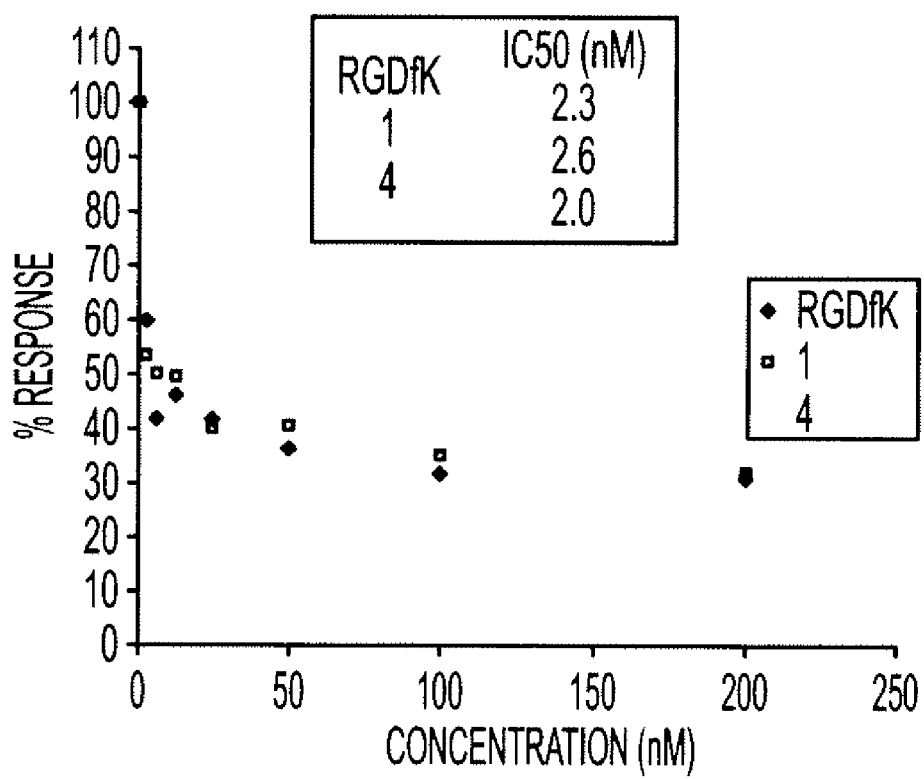
FIG. 2. shows $IC_{50}$ value comparison of cyclopeptides containing RGD mimetics with c(RGDfK) using surface plasmon resonance assay.

The results of this 'inverse' integrin $\alpha v\beta 3$ SPR assay show that cyclopeptides containing RGD mimetic fragment display surprisingly high binding affinity to integrin $\alpha v\beta 3$. The Kd and $IC_{50}$ values of cyclopeptides containing RGD mimetic fragment are very close to those of RGDfK, a well-known inhibitor to integrin $\alpha_v\beta_3$. See FIG. 1 and FIG. 2.

Competitive binding assay of cyclic peptides using immobilized integrin $\alpha_v\beta_3$ and biotinylated ligand vitronectin:

Inhibitory effects of cyclic peptides were quantified by measuring their effects on the interactions between immobilized integrin and biotinylated soluble ligand. Integrin $\alpha_v\beta_3$ was immobilized on a 96 well plate. The wells were then incubated with 10 nM of biotinylated ligand vitronectin and various concentration of cyclic peptides (0.1, 1, 10, 100, 1000, 10000, 100000 nM). After washing (3×5 min with binding buffer), bound biotinylated ligands were incubated with alkaline-phsphatase conjugated anti-biotin antibody. The plate was then washed three times with binding buffer. The wells were incubated with alkaline-phsphatase substrate and the intensities of yellow color product were measured in plate reader. Intensity of wells without cyclic peptides was set as 100% and used as control. Intensities of other wells in the presence of cyclic peptides were demonstrated accordingly as percentage of control wells. All treatments were carried out in triplicates.

Figure 3:
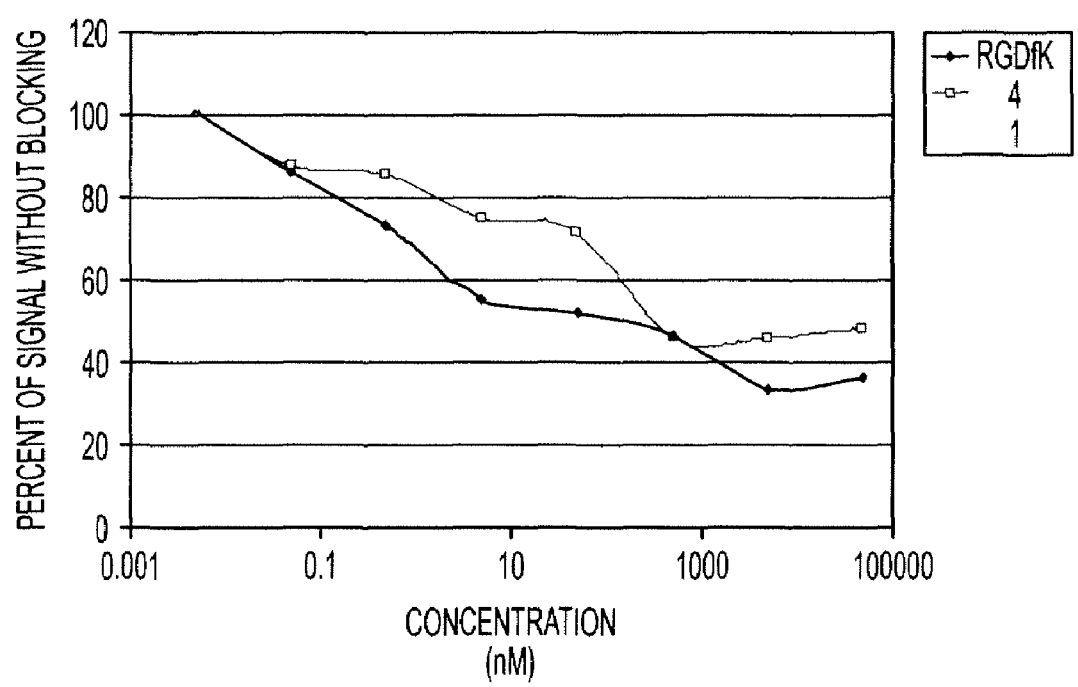
FIG. 3. shows $IC_{50}$ value comparison of cyclopeptides containing RGD mimetics with c(RGDfK) using competitive binding assay.

The results of the competitive binding assay show that cyclopeptides containing RGD mimetic fragment display surprisingly high binding affinity to integrin $\alpha_v\beta_3$. The $IC_{50}$ values of cyclopeptides containing RGD mimetic fragment are very close to that of RGDfK, a well-known inhibitor to integrin $\alpha_v\beta_3$. See FIG. 3.

Cell-Based Integrin Receptor-Binding Assay:

Integrin $\alpha_v\beta_3$ expressing U87MG cells were incubated with a series of concentration of cyclic peptides (0.01, 0.1, 1, 10, 100, 1000, 10000 nM) in the presence of 10 nM of green fluorescence labeled compound 21 for 2 hrs. After incubation, cells were washed three times to eliminate unbound cyclic peptides. Fluorescence readings (RLU) were then taken (excitation at 491 nm, emission at 518 nm, cutoff 515 nm). Fluorescence signals of wells without cyclic peptides were set as 100% and used as control. Fluorescence signals of other wells in the presence of cyclic peptides were demonstrated accordingly as percentage of control wells. All treatments were carried out in triplicates.

Figure 4A:
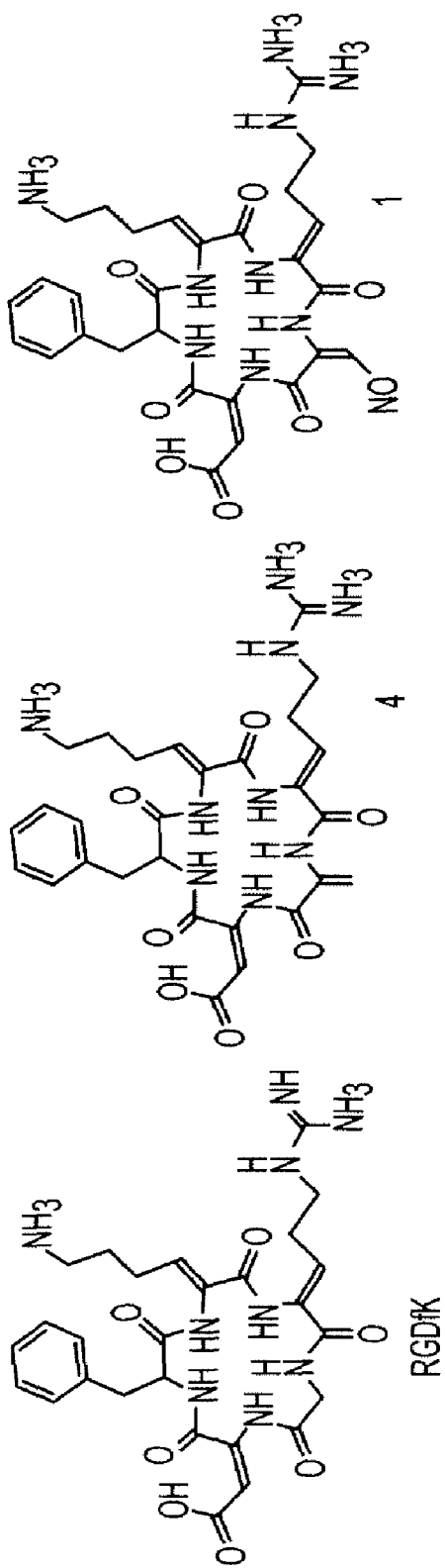
FIG. 4. shows a binding affinity comparison of 1) cyclic peptides 4, 1 and c(RGDfK), and 2) cyclic peptides 19 and 23 using cell-based intergrin $\alpha v\beta 3$ binding competition assay.
Figure 4A:
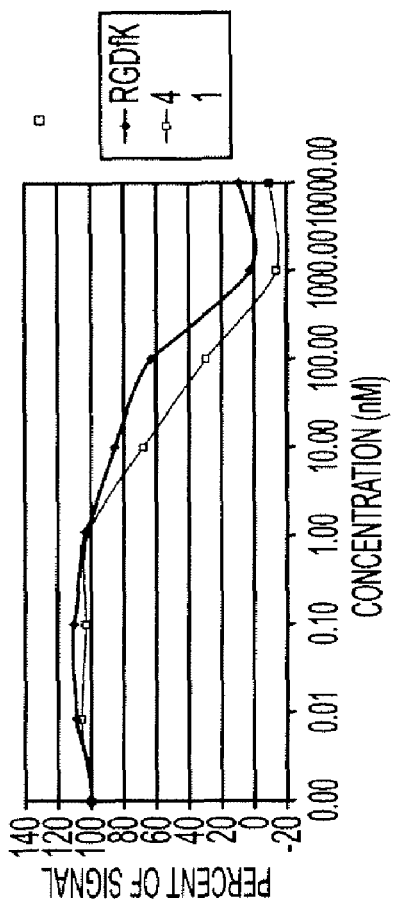
Figure 4B:
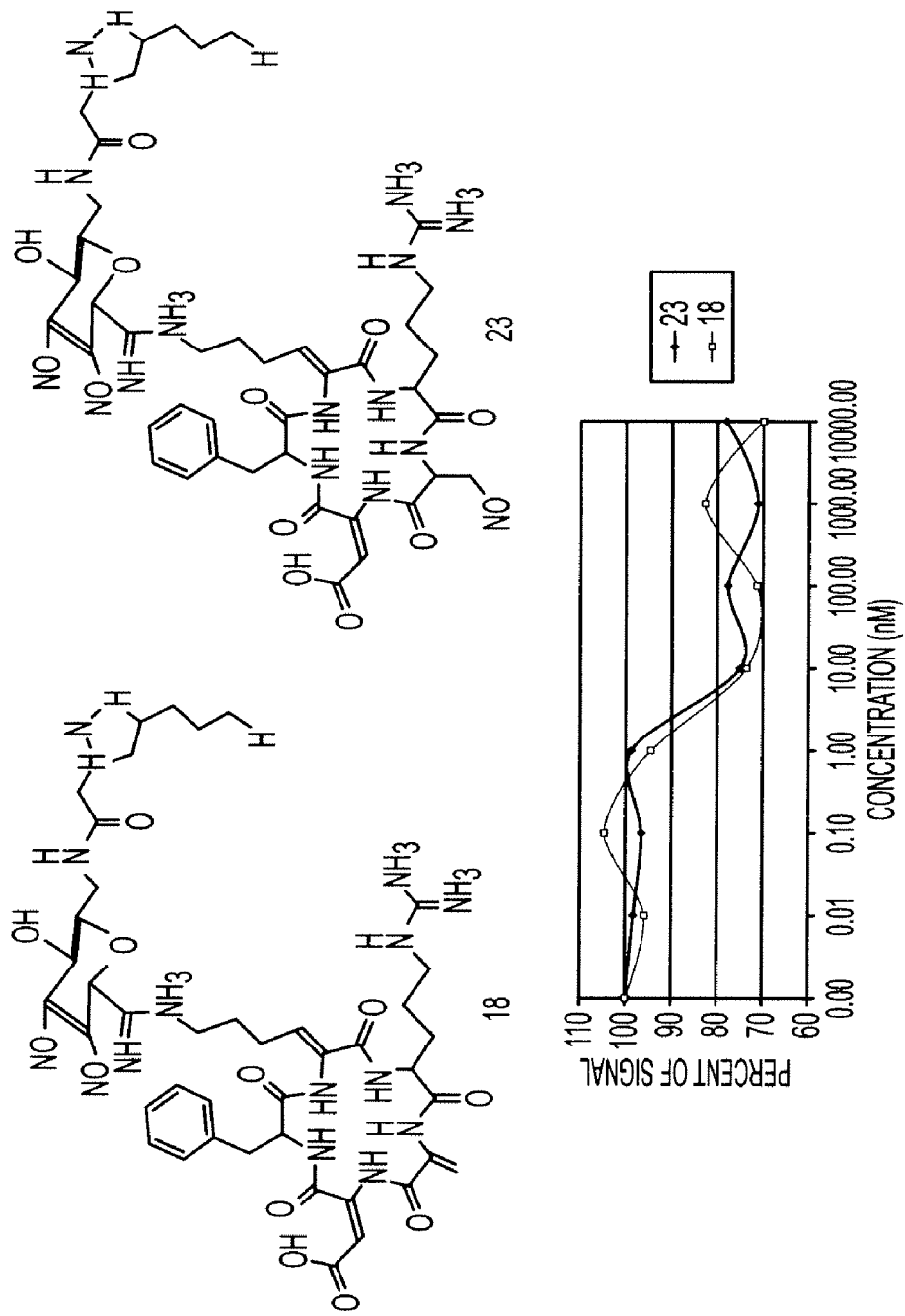

The results are consistent with that of surface plasmon resonance assay. The data further demonstrate that 1) cyclic peptides 4, 1 and RGDfK are very similar in potency, and 2) cyclic peptides 18 and 23 are very similar in potency. See FIG. 4.

Figure 5:
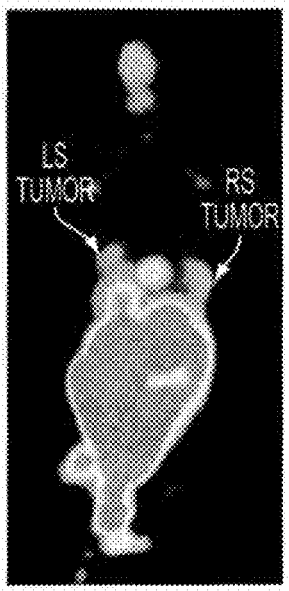
FIG. 5 is a microPET imaging of Compound 19 in a U87MG xenograft mouse model at 1 hour post-injection.

PET Studies: In vivo microPET imaging of a tumor-bearing mouse is performed on an anesthetized mouse bearing tumor xenograft of U87MG human glioblastoma after administration of the test imaging cyclic peptides. Animals are induced with 5% isoflurane/oxygen until anesthetized and then maintained on 2-2.5% isoflurane/oxygen inhalation for the duration of each PET scanning procedure (up to 2 hours). Anesthetized animals are placed on a heated pad for the duration of each PET scan. Animals are scanned at 1 hour post-injection for 30 min. In vivo microPET imaging shows that compound 19 is a very good tracer with a) good tumor uptake and retention, b) favorable renal clearance and very little liver uptake, c) fast wash-out rate from muscle and other healthy tissues, which includes kidney. See FIG. 5.

The invention will now be further described by the following numbered paragraphs.

1. A cyclopeptide of formula I:

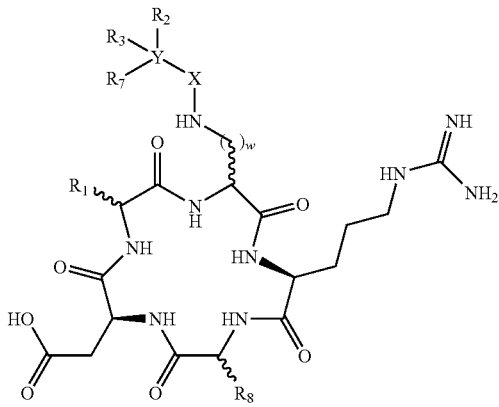

I wherein:

$R_1$ is selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle and heterocycle groups are each optionally substituted;

$R_7$ is absent or is selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted; wherein $R_2$, $R_3$ and $R_7$ are not all H;

$R_8$ is selected from the group consisting of a side chain of a natural amino acid and a side chain of an unnatural amino acid, wherein the natural amino acid and the unnatural amino acid is either in the D or L form;

X is a 5 or 6-membered heterocycle or a linker comprising a hydrophilic moiety selected from the group consisting of hydroxyl, carbonyl, amide (—C(O)NH—), sulfonamide, sulfonate, phosphate, polar amino acid moiety, PEG moiety, sugar mimetic, and sugar moiety, or a combination thereof;

Y is a 5 or 6-membered heterocycle, or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

where at least one of X and Y is a 5 or 6-membered heterocycle; and w is 1, 2, 3, 4, or 5;

wherein any one of X, Y, $R_2$, $R_3$, and $R_7$ comprises a radionuclide selected from the group consisting of positron or gamma emitters.

2. The cyclopeptide of paragraph 1 wherein Y is a 5 or 6-membered heterocycle; and X is a linker either comprising a sugar mimetic selected from the group consisting of a 4 to 6-membered carbocycle substituted with at least one hydroxyl group and a 5- to 6-membered heterocycle substituted with at least one hydroxyl group or comprising a sugar moiety selected from the group consisting of glucose and galactose.

3. The cyclopeptide of paragraphs 1 or 2 wherein:

Y is a 5 or 6-membered heterocycle;

X is selected from the group consisting of:

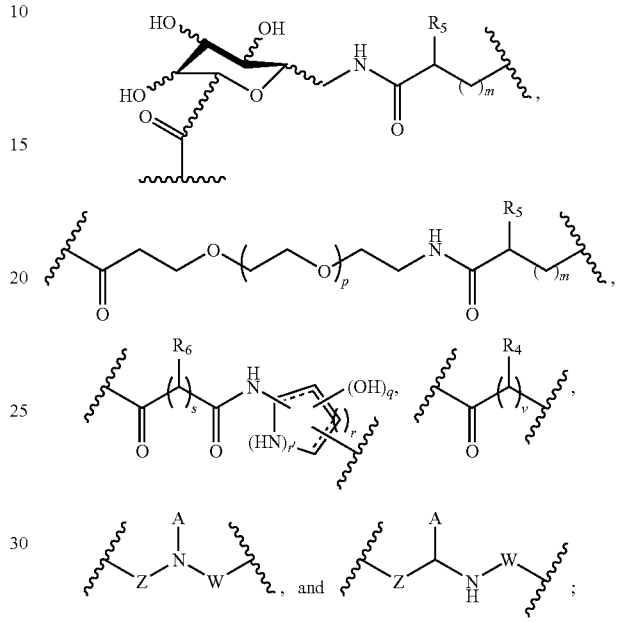

wherein Z is selected from the group consisting of:

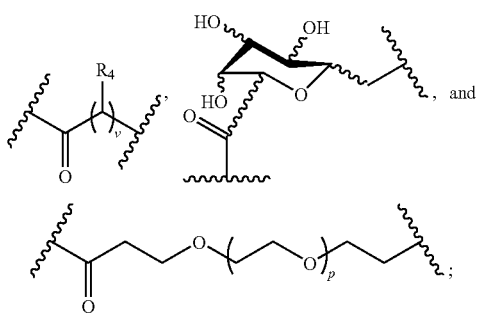

W is selected from the group consisting of:

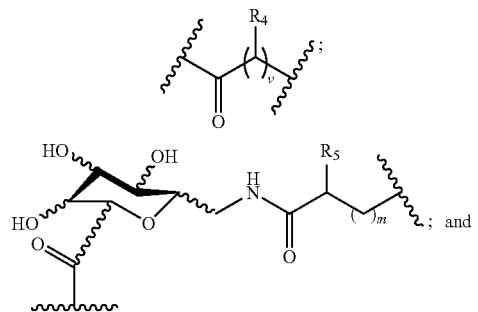

-continued

[chemical structure: PEG linker with R5]

A is selected from the group consisting of:

[cyclopeptide structure with R1, R8, R4, OH, NH, guanidine group]

[cyclopeptide structure with sugar moiety]

[cyclopeptide structure with PEG chain]

[cyclopeptide structure with R1, R8]

each $R_1$ is independently selected from the group consisting of a side chain of a natural amino acid and a side chain of an unnatural amino acid, wherein the natural amino acid and the unnatural amino acid is either in the D or L form;

each $R_8$ is independently selected from the group consisting of a side chain of a natural amino acid and a side chain of an unnatural amino acid, wherein the natural amino acid and the unnatural amino acid is either in the D or L form;

each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted;

each $R_6$ is independently selected from the group consisting of —H, —OH, $C_1$-$C_6$ alkyl, $C_2$-$C_6$ alkenyl, $C_2$-$C_6$ alkynyl, $C_1$-$C_6$ alkyloxy, aryl-($C_1$-$C_6$ alkylene)-, hydroxy-$C_1$-$C_6$-alkyl, and $C_1$-$C_6$-alkoxy-$C_1$-$C_6$-alkyl, wherein the alkyl, alkenyl, alkynyl, alkyloxy, and aryl-alkylene groups are each optionally substituted;

each v is 0, 1, 2, 3, or 4;

m is 0, 1, 2, 3 or 4;

p is an integer between 1 and 110;

q is 1, 2, 3 or 4;

r is 1, 2 or 3;

r' is 0 or 1;

s is 1, 2, 3 or 4; and the radionuclide is selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$;

wherein the configuration of the chiral centers may be R or S or mixtures thereof.

4. The cyclopeptide of paragraphs 1-3 wherein:

$R_1$ is a side chain of a natural amino acid;

$R_8$ is a side chain of a natural amino acid;

$R_7$ is absent;

X is

[two chemical structures showing Z-N-W linkages with A substituent]

Y is 1,2,3-triazolyl; and $R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{75}Br$, $^{124}I$, $^{125}I$ and $^{131}I$.

5. A cyclopeptide of formula II:

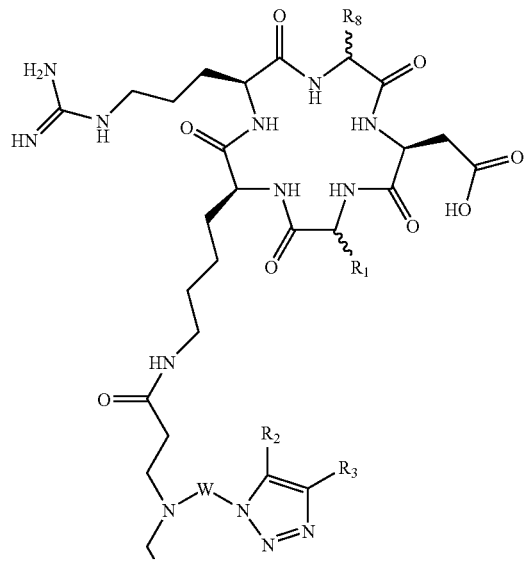

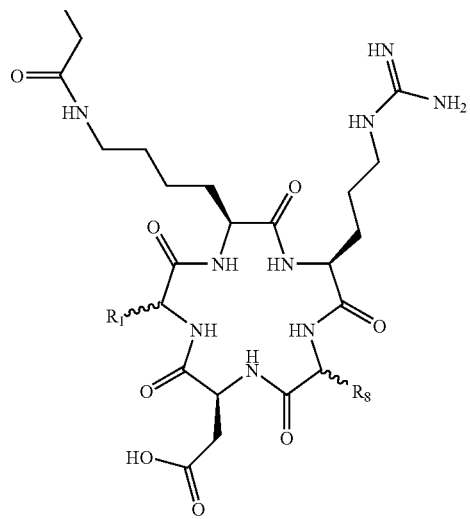

wherein:

each $R_1$ is independently selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}$C, $^{13}$N, $^{15}$O, $^{18}$F, $^{75}$Br, $^{124}$I, $^{125}$I and $^{131}$I; and

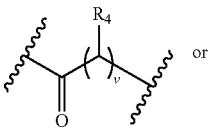

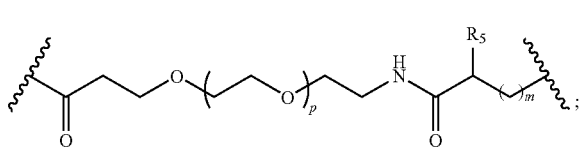

W is where p is an integer between 0 and 15;

v is 0, 1, 2, or 3;

m is 0, 1 or 2;

each $R_4$ is independently selected from the group consisting of —H, $C_1$-$C_6$ alkyl, $C_2$-$C_6$ alkenyl, and $C_2$-$C_6$ alkynyl, wherein the alkyl, alkenyl, and alkynyl groups are each optionally substituted;

$R_5$ is selected from the group consisting of —H, $C_1$-$C_6$ alkyl, $C_2$-$C_6$ alkenyl, and $C_2$-$C_6$ alkynyl, wherein the alkyl, alkenyl and alkynyl groups are each optionally substituted and wherein the configuration of the chiral center that is substituted with the $R_5$ substituent may be R or S or mixtures thereof; and each $R_8$ is independently selected from the group consisting of a side chain of a natural amino acid and a side chain of an unnatural amino acid, wherein the natural amino acid and the unnatural amino acid is either in the D or L form.

6. The cyclopeptide of paragraph 5 wherein:

each $R_1$ is benzyl;

$R_2$ is H;

$R_3$ is an optionally substituted $C_1$-$C_6$ alkyl comprising a radionuclide selected from the group consisting of $^{11}$C, $^{13}$N, $^{15}$O, $^{18}$F, $^{75}$Br, $^{124}$I, $^{125}$I and $^{131}$I;

$R_8$ is a side chain of a natural amino acid; and

W is

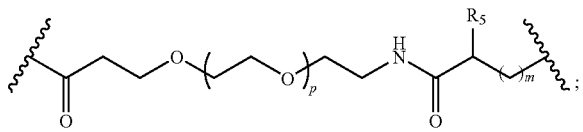

where p is 0, 1, 2, 3, 4, or 5.

7. A cyclopeptide of formula III:

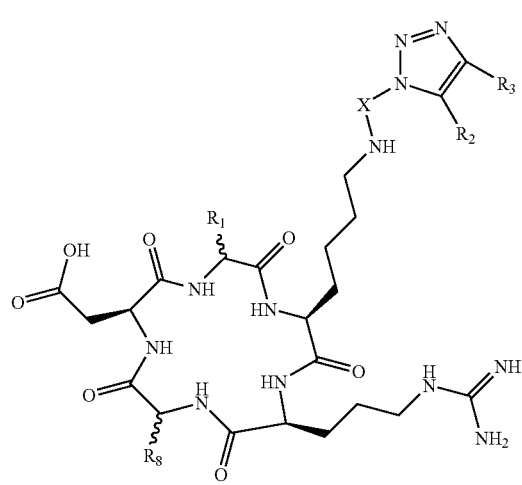

III wherein:

$R_1$ is selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted;

wherein $R_2$ and $R_3$ are not both H; and either $R_2$ or $R_3$, or both $R_2$ and $R_3$ comprise a radionuclide selected from the group consisting of positron or gamma emitters;

$R_8$ is selected from the group consisting of a side chain of a natural amino acid and a side chain of an unnatural amino acid, wherein the natural amino acid and the unnatural amino acid is either in the D or L form; and X is a linker comprising a hydrophilic moiety selected from the group consisting of hydroxyl, carbonyl, amide (—C(O)NH—), sulfonamide, sulfonate, phosphate, polar amino acid moiety, PEG moiety, sugar mimetic and sugar moiety, or a combination thereof.

8. The cyclopeptide of paragraphs 7 wherein $R_1$ is a side chain of a natural amino acid; $R_8$ is a side chain of a natural amino acid; $R_2$ is hydrogen; and $R_3$ comprises a radionuclide selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$.

9. The cyclopeptide of paragraph 7 or 8 wherein $R_1$ is benzyl; $R_8$ is a side chain of a natural amino acid; and $R_3$ comprises a radionuclide selected from the group consisting of $^{11}C$, $^{13}N$, $^{15}O$, $^{18}F$, $^{124}I$, $^{125}I$, $^{131}I$ and $^{75}Br$.

10. The cyclopeptide of paragraph 7-9 wherein:

$R_1$ is a side chain of a natural amino acid;

X is selected from the group consisting of:

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle and heterocycle groups are each optionally substituted;

each $R_6$ is independently selected from the group consisting of —H, —OH, $C_1$-$C_6$ alkyl, $C_2$-$C_6$ alkenyl, $C_2$-$C_6$ alkynyl, $C_1$-$C_6$ alkyloxy, aryl-($C_1$-$C_6$ alkylene)-, hydroxy-$C_1$-$C_6$-alkyl, and $C_1$-$C_6$-alkoxy-$C_1$-$C_6$-alkyl, wherein the alkyl, alkenyl, alkynyl, alkyloxy, and aryl-alkylene groups are each optionally substituted;

$R_8$ is a side chain of a natural amino acid;

v is 0, 1, 2, 3, or 4;

m is 0, 1, 2, 3 or 4;

p is an integer between 1 and 110;

q is 1, 2, 3 or 4;

r is 1, 2 or 3;

r' is 0 or 1 s is 1, 2, 3 or 4; and the radionuclide is selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$;

where the configuration of the chiral centers may be R or S or mixtures thereof.

11. The cyclopeptide of paragraphs 7-10 wherein:
X is

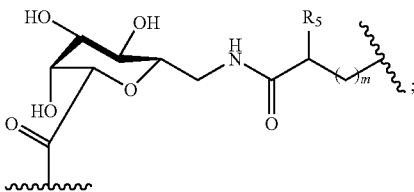

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{75}Br$, $^{124}I$, $^{125}I$ and $^{131}I$;

$R_5$ is selected from the group consisting of —H, $C_1$-$C_6$ alkyl, $C_2$-$C_6$ alkenyl, and $C_2$-$C_6$ alkynyl, wherein the alkyl, alkenyl and alkynyl groups are each optionally substituted and wherein the configuration of the chiral center that is substituted with the $R_5$ substituent may be R or S or mixtures thereof; and m is 0, 1 or 2.

12. The cyclopeptide of paragraphs 7-11, wherein:
$R_2$ is hydrogen;
$R_3$ is selected from the group consisting of $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein $R_3$ comprises a radionuclide selected from the group consisting of $^{11}C$, $^{13}N$, $^{15}O$, and $^{18}F$;
$R_5$ is hydrogen; and
m is 0.

13. The cyclopeptide of paragraph 7-10, wherein:
$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted; wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{75}Br$, $^{124}I$, $^{125}I$, and $^{131}I$;
X is

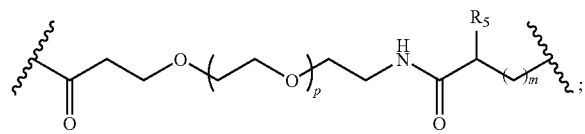

where $R_5$ is selected from the group consisting of —H, $C_1$-$C_6$ alkyl, $C_2$-$C_6$ alkenyl, and $C_2$-$C_6$ alkynyl, wherein the alkyl, alkenyl and alkynyl groups are each optionally substituted and wherein the configuration of the chiral center that is substituted with the $R_5$ substituent may be R or S or mixtures thereof;

m is 0, 1, or 2; and p is an integer between 1 and 90.

14. The cyclopeptide of paragraph 13, wherein:
$R_2$ is hydrogen;
$R_3$ is selected from the group consisting of $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein $R_3$ comprises a radionuclide selected from the group consisting of $^{11}C$, $^{13}N$, $^{15}O$ and $^{18}F$;
$R_5$ is hydrogen;
m is 0; and
p is an integer between 1 and 15.

15. The cyclopeptide of paragraph 7-10 wherein:
X is

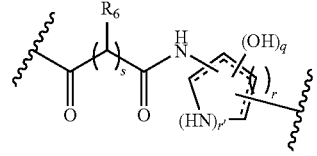

where each $R_6$ is independently selected from the group consisting of —H, —OH, $C_1$-$C_6$ alkyl, $C_2$-$C_6$ alkenyl, $C_1$-$C_6$ alkyloxy, hydroxy-$C_1$-$C_6$-alkyl, and $C_1$-$C_6$-alkoxy-$C_1$-$C_6$-alkyl, wherein the alkyl, alkenyl, and alkyloxy groups are each optionally substituted;

q is 2, 3 or 4;
r is 2 or 3;
r' is 0; and
s is 1 or 2.

16. The cyclopeptide of paragraph 7-10 wherein:
X is where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted; and v is 1, 2, 3, or 4.

17. A radiolabeled cyclopeptide of formula IV:

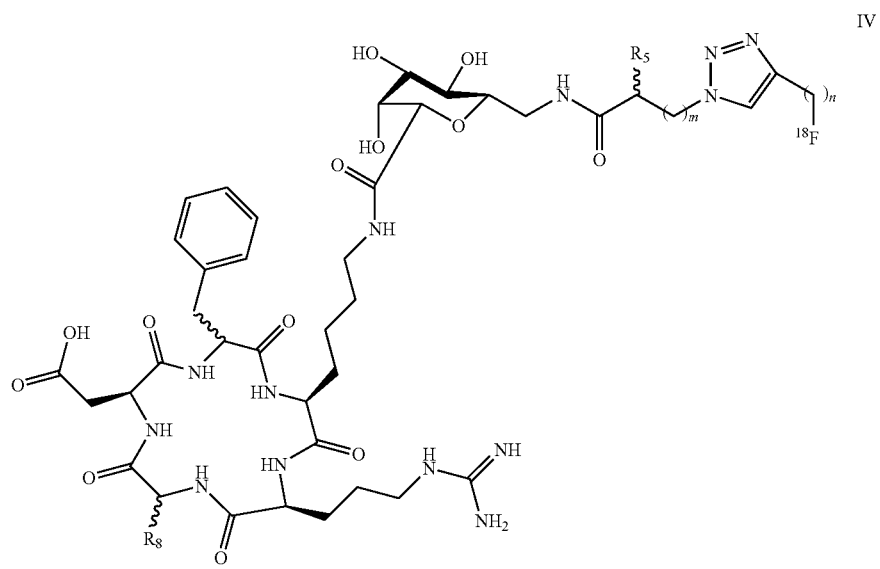

wherein:

$R_5$ is selected from the group consisting of H, $C_1$-$C_6$ alkyl, $C_2$-$C_6$ alkenyl, $C_2$-$C_6$ alkynyl, $C_1$-$C_6$ alkyloxy, aryl, —($C_1$-$C_6$ alkylene)-aryl, 3- to 7-membered carbocycle, 3- to 7-membered heterocycle, hydroxy-$C_1$-$C_6$-alkyl, and $C_1$-$C_6$-alkoxy-$C_1$-$C_6$-alkyl; wherein the alkyl, alkenyl, alkynyl, alkyloxy, aryl, carbocycle and heterocycle groups are each optionally substituted;

$R_8$ is selected from the group consisting of a side chain of a natural amino acid and a side chain of an unnatural amino acid, wherein the natural amino acid and the unnatural amino acid is either in the D or L form;

wherein the chiral centers attached to ⁓bonds are R or S or mixtures thereof;

m is 0, 1, 2, 3 or 4; and
n is 1, 2, 3, 4 or 5.

18. The cyclopeptide of paragraph 17, wherein:

$R_5$ is selected from the group consisting of H, $C_1$-$C_4$ alkyl, $C_2$-$C_4$ alkenyl, and $C_2$-$C_4$ alkynyl, wherein the alkyl, alkenyl and alkynyl groups are each optionally substituted;

wherein the chiral center in the cyclic peptide is R configured and the chiral center bearing the $R_5$ residue is R or S or mixtures thereof;

m is 0, 1 or 2; and
n is 1, 2, 3 or 4.

19. The cyclopeptide of paragraph 17 or 18, wherein:

$R_5$ is selected from the group consisting of —H, and an optionally substituted $C_1$-$C_4$ alkyl;

m is 0 or 1; and n is 2, 3 or 4.

20. A radiolabeled cyclopeptide selected from the group consisting of:

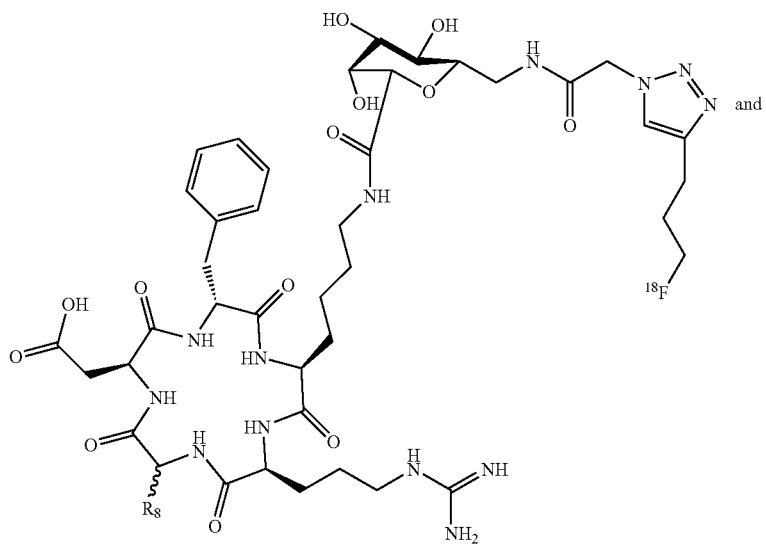

and

-continued
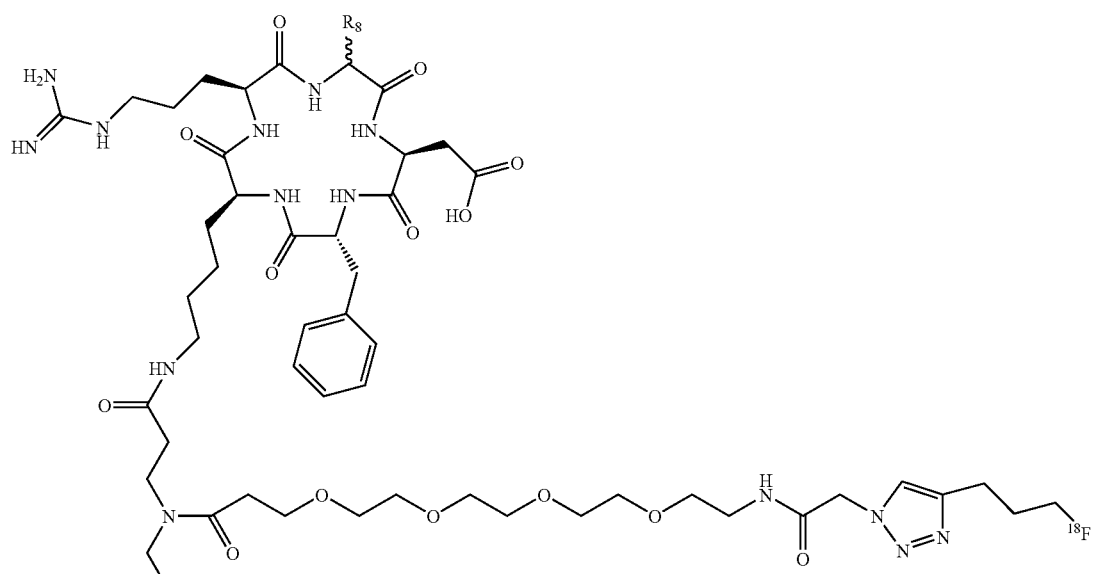
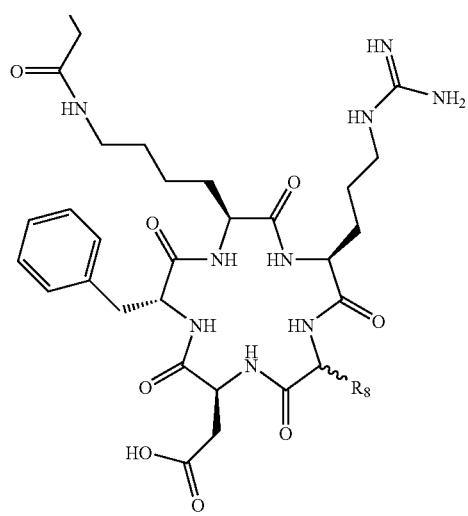
wherein each $R_8$ is selected from the group consisting of a side chain of a natural amino acid and a side chain of an unnatural amino acid, wherein the natural amino acid and the unnatural amino acid is either in the D or L form.

21. A pharmaceutical composition comprising a radiolabeled cyclopeptide of formula I:

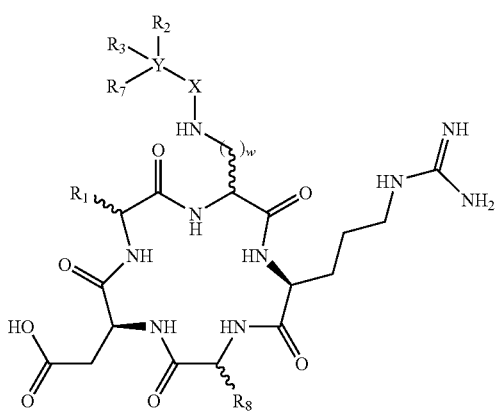

wherein:

$R_1$ is selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted;

$R_7$ is absent or is selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted; wherein $R_2$, $R_3$ and $R_7$ are not all H;

$R_8$ is selected from the group consisting of a side chain of a natural amino acid and a side chain of an unnatural amino acid, wherein the natural amino acid and the unnatural amino acid is either in the D or L form;

X is a 5 or 6-membered heterocycle or a linker comprising a hydrophilic moiety selected from the group consisting of hydroxyl, carbonyl, amide (—C(O)NH—), sulfonamide, sulfonate, phosphate, polar amino acid moiety, PEG moiety, sugar mimetic, and sugar moiety, or a combination thereof;

Y is a 5 or 6-membered heterocycle, or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

where at least one of X and Y, but not both X and Y is a 5 or 6-membered heterocycle; and w is 1, 2, 3, 4, or 5;

wherein any one of X, Y, $R_2$, $R_3$, and $R_7$ comprises a radionuclide selected from the group consisting of positron or gamma emitters;

and a pharmaceutically acceptable carrier.

22. A pharmaceutical composition comprising a radiolabeled cyclopeptide of formula II or formula III:

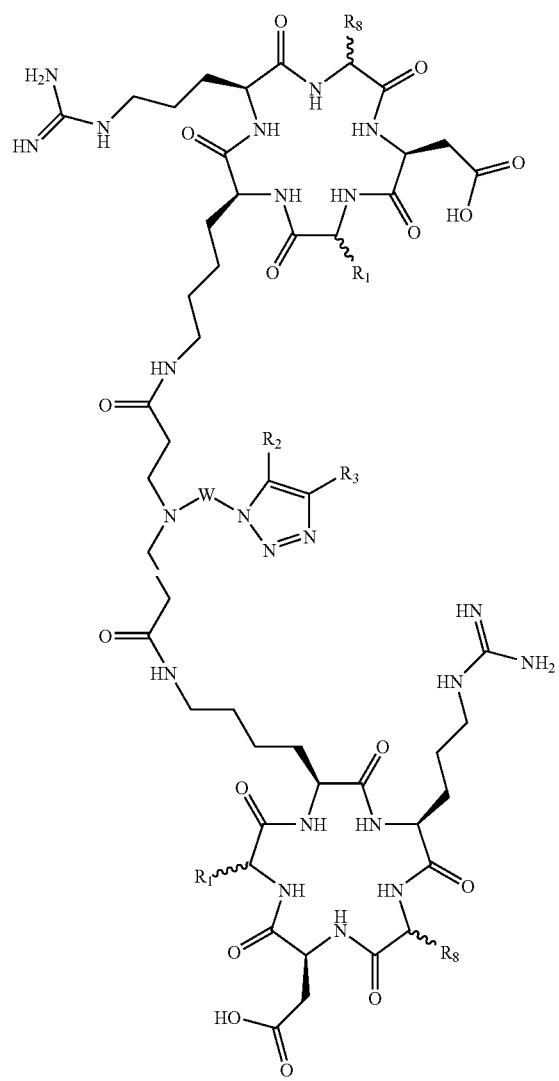

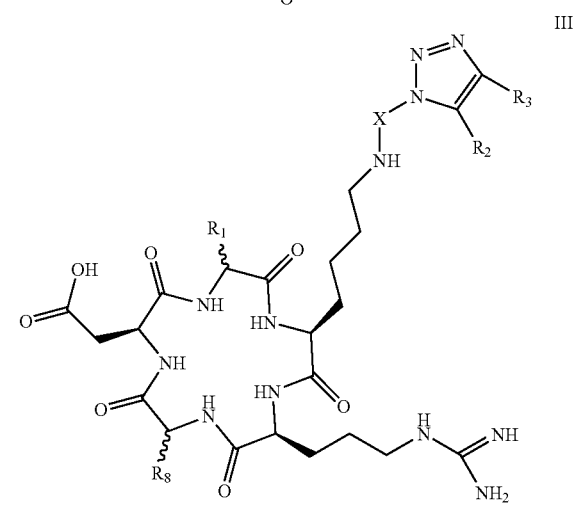

wherein:

each $R_1$ is independently selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I, $^{131}$I, $^{99}$Tc, $^{75}$Br, $^{153}$Gd and $^{32}$P;

each of X and W is selected from the group consisting of:

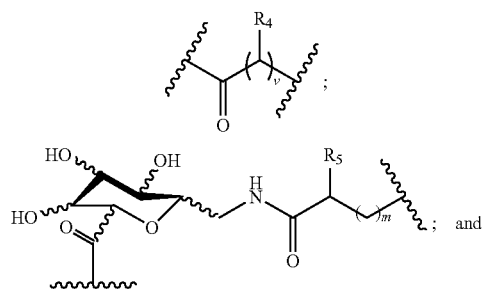

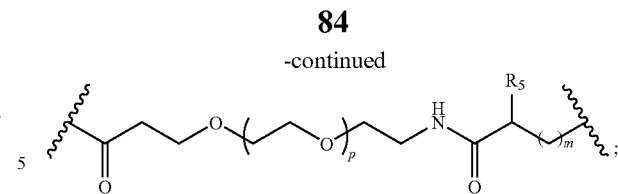

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted;

each $R_8$ is independently selected from the group consisting of a side chain of a natural amino acid and a side chain of an unnatural amino acid, wherein the natural amino acid and the unnatural amino acid is either in the D or L form;

v is 0, 1, 2, 3, or 4;

m is 0, 1, 2, 3 or 4; and p is an integer between 1 and 25;

wherein the configuration of the chiral centers may be R or S or mixtures thereof; and a pharmaceutically acceptable carrier.

23. A pharmaceutical composition comprising a radiolabeled cyclopeptide selected from the group consisting of:

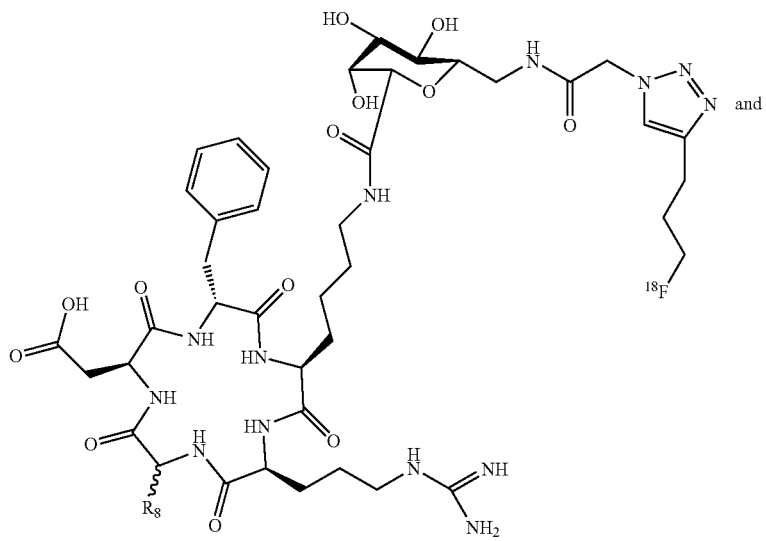

and

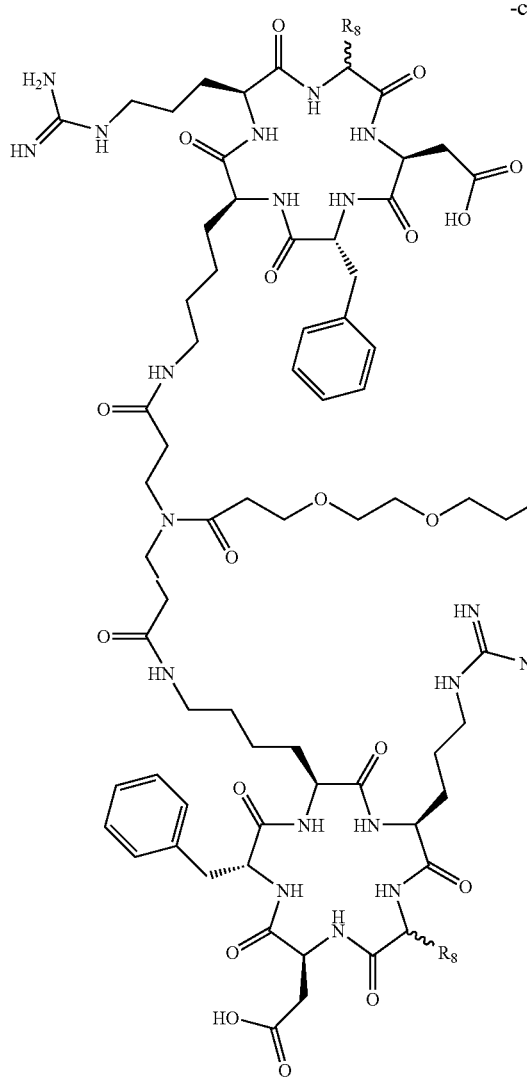

wherein:

each $R_8$ is independently selected from the group consisting of a side chain of a natural amino acid and a side chain of an unnatural amino acid, wherein the natural amino acid and the unnatural amino acid is either in the D or L form;

and a pharmaceutically acceptable carrier.

24. A method of monitoring the level of integrin $\alpha_v\beta_3$ or visualizing integrin $\alpha_v\beta_3$ expression within a body of a patient, the method comprising: (a) administering to the patient a radiolabeled cyclopeptide; and (b) employing a nuclear imaging technique selected from the group consisting of positron emission tomography (PET) and single photon emission computed tomography (SPECT) for monitoring or visualizing a distribution of the radiolabeled cyclopeptide within the body or within a portion thereof; wherein the radiolabeled cyclopeptide is of formula I:

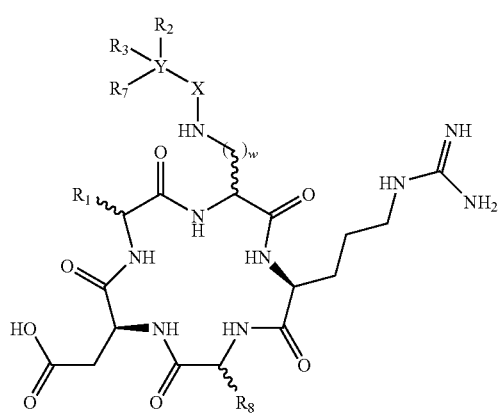

wherein
$R_1$ is selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted;

$R_7$ is absent or is selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted; wherein $R_2$, $R_3$ and $R_7$ are not all H;

$R_8$ is selected from the group consisting of a side chain of a natural amino acid and a side chain of an unnatural amino acid, wherein the natural amino acid and the unnatural amino acid is either in the D or L form;

X is a 5 or 6-membered heterocycle or a linker comprising a hydrophilic moiety selected from the group consisting of hydroxyl, carbonyl, amide (—C(O)NH—), sulfonamide, sulfonate, phosphate, polar amino acid moiety, PEG moiety, sugar mimetic, and sugar moiety, or a combination thereof;

Y is a 5 or 6-membered heterocycle or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

where at least one of X and Y, but not both X and Y is a 5 or 6-membered heterocycle; and w is 1, 2, 3, 4, or 5;

wherein any one of X, Y, $R_2$, $R_3$, and $R_7$ comprises a radionuclide selected from the group consisting of positron or gamma emitters.

25. A method of monitoring the level of integrin $\alpha_v\beta_3$ or visualizing integrin $\alpha_v\beta_3$ expression within a body of a patient, the method comprising: (a) administering to the patient a radiolabeled cyclopeptide; and (b) employing a nuclear imaging technique selected from the group consisting of positron emission tomography (PET) and single photon emission computed tomography (SPECT) for monitoring or visualizing a distribution of the radiolabeled cyclopeptide within the body or within a portion thereof; wherein the radiolabeled cyclopeptide is of formula II or formula III:

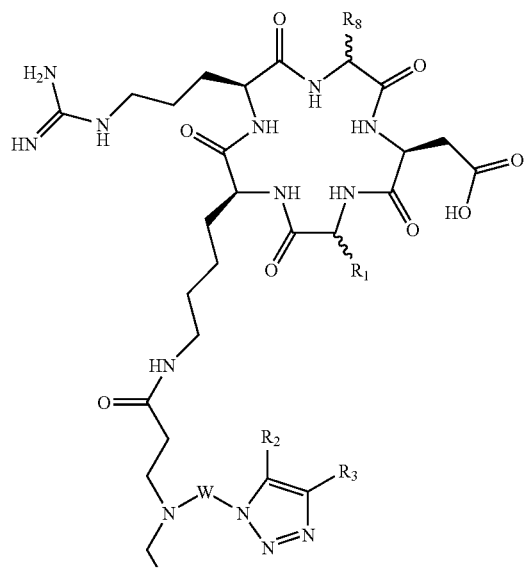

II

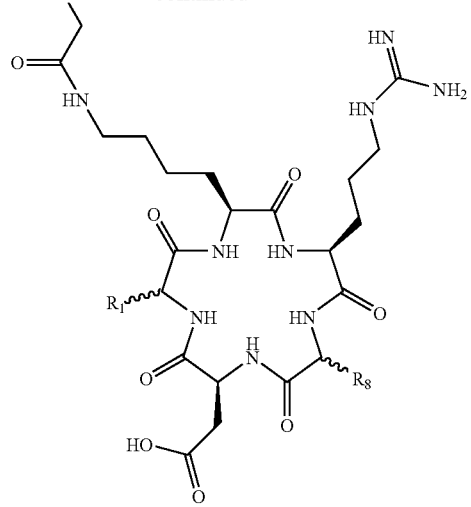

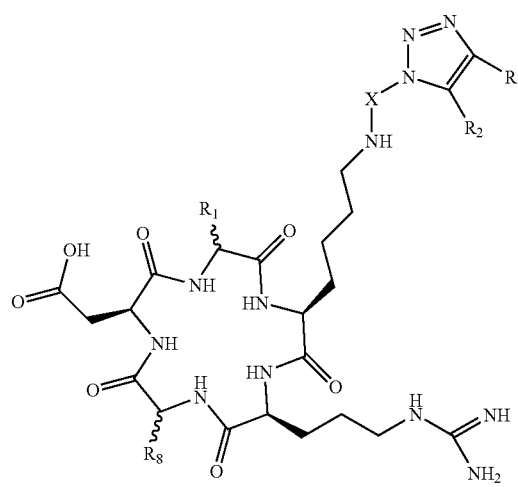

III wherein each $R_1$ is independently selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I, $^{131}$I, $^{99}$Tc, $^{75}$Br, $^{153}$Gd and $^{32}$P;

each of X and W is selected from the group consisting of:

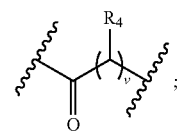

-continued

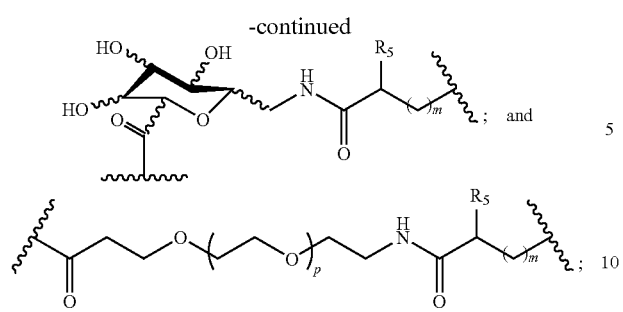

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted;

each $R_8$ is independently selected from the group consisting of a side chain of a natural amino acid and a side chain of an unnatural amino acid, wherein the natural amino acid and the unnatural amino acid is either in the D or L form;

wherein the configuration of the chiral centers may be R or S or mixtures thereof;

v is 0, 1, 2, 3, or 4;

m is 0, 1, 2, 3 or 4; and p is an integer between 1 and 25.

26. A method of monitoring the level of integrin $\alpha_v\beta_3$ or visualizing integrin $\alpha_v\beta_3$ expression within a body of a patient, the method comprising: (a) administering to the patient a radiolabeled cyclopeptide; and (b) employing a nuclear imaging technique selected from the group consisting of positron emission tomography (PET) and single photon emission computed tomography (SPECT) for monitoring or visualizing a distribution of the radiolabeled cyclopeptide within the body or within a portion thereof; wherein the radiolabeled cyclopeptide is selected from the group consisting of:

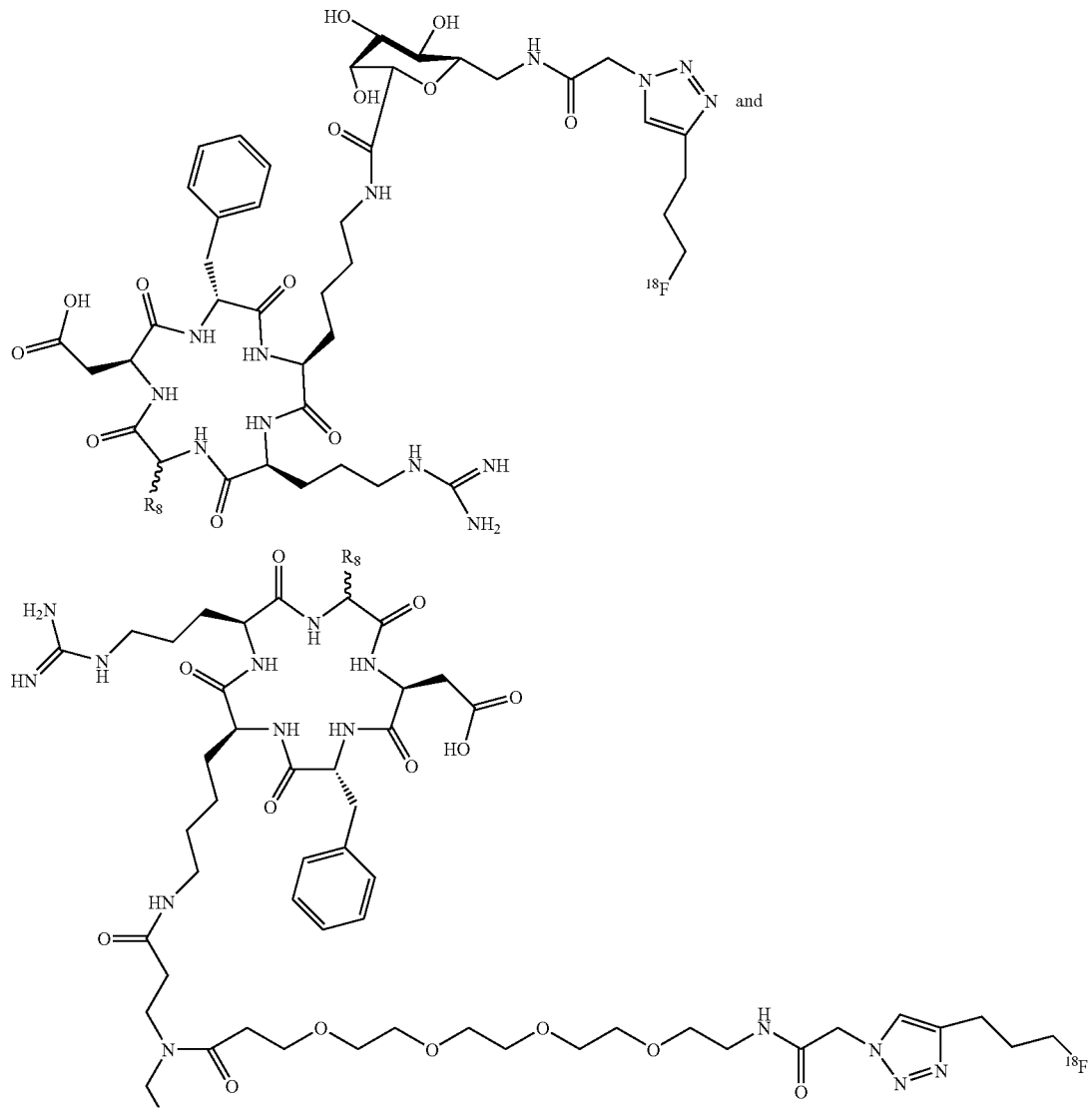

-continued

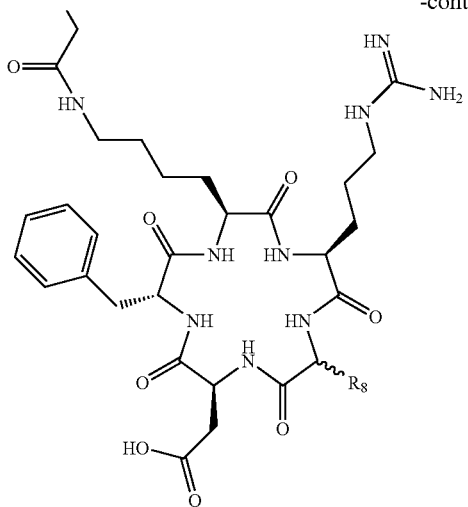

wherein:

each $R_8$ is independently selected from the group consisting of a side chain of a natural amino acid and a side chain of an unnatural amino acid, wherein the natural amino acid and the unnatural amino acid is either in the D or L form.

27. A method for imaging of blood vessel growth in solid tumors based on expression of integrin $\alpha_v\beta_3$ within the body of a patient, the method comprising: (a) administering to the patient a radiolabeled cyclopeptide; (b) employing a nuclear imaging technique selected from the group consisting of positron emission tomography (PET) and single photon emission computed tomography (SPECT) for imaging a distribution of the radiolabeled cyclopeptide within the body or within a portion thereof; and c) correlating the distribution of the radiolabeled cyclopeptide to the growth of blood vessels in solid tumors, wherein the radiolabeled cyclopeptide is of formula I:

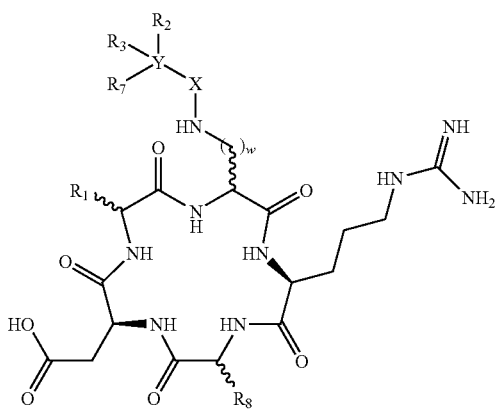

wherein:

$R_1$ is selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted;

$R_7$ is absent or is selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted; wherein $R_2$, $R_3$ and $R_7$ are not all H;

$R_8$ is selected from the group consisting of a side chain of a natural amino acid and a side chain of an unnatural amino acid, wherein the natural amino acid and the unnatural amino acid is either in the D or L form;

X is a 5 or 6-membered heterocycle or a linker comprising a hydrophilic moiety selected from the group consisting of hydroxyl, carbonyl, amide (—C(O)NH—), sulfonamide, sulfonate, phosphate, polar amino acid moiety, PEG moiety, sugar mimetic, and sugar moiety, or a combination thereof;

Y is a 5 or 6-membered heterocycle, or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

where at least one of X and Y, but not both X and Y is a 5 or 6-membered heterocycle; and w is 1, 2, 3, 4, or 5;

wherein any one of X, Y, $R_2$, $R_3$, and $R_7$ comprises a radionuclide selected from the group consisting of positron or gamma emitters.

28. A method for imaging of blood vessel growth in solid tumors based on expression of integrin $\alpha_v\beta_3$ within the body of a patient, the method comprising: (a) administering to the patient a radiolabeled cyclopeptide; (b) employing a nuclear imaging technique selected from the group consisting of positron emission tomography (PET) and single photon emission computed tomography (SPECT) for imaging a distribution of the radiolabeled cyclopeptide within the body or within a portion thereof; and c) correlating the distribution of the radiolabeled cyclopeptide to the growth of blood vessels in solid tumors, wherein the radiolabeled cyclopeptide is of formula II or formula III:

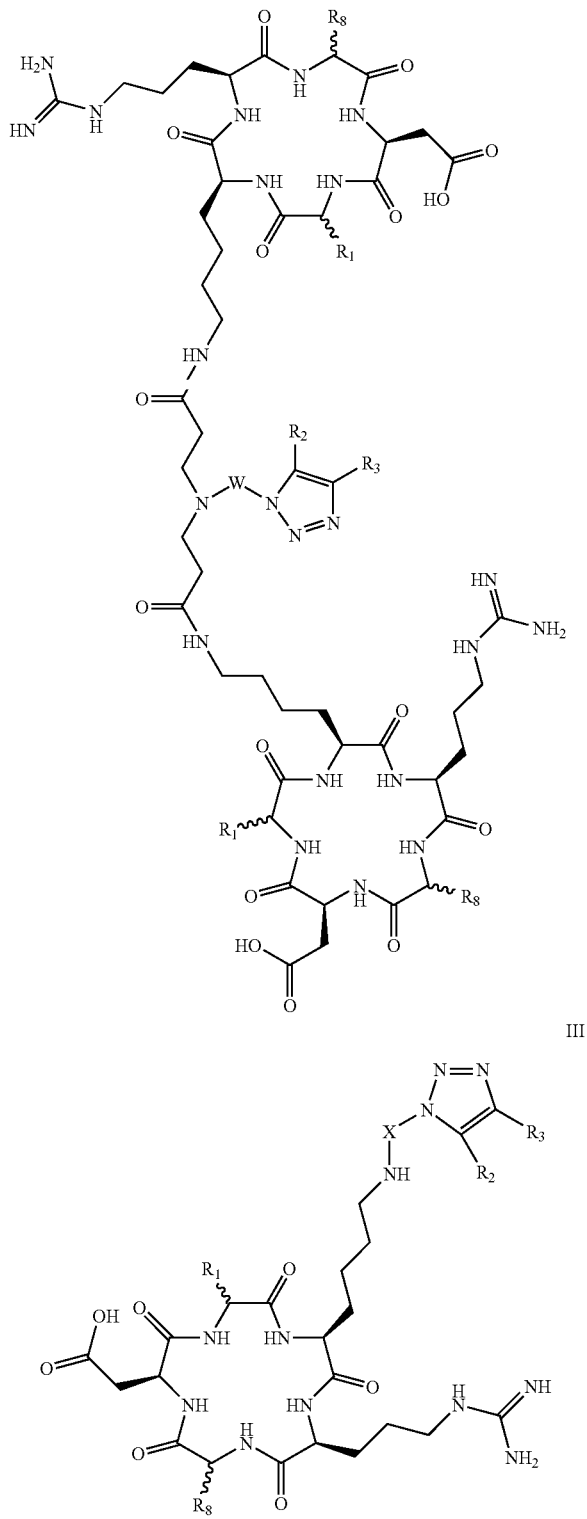

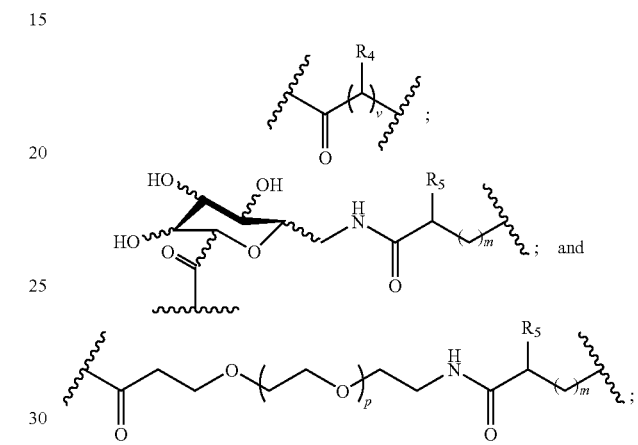

wherein:

each $R_1$ is independently selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$;

each of X and W is selected from the group consisting of:

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted;

each $R_8$ is independently selected from the group consisting of a side chain of a natural amino acid and a side chain of an unnatural amino acid, wherein the natural amino acid and the unnatural amino acid is either in the D or L form;

wherein the configuration of the chiral centers may be R or S or mixtures thereof;

v is 0, 1, 2, 3, or 4;

m is 0, 1, 2, 3 or 4; and p is an integer between 1 and 25.

29. A method for imaging of blood vessel growth in solid tumors based on expression of integrin $\alpha_v\beta_3$ within the body of a patient, the method comprising: (a) administering to the patient a radiolabeled cyclopeptide; (b) employing a nuclear imaging technique selected from the group consisting of positron emission tomography (PET) and single photon emission computed tomography (SPECT) for imaging a distribution of the radiolabeled cyclopeptide within the body or within a portion thereof; and c) correlating the distribution of the radiolabeled cyclopeptide to the growth of blood vessels in solid tumors, wherein the radiolabeled cyclopeptide is selected from the group consisting of:

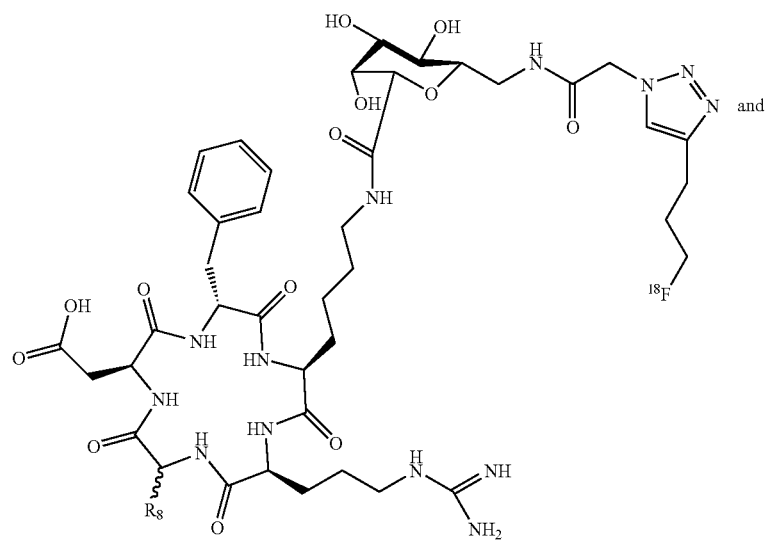
and
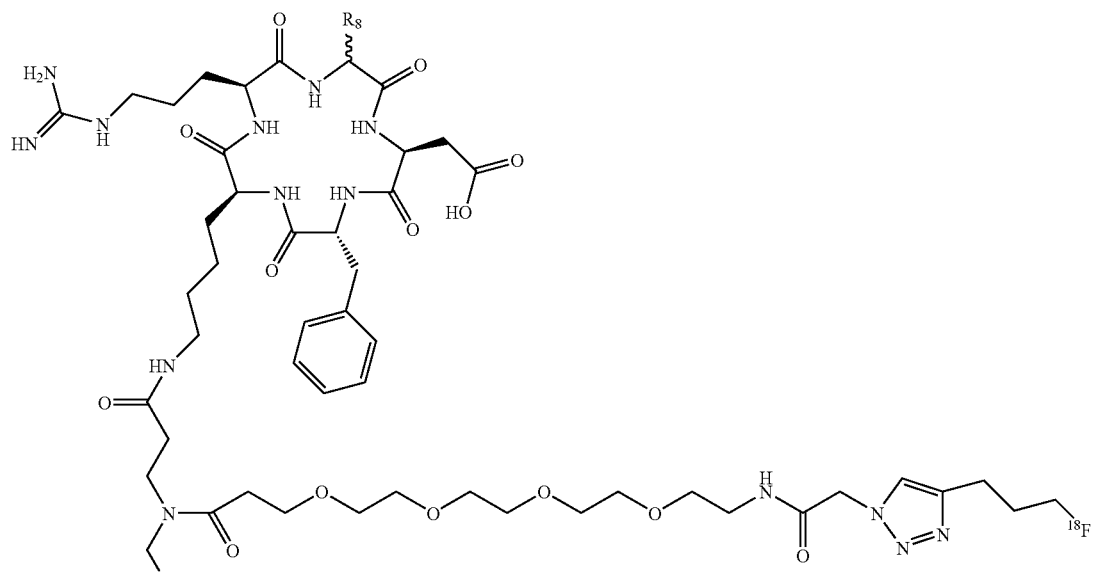
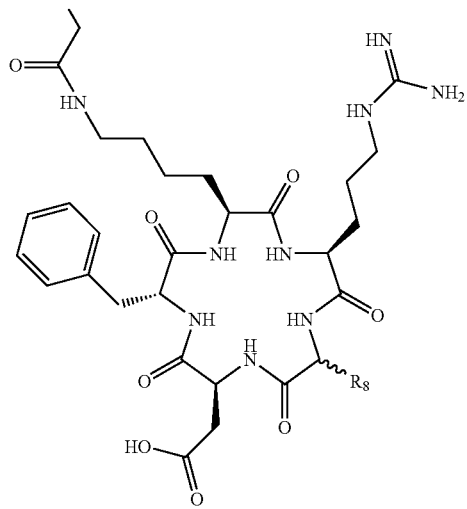

wherein:
each $R_8$ is independently selected from the group consisting of a side chain of a natural amino acid and a side chain of an unnatural amino acid, wherein the natural amino acid and the unnatural amino acid is either in the D or L form.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A cyclopeptide of formula I:

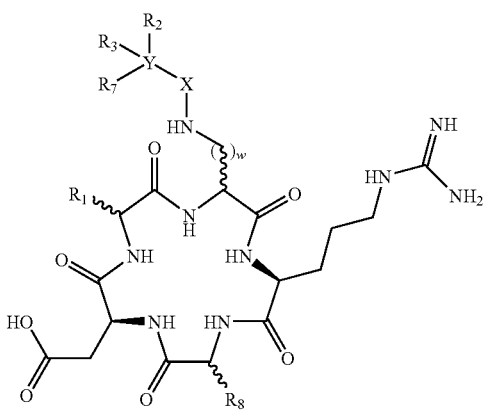

wherein:
- $R_1$ is selected from the group consisting of a side chain of a natural amino acid and a side chain of an unnatural amino acid, wherein the natural amino acid and the unnatural amino acid is either in the D or L form;
- $R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle and heterocycle groups are each optionally substituted;
- $R_7$ is absent or is selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted; wherein $R_2$, $R_3$ and $R_7$ are not all H;
- $R_8$ is selected from the group consisting of a side chain of a natural amino acid and a side chain of an unnatural amino acid, wherein the natural amino acid and the unnatural amino acid is either in the D or L form;
- X is a 5 or 6-membered heterocycle or a linker comprising a hydrophilic moiety selected from the group consisting of hydroxyl, carbonyl, amide (—C(O)NH—), sulfonamide, sulfonate, phosphate, polar amino acid moiety, PEG moiety, sugar mimetic, and sugar moiety, or a combination thereof;
- Y is a 5 or 6-membered heterocycle, or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;
- where at least one of X and Y is a 5 or 6-membered heterocycle; and
- w is 1, 2, 3, 4, or 5;
- wherein any one of X, Y, $R_2$, $R_3$, and $R_7$ comprises a radionuclide selected from the group consisting of positron or gamma emitters.

2. The cyclopeptide of claim 1 wherein Y is a 5- or 6-membered heterocycle; and X is a linker either comprising a sugar mimetic selected from the group consisting of a 4 to 6-membered carbocycle substituted with at least one hydroxyl group and a 5- to 6-membered heterocycle substituted with at least one hydroxyl group or comprising a sugar moiety selected from the group consisting of glucose and galactose.

3. The cyclopeptide of claim 1 wherein:
Y is a 5 or 6-membered heterocycle;
X is selected from the group consisting of:

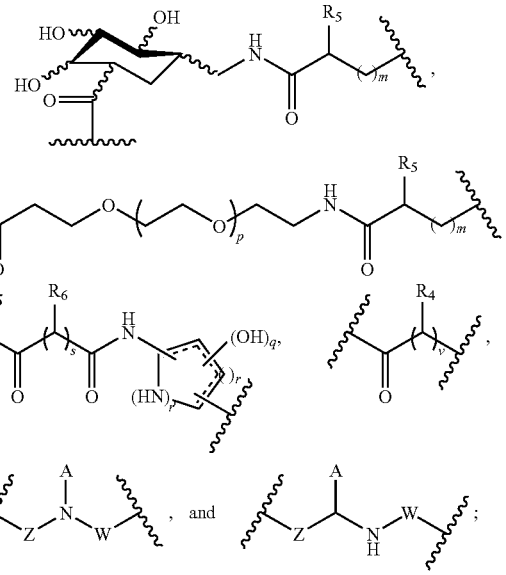

wherein Z is selected from the group consisting of:

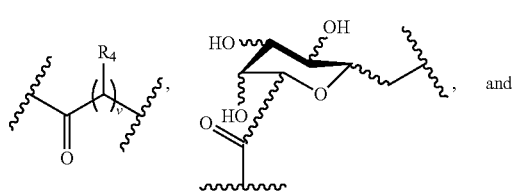

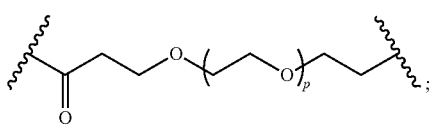

W is selected from the group consisting of:

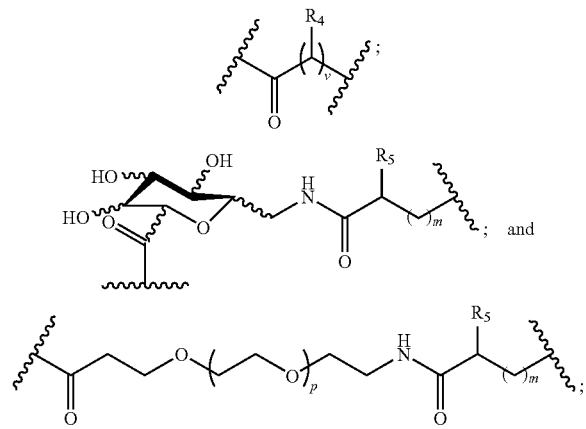

A is selected from the group consisting of:

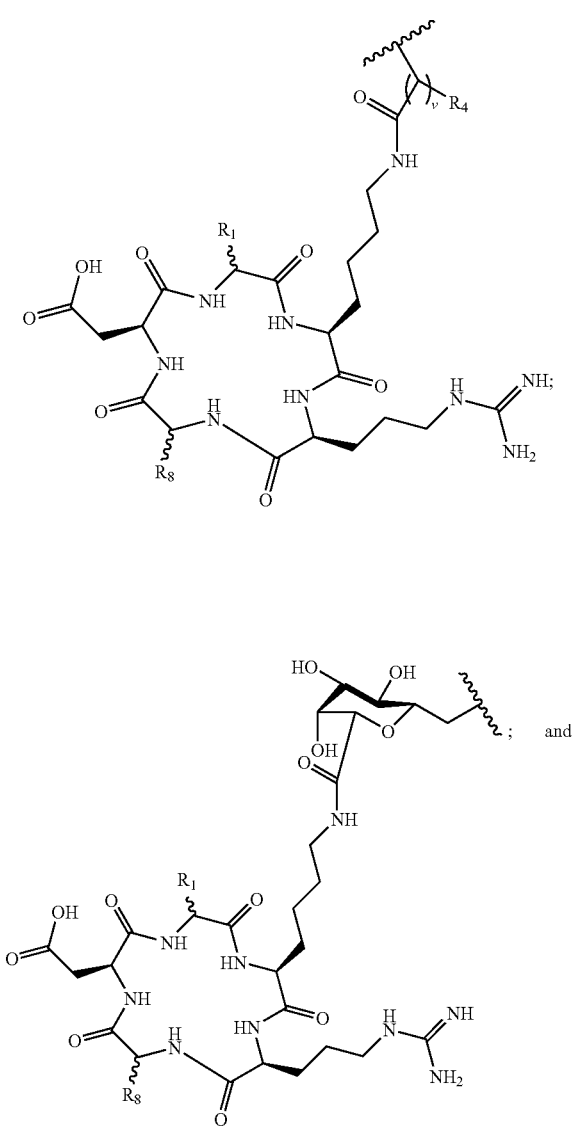

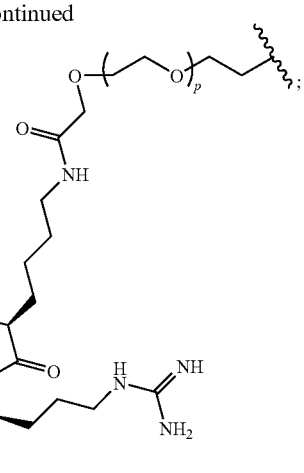

each $R_1$ is independently selected from the group consisting of a side chain of a natural amino acid and a side chain of an unnatural amino acid, wherein the natural amino acid and the unnatural amino acid is either in the D or L form;

each $R_8$ is independently selected from the group consisting of a side chain of a natural amino acid and a side chain of an unnatural amino acid, wherein the natural amino acid and the unnatural amino acid is either in the D or L form;

each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted;

each $R_6$ is independently selected from the group consisting of —H, —OH, $C_1$-$C_6$ alkyl, $C_2$-$C_6$ alkenyl, $C_2$-$C_6$ alkynyl, $C_1$-$C_6$ alkyloxy, aryl-($C_1$-$C_6$ alkylene)-, hydroxy-$C_1$-$C_6$-alkyl, and $C_1$-$C_6$-alkoxy-$C_1$-$C_6$-alkyl, wherein the alkyl, alkenyl, alkynyl, alkyloxy, and aryl-alkylene groups are each optionally substituted;

each v is 0, 1, 2, 3, or 4;
m is 0, 1, 2, 3 or 4;
p is an integer between 1 and 110;
q is 1, 2, 3 or 4;
r is 1, 2 or 3;
r' is 0 or 1;
s is 1, 2, 3 or 4; and
the radionuclide is selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$;
wherein the configuration of the chiral centers may be R or S or mixtures thereof.

4. The cyclopeptide of claim 3 wherein:
$R_1$ is a side chain of a natural amino acid;
$R_8$ is a side chain of a natural amino acid;

$R_7$ is absent;

X is

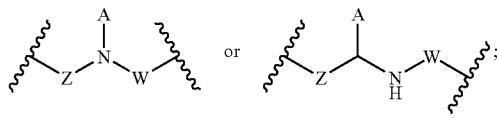

Y is 1,2,3-triazolyl; and $R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{75}Br$, $^{124}I$, $^{125}I$ and $^{131}I$.

5. A cyclopeptide of formula II:

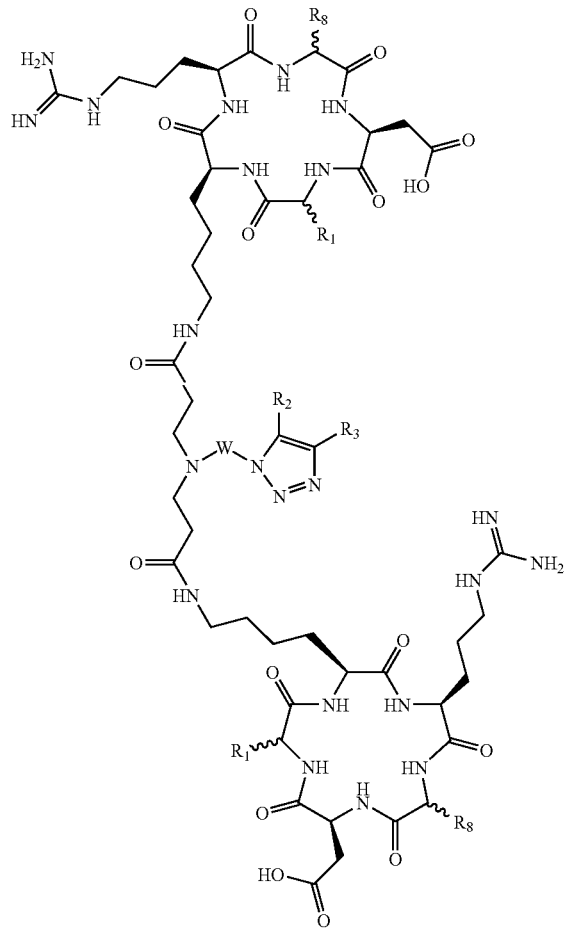

wherein:

each $R_1$ is independently selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{75}Br$, $^{124}I$, $^{125}I$ and $^{131}I$; and W is

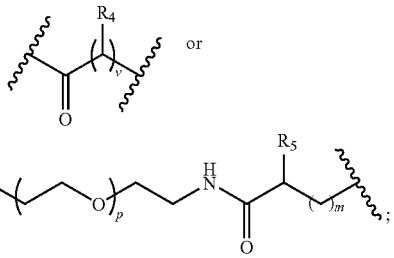

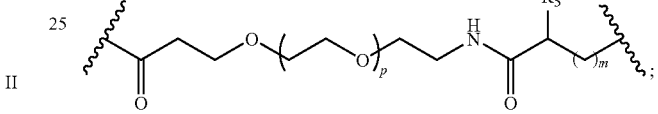

where p is an integer between 0 and 15;

v is 0, 1, 2, or 3;

m is 0, 1 or 2;

each $R_4$ is independently selected from the group consisting of —H, $C_1$-$C_6$ alkyl, $C_2$-$C_6$ alkenyl, and $C_2$-$C_6$ alkynyl, wherein the alkyl, alkenyl, and alkynyl groups are each optionally substituted;

$R_5$ is selected from the group consisting of —H, $C_1$-$C_6$ alkyl, $C_2$-$C_6$ alkenyl, and $C_2$-$C_6$ alkynyl, wherein the alkyl, alkenyl and alkynyl groups are each optionally substituted and wherein the configuration of the chiral center that is substituted with the $R_5$ substituent may be R or S or mixtures thereof; and each $R_8$ is independently selected from the group consisting of a side chain of a natural amino acid and a side chain of an unnatural amino acid, wherein the natural amino acid and the unnatural amino acid is either in the D or L form.

6. The cyclopeptide of claim 5 wherein:

each $R_1$ is benzyl;

$R_2$ is H;

$R_3$ is an optionally substituted $C_1$-$C_6$ alkyl comprising a radionuclide selected from the group consisting of $^{11}C$, $^{13}N$, $^{15}O$, $^{18}F$, $^{75}Br$, $^{124}I$, $^{125}I$ and $^{131}I$;

$R_8$ is a side chain of a natural amino acid; and

W is

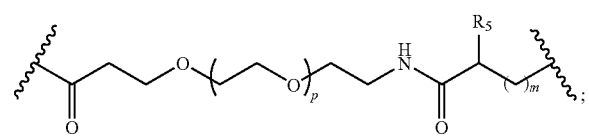

where p is 0, 1, 2, 3, 4, or 5.

7. A cyclopeptide of formula III:

wherein:
- $R_1$ is selected from the group consisting of a side chain of a natural amino acid and a side chain of an unnatural amino acid, wherein the natural amino acid and the unnatural amino acid is either in the D or L form;
- $R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted;
- wherein $R_2$ and $R_3$ are not both H; and either $R_2$ or $R_3$, or both $R_2$ and $R_3$ comprise a radionuclide selected from the group consisting of positron or gamma emitters;
- $R_8$ is selected from the group consisting of a side chain of a natural amino acid and a side chain of an unnatural amino acid, wherein the natural amino acid and the unnatural amino acid is either in the D or L form; and
- X is a linker comprising a hydrophilic moiety selected from the group consisting of hydroxyl, carbonyl, amide (—C(O)NH—), sulfonamide, sulfonate, phosphate, polar amino acid moiety, PEG moiety, sugar mimetic and sugar moiety, or a combination thereof.

8. The cyclopeptide of claim 7 wherein $R_1$ is a side chain of a natural amino acid; $R_8$ is a side chain of a natural amino acid; $R_2$ is hydrogen; and $R_3$ comprises a radionuclide selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$.

9. The cyclopeptide of claim 8 wherein $R_1$ is benzyl; $R_8$ is a side chain of a natural amino acid; and $R_3$ comprises a radionuclide selected from the group consisting of $^{11}C$, $^{13}N$, $^{15}O$, $^{18}F$, $^{124}I$, $^{125}I$, $^{131}I$ and $^{75}Br$.

10. The cyclopeptide of claim 7 wherein:
- $R_1$ is a side chain of a natural amino acid;
- X is selected from the group consisting of:

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle and heterocycle groups are each optionally substituted;

each $R_6$ is independently selected from the group consisting of —H, —OH, $C_1$-$C_6$ alkyl, $C_2$-$C_6$ alkenyl, $C_2$-$C_6$ alkynyl, $C_1$-$C_6$ alkyloxy, aryl-($C_1$-$C_6$ alkylene)-, hydroxy-$C_1$-$C_6$-alkyl, and $C_1$-$C_6$-alkoxy-$C_1$-$C_6$-alkyl, wherein the alkyl, alkenyl, alkynyl, alkyloxy, and aryl-alkylene groups are each optionally substituted;

$R_8$ is a side chain of a natural amino acid;
v is 0, 1, 2, 3, or 4;
m is 0, 1, 2, 3 or 4;
p is an integer between 1 and 110;
q is 1, 2, 3 or 4;
r is 1, 2 or 3;
r' is 0 or 1
s is 1, 2, 3 or 4; and
the radionuclide is selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$;
where the configuration of the chiral centers may be R or S or mixtures thereof.

11. The cyclopeptide of claim 10 wherein:
X is $R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{75}Br$, $^{124}I$, $^{125}I$ and $^{131}I$;

$R_5$ is selected from the group consisting of —H, $C_1$-$C_6$ alkyl, $C_2$-$C_6$ alkenyl, and $C_2$-$C_6$ alkynyl, wherein the alkyl, alkenyl and alkynyl groups are each optionally substituted and wherein the configuration of the chiral center that is substituted with the $R_5$ substituent may be R or S or mixtures thereof; and m is 0, 1 or 2.

12. The cyclopeptide of claim 11, wherein:

$R_2$ is hydrogen;

$R_3$ is selected from the group consisting of $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein $R_3$ comprises a radionuclide selected from the group consisting of $^{11}C$, $^{13}N$, $^{15}O$, and $^{18}F$;

$R_5$ is hydrogen; and m is 0.

13. The cyclopeptide of claim 10, wherein:

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted; wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{75}Br$, $^{124}I$, $^{125}I$, and $^{131}I$;

X is

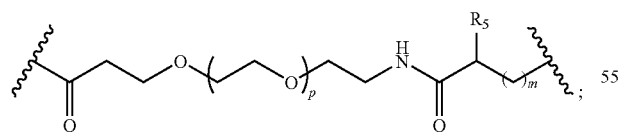

where $R_5$ is selected from the group consisting of —H, $C_1$-$C_6$ alkyl, $C_2$-$C_6$ alkenyl, and $C_2$-$C_6$ alkynyl, wherein the alkyl, alkenyl and alkynyl groups are each optionally substituted and wherein the configuration of the chiral center that is substituted with the $R_5$ substituent may be R or S or mixtures thereof;

m is 0, 1, or 2; and p is an integer between 1 and 90.

14. The cyclopeptide of claim 13, wherein:

$R_2$ is hydrogen;

$R_3$ is selected from the group consisting of $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein $R_3$ comprises a radionuclide selected from the group consisting of $^{11}C$, $^{13}N$, $^{15}O$ and $^{18}F$;

$R_5$ is hydrogen;

m is 0; and p is an integer between 1 and 15.

15. The cyclopeptide of claim 10 wherein:

X is

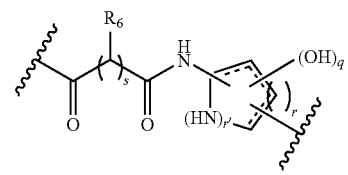

where each $R_6$ is independently selected from the group consisting of —H, —OH, $C_1$-$C_6$ alkyl, $C_2$-$C_6$ alkenyl, $C_1$-$C_6$ alkyloxy, hydroxy-$C_1$-$C_6$-alkyl, and $C_1$-$C_6$-alkoxy-$C_1$-$C_6$-alkyl, wherein the alkyl, alkenyl, and alkyloxy groups are each optionally substituted;

q is 2, 3 or 4;

r is 2 or 3;

r' is 0; and s is 1 or 2.

16. The cyclopeptide of claim 10 wherein:

X is

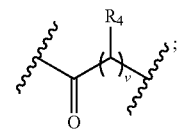

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted; and v is 1, 2, 3, or 4.

17. A radiolabeled cyclopeptide of formula IV:

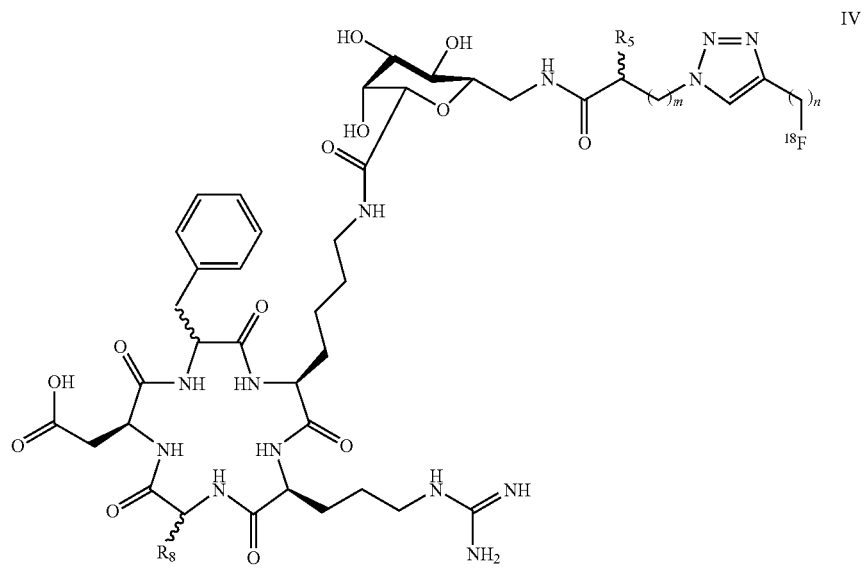

wherein:
$R_5$ is selected from the group consisting of H, $C_1$-$C_6$ alkyl, $C_2$-$C_6$ alkenyl, $C_2$-$C_6$ alkynyl, $C_1$-$C_6$ alkyloxy, aryl, —($C_1$-$C_6$ alkylene)-aryl, 3- to 7-membered carbocycle, 3- to 7-membered heterocycle, hydroxy-$C_1$-$C_6$-alkyl, and $C_1$-$C_6$-alkoxy-$C_1$-$C_6$-alkyl; wherein the alkyl, alkenyl, alkynyl, alkyloxy, aryl, carbocycle and heterocycle groups are each optionally substituted;

$R_8$ is selected from the group consisting of a side chain of a natural amino acid and a side chain of an unnatural amino acid, wherein the natural amino acid and the unnatural amino acid is either in the D or L form;

wherein the chiral centers attached to ⁓bonds are R or S or mixtures thereof;

m is 0, 1, 2, 3 or 4; and n is 1, 2, 3, 4 or 5.

18. The cyclopeptide of claim 17, wherein:
$R_5$ is selected from the group consisting of H, $C_1$-$C_4$ alkyl, $C_2$-$C_4$ alkenyl, and $C_2$-$C_4$ alkynyl, wherein the alkyl, alkenyl and alkynyl groups are each optionally substituted;

wherein the chiral center in the cyclic peptide is R configured and the chiral center bearing the $R_5$ residue is R or S or mixtures thereof;

m is 0, 1 or 2; and n is 1, 2, 3 or 4.

19. The cyclopeptide of claim 18, wherein:
$R_5$ is selected from the group consisting of —H, and an optionally substituted $C_1$-$C_4$ alkyl;

m is 0 or 1; and n is 2, 3 or 4.

20. A radiolabeled cyclopeptide selected from the group consisting of:

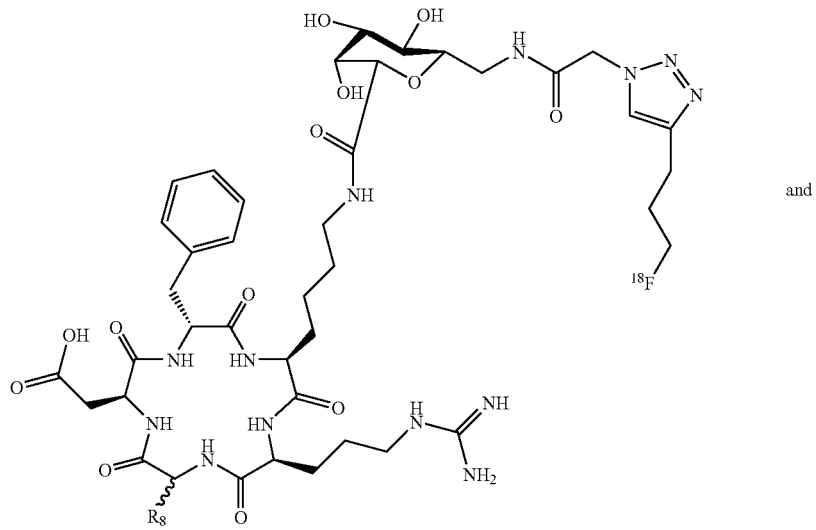

and

-continued
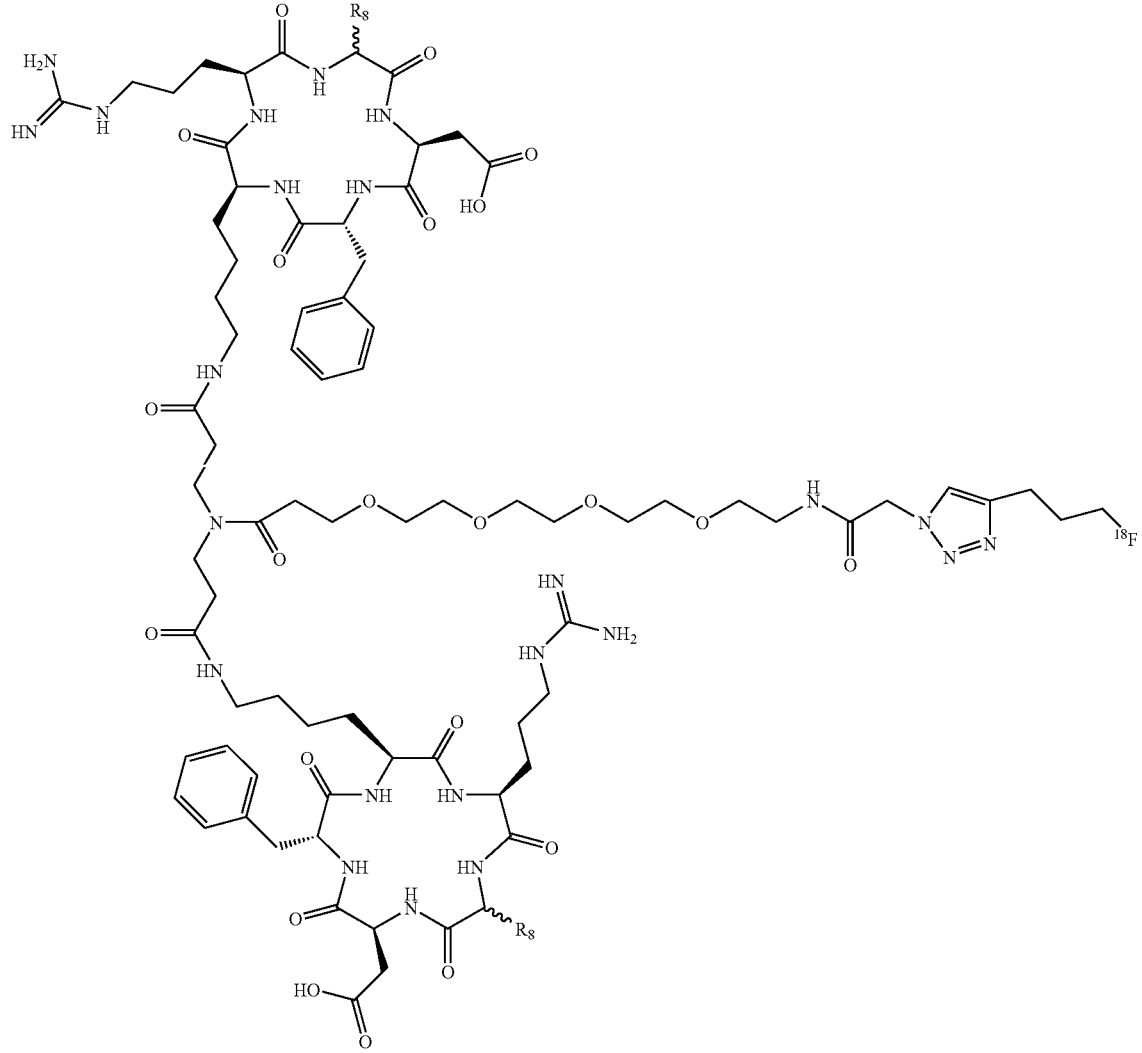
wherein each $R_8$ is selected from the group consisting of a side chain of a natural amino acid and a side chain of an unnatural amino acid, wherein the natural amino acid and the unnatural amino acid is either in the D or L form.
21. A pharmaceutical composition comprising a radiolabeled cyclopeptide of formula I:
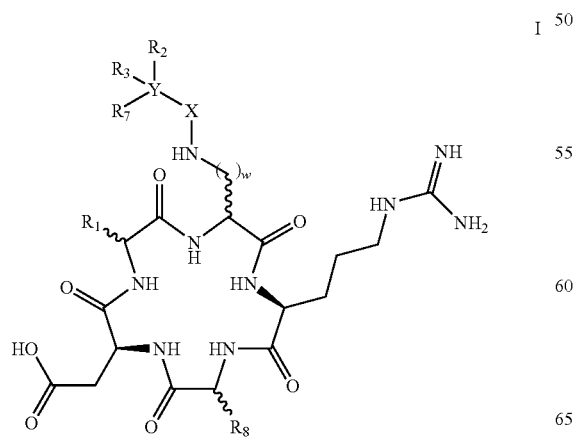

wherein:
R$_1$ is selected from the group consisting of a side chain of a natural amino acid and a side chain of an unnatural amino acid, wherein the natural amino acid and the unnatural amino acid is either in the D or L form;

R$_2$ and R$_3$ are each independently selected from the group consisting of —H, C$_1$-C$_6$ alkyl, C$_2$-C$_6$ alkenyl, C$_2$-C$_6$ alkynyl, C$_1$-C$_6$ alkyloxy, C$_1$-C$_6$ alkoxyalkyl, aryl, aryl-(C$_1$-C$_6$ alkylene)-, 3- to 7-membered carbocycle, 3- to 7-membered heterocycle, hydroxy-C$_1$-C$_6$-alkyl, and C$_1$-C$_6$-alkoxy-C$_1$-C$_6$-alkyl, wherein the alkyl, alkenyl, alkynyl, alkyloxy, alkoxyalkyl, aryl, carbocycle, and heterocycle, groups are each optionally substituted;

R$_7$ is absent or is selected from the group consisting of H, C$_1$-C$_6$ alkyl, C$_2$-C$_6$ alkenyl, C$_2$-C$_6$ alkynyl, aryl, aryl-(C$_1$-C$_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted; wherein R$_2$, R$_3$ and R$_7$ are not all H;

R$_8$ is selected from the group consisting of a side chain of a natural amino acid and a side chain of an unnatural amino acid, wherein the natural amino acid and the unnatural amino acid is either in the D or L form;

X is a 5 or 6-membered heterocycle or a linker comprising a hydrophilic moiety selected from the group consisting of hydroxyl, carbonyl, amide (—C(O)NH—), sulfonamide, sulfonate, phosphate, polar amino acid moiety, PEG moiety, sugar mimetic, and sugar moiety, or a combination thereof;

Y is a 5 or 6-membered heterocycle, or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

where at least one of X and Y, but not both X and Y is a 5 or 6-membered heterocycle; and w is 1, 2, 3, 4, or 5;

wherein any one of X, Y, R$_2$, R$_3$, and R$_7$ comprises a radionuclide selected from the group consisting of positron or gamma emitters;

and a pharmaceutically acceptable carrier.

22. A pharmaceutical composition comprising a radiolabeled cyclopeptide of formula II or formula III:

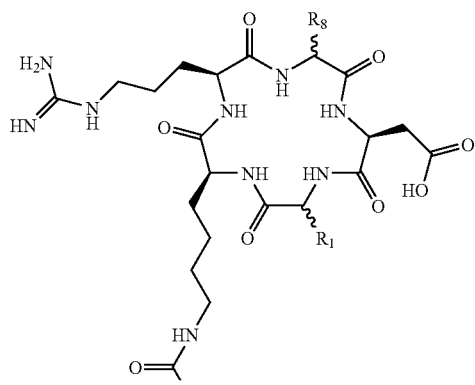

II

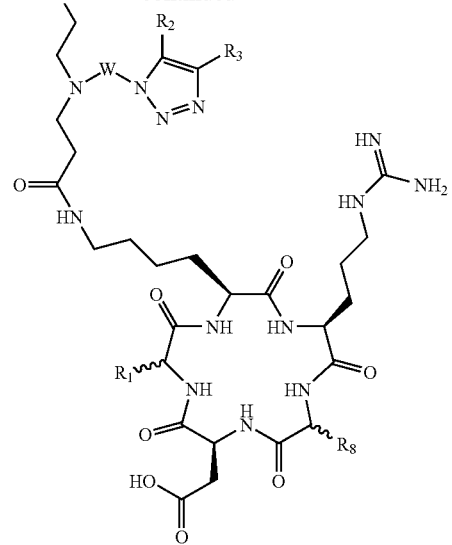

-continued

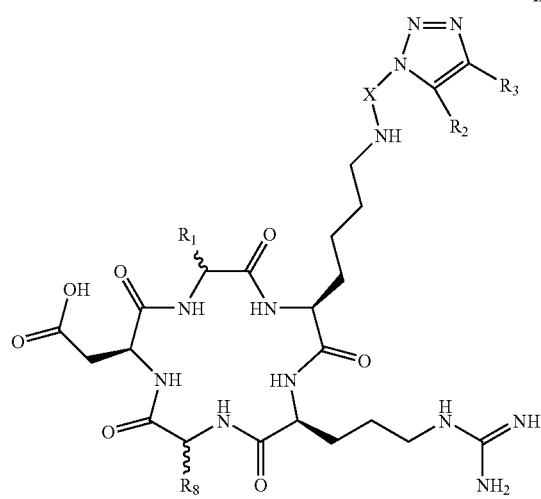

III wherein:
each R$_1$ is independently selected from the group consisting of a side chain of a natural amino acid and a side chain of an unnatural amino acid, wherein the natural amino acid and the unnatural amino acid is either in the D or L form;

R$_2$ and R$_3$ are each independently selected from the group consisting of —H, C$_1$-C$_6$ alkyl, C$_2$-C$_6$ alkenyl, C$_2$-C$_6$ alkynyl, C$_1$-C$_6$ alkyloxy, C$_1$-C$_6$ alkoxyalkyl, aryl, aryl-(C$_1$-C$_6$ alkylene)-, 3- to 7-membered carbocycle, 3- to 7-membered heterocycle, hydroxy-C$_1$-C$_6$-alkyl, and C$_1$-C$_6$-alkoxy-C$_1$-C$_6$-alkyl, wherein the alkyl, alkenyl, alkynyl, alkyloxy, alkoxyalkyl, aryl, carbocycle, and heterocycle, groups are each optionally substituted, wherein R$_2$ and R$_3$ are not both H; and either R$_2$ or R$_3$, or both R$_2$ and R$_3$ comprise a radionuclide selected from the group consisting of $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I, $^{131}$I, $^{99}$Tc, $^{75}$Br, $^{153}$Gd and $^{32}$P;

each of X and W is selected from the group consisting of:

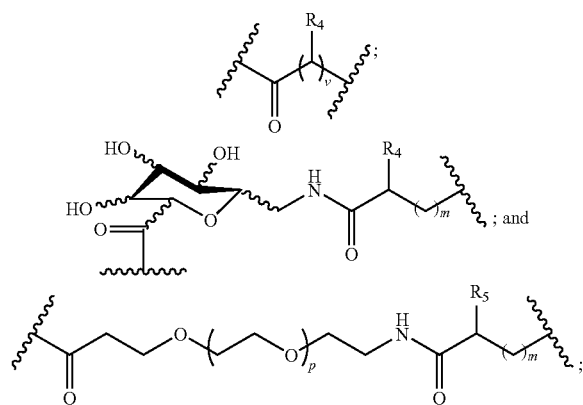

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted;

each $R_8$ is independently selected from the group consisting of a side chain of a natural amino acid and a side chain of an unnatural amino acid, wherein the natural amino acid and the unnatural amino acid is either in the D or L form;

v is 0, 1, 2, 3, or 4;

m is 0, 1, 2, 3 or 4; and p is an integer between 1 and 25;

wherein the configuration of the chiral centers may be R or S or mixtures thereof; and a pharmaceutically acceptable carrier.

23. A pharmaceutical composition comprising a radiolabeled cyclopeptide selected from the group consisting of:

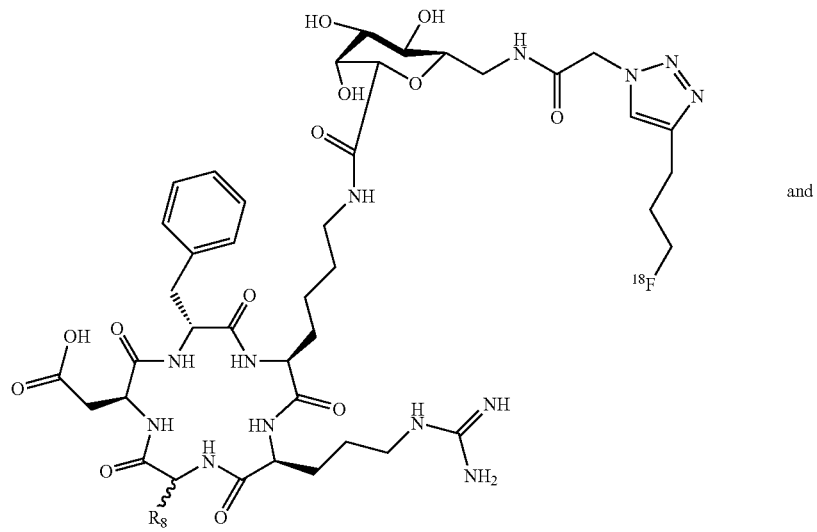

and

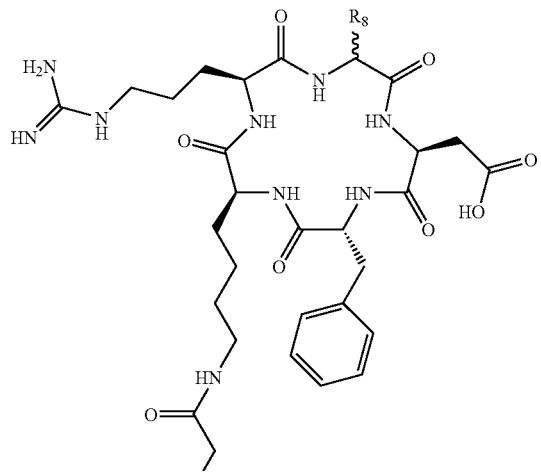

-continued

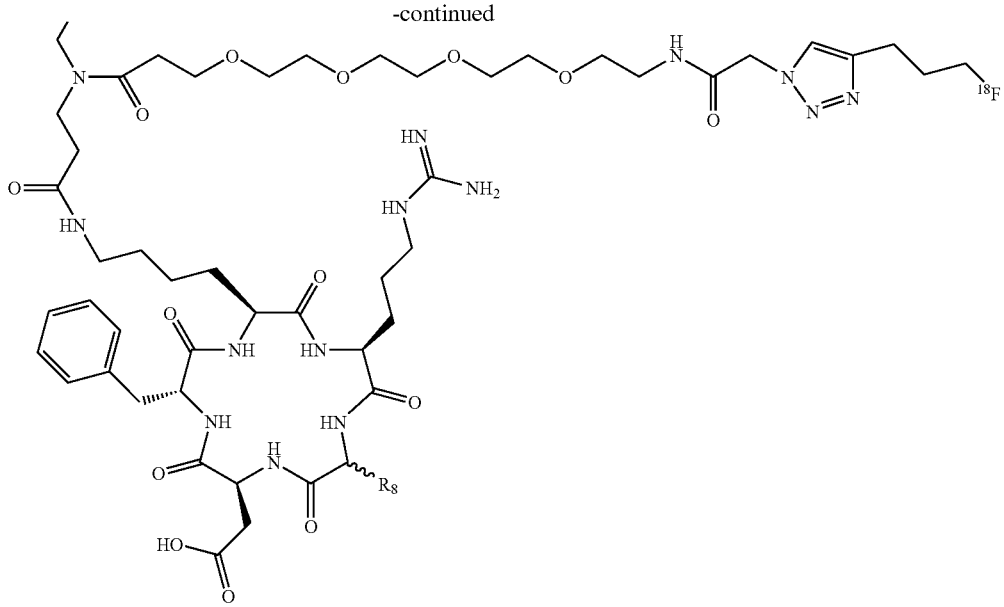

wherein:
each $R_8$ is independently selected from the group consisting of a side chain of a natural amino acid and a side chain of an unnatural amino acid, wherein the natural amino acid and the unnatural amino acid is either in the D or L form;
and a pharmaceutically acceptable carrier.

24. A method of monitoring the level of integrin $\alpha_v\beta_3$ or visualizing integrin $\alpha_v\beta_3$ expression within a body of a patient, the method comprising:
(a) administering to the patient a radiolabeled cyclopeptide; and (b) employing a nuclear imaging technique selected from the group consisting of positron emission tomography (PET) and single photon emission computed tomography (SPECT) for monitoring or visualizing a distribution of the radiolabeled cyclopeptide within the body or within a portion thereof; wherein the radiolabeled cyclopeptide is of formula I:

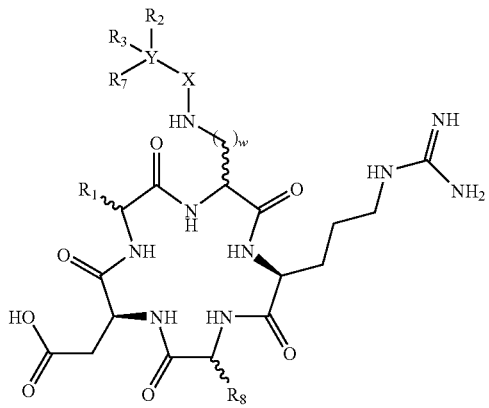

wherein
$R_1$ is selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted;

$R_7$ is absent or is selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted; wherein $R_2$, $R_3$ and $R_7$ are not all H;

$R_8$ is selected from the group consisting of a side chain of a natural amino acid and a side chain of an unnatural amino acid, wherein the natural amino acid and the unnatural amino acid is either in the D or L form;

X is a 5 or 6-membered heterocycle or a linker comprising a hydrophilic moiety selected from the group consisting of hydroxyl, carbonyl, amide (—C(O)NH—), sulfonamide, sulfonate, phosphate, polar amino acid moiety, PEG moiety, sugar mimetic, and sugar moiety, or a combination thereof;

Y is a 5 or 6-membered heterocycle, or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

where at least one of X and Y, but not both X and Y is a 5 or 6-membered heterocycle; and w is 1, 2, 3, 4, or 5;

wherein any one of X, Y, $R_2$, $R_3$, and $R_7$ comprises a radionuclide selected from the group consisting of positron or gamma emitters.

25. A method of monitoring the level of integrin $\alpha_v\beta_3$ or visualizing integrin $\alpha_v\beta_3$ expression within a body of a patient, the method comprising: (a) administering to the patient a radiolabeled cyclopeptide; and (b) employing a nuclear imaging technique selected from the group consisting of positron emission tomography (PET) and single photon emission computed tomography (SPECT) for monitoring or visualizing a distribution of the radiolabeled cyclopeptide within the body or within a portion thereof; wherein the radiolabeled cyclopeptide is of formula II or formula III:

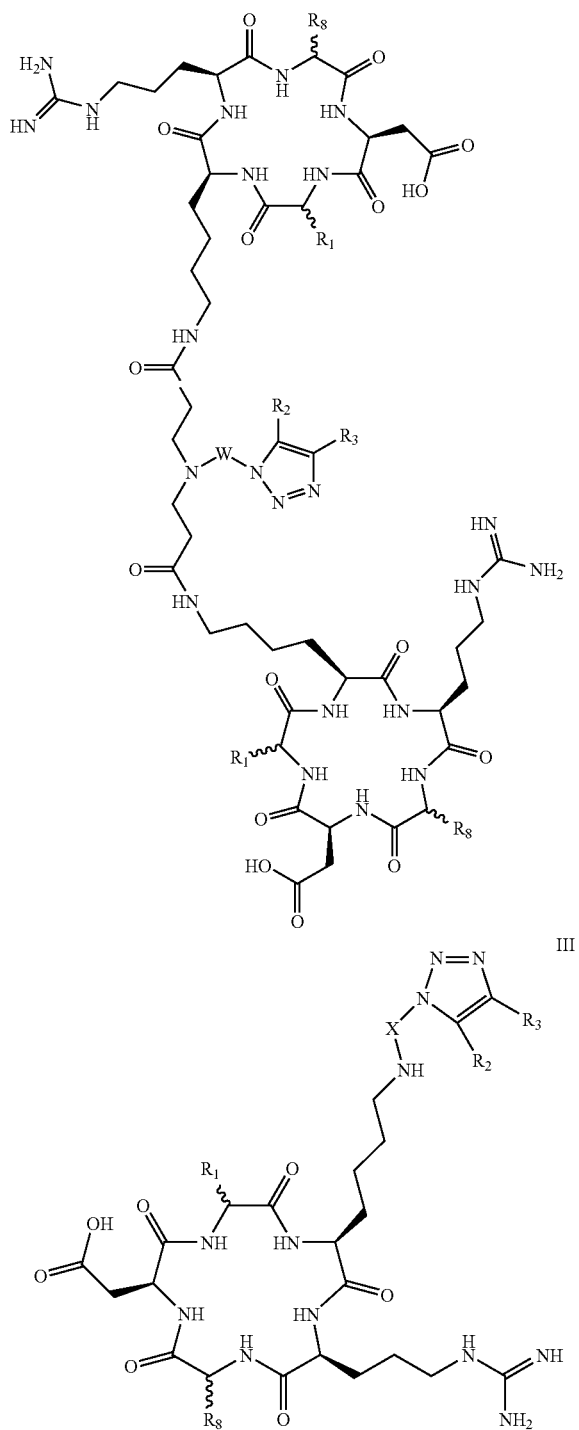

wherein
each $R_1$ is independently selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$;

each of X and W is selected from the group consisting of:

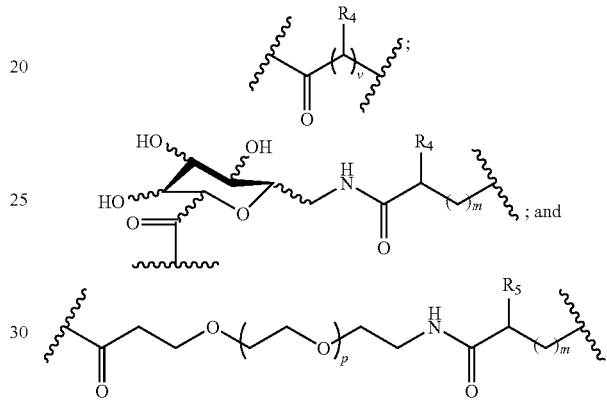

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted;

each $R_8$ is independently selected from the group consisting of a side chain of a natural amino acid and a side chain of an unnatural amino acid, wherein the natural amino acid and the unnatural amino acid is either in the D or L form;

wherein the configuration of the chiral centers may be R or S or mixtures thereof;

v is 0, 1, 2, 3, or 4;
m is 0, 1, 2, 3 or 4; and
p is an integer between 1 and 25.

26. A method of monitoring the level of integrin $\alpha_v\beta_3$ or visualizing integrin $\alpha_v\beta_3$ expression within a body of a patient, the method comprising: (a) administering to the patient a radiolabeled cyclopeptide; and (b) employing a nuclear imaging technique selected from the group consisting of positron emission tomography (PET) and single photon emission computed tomography (SPECT) for monitoring or visualizing a distribution of the radiolabeled cyclopeptide within the body or within a portion thereof; wherein the radiolabeled cyclopeptide is selected from the group consisting of:

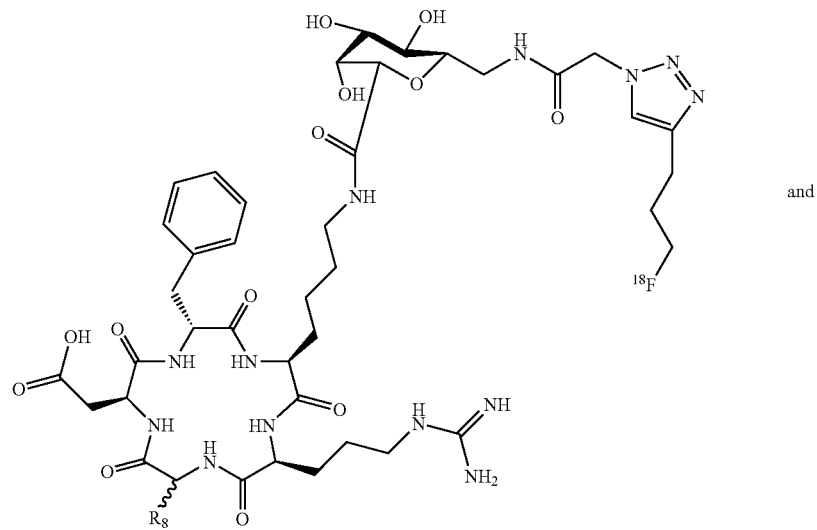
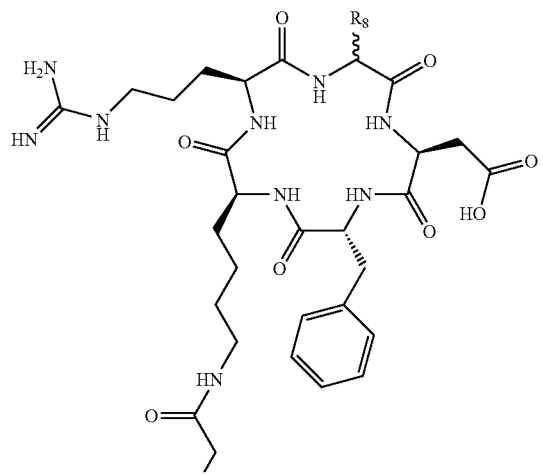
and
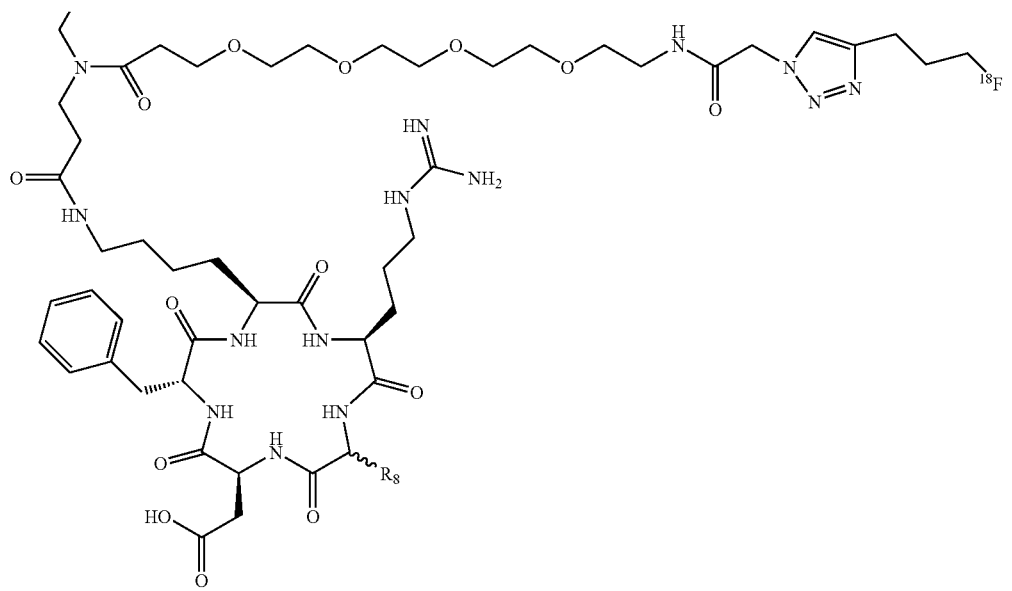

wherein:
each $R_8$ is independently selected from the group consisting of a side chain of a natural amino acid and a side chain of an unnatural amino acid, wherein the natural amino acid and the unnatural amino acid is either in the D or L form.

27. A method for imaging of blood vessel growth in solid tumors based on expression of integrin $\alpha_v\beta_3$ within the body of a patient, the method comprising: (a) administering to the patient a radiolabeled cyclopeptide; (b) employing a nuclear imaging technique selected from the group consisting of positron emission tomography (PET) and single photon emission computed tomography (SPECT) for imaging a distribution of the radiolabeled cyclopeptide within the body or within a portion thereof; and c) correlating the distribution of the radiolabeled cyclopeptide to the growth of blood vessels in solid tumors, wherein the radiolabeled cyclopeptide is of formula I:

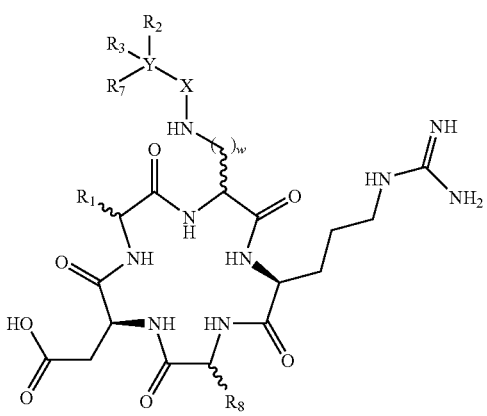

wherein:
$R_1$ is selected from the group consisting of a side chain of a natural amino acid and a side chain of an unnatural amino acid, wherein the natural amino acid and the unnatural amino acid is either in the D or L form;
$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted;
$R_7$ is absent or is selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted; wherein $R_2$, $R_3$ and $R_7$ are not all H;
$R_8$ is selected from the group consisting of a side chain of a natural amino acid and a side chain of an unnatural amino acid, wherein the natural amino acid and the unnatural amino acid is either in the D or L form;
X is a 5 or 6-membered heterocycle or a linker comprising a hydrophilic moiety selected from the group consisting of hydroxyl, carbonyl, amide (—C(O)NH—), sulfonamide, sulfonate, phosphate, polar amino acid moiety, PEG moiety, sugar mimetic, and sugar moiety, or a combination thereof;
Y is a 5 or 6-membered heterocycle, or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;
where at least one of X and Y, but not both X and Y is a 5 or 6-membered heterocycle; and
w is 1, 2, 3, 4, or 5;
wherein any one of X, Y, $R_2$, $R_3$, and $R_7$ comprises a radionuclide selected from the group consisting of positron or gamma emitters.

28. A method for imaging of blood vessel growth in solid tumors based on expression of integrin $\alpha_v\beta_3$ within the body of a patient, the method comprising: (a) administering to the patient a radiolabeled cyclopeptide; (b) employing a nuclear imaging technique selected from the group consisting of positron emission tomography (PET) and single photon emission computed tomography (SPECT) for imaging a distribution of the radiolabeled cyclopeptide within the body or within a portion thereof; and c) correlating the distribution of the radiolabeled cyclopeptide to the growth of blood vessels in solid tumors, wherein the radiolabeled cyclopeptide is of formula II or formula III:

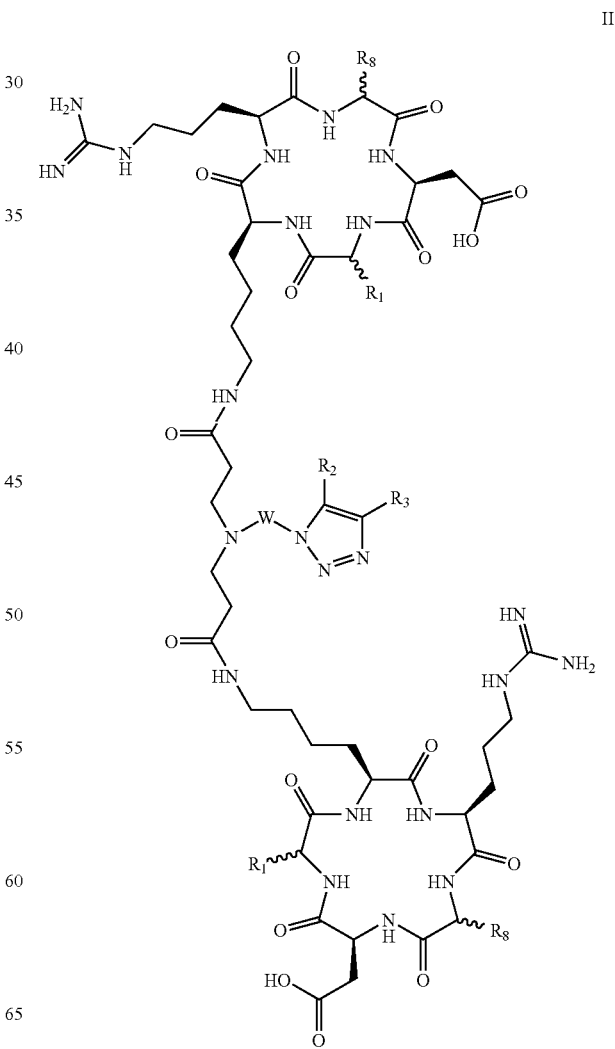

-continued

III

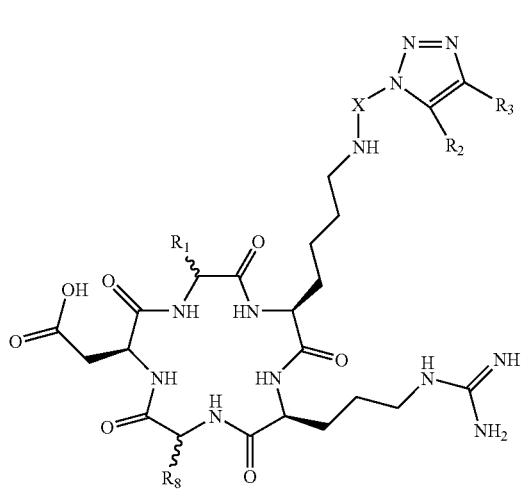

wherein:

each $R_1$ is independently selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of —H, $C_1$-$C_6$ alkyl, $C_2$-$C_6$ alkenyl, $C_2$-$C_6$ alkynyl, $C_1$-$C_6$ alkyloxy, $C_1$-$C_6$ alkoxyalkyl, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, alkoxyalkyl, aryl, carbocycle, and heterocycle, groups are each optionally substituted, wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$;

each of X and W is selected from the group consisting of:

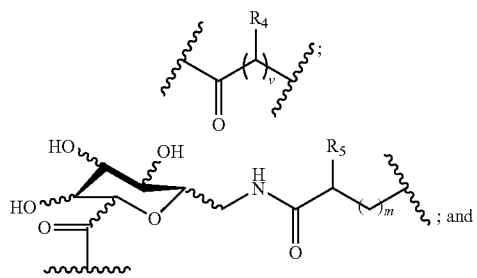

-continued

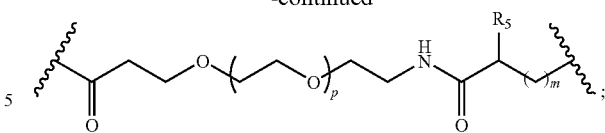

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted;

each $R_8$ is independently selected from the group consisting of a side chain of a natural amino acid and a side chain of an unnatural amino acid, wherein the natural amino acid and the unnatural amino acid is either in the D or L form;

wherein the configuration of the chiral centers may be R or S or mixtures thereof;

v is 0, 1, 2, 3, or 4;

m is 0, 1, 2, 3 or 4; and p is an integer between 1 and 25.

29. A method for imaging of blood vessel growth in solid tumors based on expression of integrin $\alpha_v\beta_3$ within the body of a patient, the method comprising: (a) administering to the patient a radiolabeled cyclopeptide; (b) employing a nuclear imaging technique selected from the group consisting of positron emission tomography (PET) and single photon emission computed tomography (SPECT) for imaging a distribution of the radiolabeled cyclopeptide within the body or within a portion thereof; and c) correlating the distribution of the radiolabeled cyclopeptide to the growth of blood vessels in solid tumors, wherein the radiolabeled cyclopeptide is selected from the group consisting of:

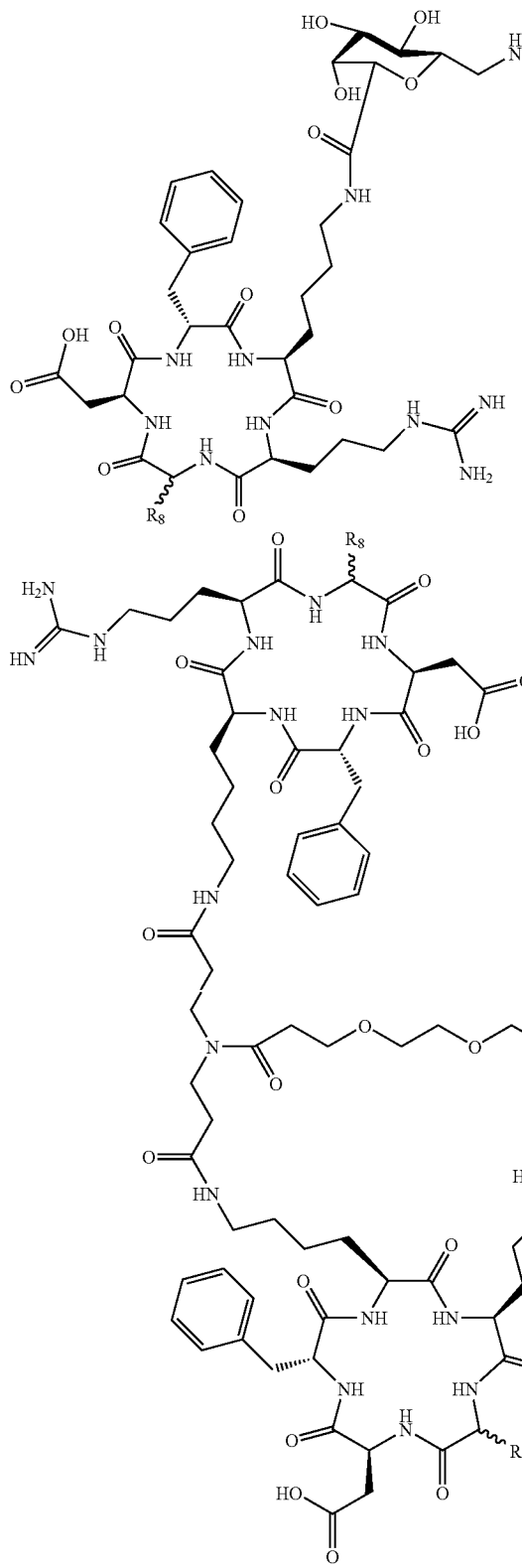
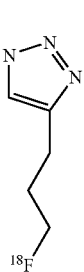
and
wherein:
each $R_8$ is independently selected from the group consisting of a side chain of a natural amino acid and a side chain of an unnatural amino acid, wherein the natural amino acid and the unnatural amino acid is either in the D or L form.
* * * * *